United States Patent
Albright et al.

(10) Patent No.: US 6,544,984 B1
(45) Date of Patent: Apr. 8, 2003

(54) 2,3,4,5-TETRAHYDRO-1H-(1,4) BENZODIAZEPINE-3-HYDROXAMIC ACIDS

(75) Inventors: Jay Donald Albright; Efren Guillermo Delos Santos, both of Nanuet; Jeremy Ian Levin, New City, all of NY (US); James Ming Chen, Bedminster, NJ (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/492,622

(22) Filed: Jan. 27, 2000

Related U.S. Application Data

(60) Provisional application No. 60/198,243, filed on Jan. 27, 1999.

(51) Int. Cl.[7] ...................... A61K 31/55; C07D 243/14; A61P 19/00
(52) U.S. Cl. ........................................ 514/221; 540/573
(58) Field of Search ............................ 514/221; 540/573

(56) References Cited

U.S. PATENT DOCUMENTS

| | | | |
|---|---|---|---|
| 5,455,258 A | 10/1995 | MacPherson et al. | 514/357 |
| 5,753,653 A | 5/1998 | Bender et al. | 514/227.5 |
| 6,071,903 A * | 6/2000 | Albright et al. | 514/221 |

FOREIGN PATENT DOCUMENTS

| | | |
|---|---|---|
| WO | WO 96/33172 | 10/1996 |
| WO | WO9718194 | 5/1997 |
| WO | WO9720824 | 6/1997 |
| WO | WO9808822 | 3/1998 |
| WO | WO9808823 | 3/1998 |
| WO | WO9808825 | 3/1998 |
| WO | WO9808827 | 3/1998 |
| WO | WO 99/37625 | 7/1999 |

OTHER PUBLICATIONS

Yu et al., Drugs and Aging, 11: 229–244 (1997).
Beckett et al., Drug Discovery Today, vol. 1 #1 (Research Focus) 16–26 (1996).
Curr. Opin. Ther. Patents, 4(1), 7–16 (1994).
Morphy et al., Curr. Medicinal Chem., 2: 743–762 (1995).
Davidson et al., Exp. Opin. Ther. Patents 5(2): 1087–1110 (1995).
Porter et al., Exp. Opin. Ther. Patents 5(12): 1287–1296 (1996).
Current Pharma. Design, 2: 524–661 (1996).
Current Pharma. Design, 2: 662–667 (1996).
Levy et al., Emerging Drugs, 2: 205–230 (1997).

* cited by examiner

Primary Examiner—Brenda Coleman
(74) Attorney, Agent, or Firm—John W. Hogan, Jr.

(57) ABSTRACT

Compounds having the following formula:

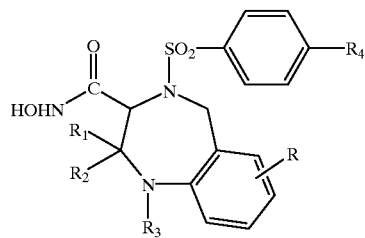

are useful in treating disease conditions mediated by matrix metalloproteinases and TACE, such as tumor growth, osteoarthritis, rheumatoid arthritis and degenerative cartilage loss.

54 Claims, No Drawings

2,3,4,5-TETRAHYDRO-1H-(1,4) BENZODIAZEPINE-3-HYDROXAMIC ACIDS

This application claims the benefit of U.S. Provisional Application No. 60/198,243, filed Jan. 27, 1999.

FIELD OF INVENTION

This invention relates to 4-(4-substituted-benzenesulfonyl)-2,3,4,5-tetrahydro-1H-[1,4]benzodiazepine-3-hydroxamic acids which act as matrix metalloproteinase inhibitors and as inhibitors of TNF-α converting enzyme(TACE). The compounds of the present invention are useful in disease conditions mediated by matrix metalloproteinases and TACE, such as tumor growth, osteoarthritis, rheumatoid arthritis and degenerative cartilage loss.

BACKGROUND OF THE INVENTION

Matrix metalloproteinases (MMPs) are a group of enzymes that have been implicated in the pathological destruction of connective tissue and basement membranes. These zinc-containing endopeptidases consist of several subsets of enzymes, including collagenases, stromelysins and gelatinases. Of these, the gelatinases have been shown to be the MMPs most intimately involved with the growth and spread of tumors.

For example, it is known that the level of expression of gelatinase is elevated in malignancies, and that gelatinase can degrade the basement membrane which leads to tumor metastasis. Angiogenesis, required for the growth of solid tumors, has also recently been shown to have a gelatinase component to its pathology as reported in "Matrix Metalloproteinases, Novel Targets for Directed Cancer Therapy", *Drugs and Aging*, 11:229–244 (1997).

Other conditions mediated by MMPs include restenosis, MMP-mediated osteopenias, inflammatory diseases of the central nervous system, skin aging, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age-related macular degeneration, diabetic retinopathy, proliferative vitreoretinopathy, retinopathy of prematurity, ocular inflammation, keratoconus, Sjogren's syndrome, myopia, ocular tumors, ocular angiogenesis/ neo-vascularization and corneal graft rejection. Studies relating to these conditions are set forth, e.g., in "Recent Advances in Matrix Metalloproteinase Inhibitor Research", R. P. Beckett et al., *Research Focus*, 1:16–26, (1996); *Curr. Opin. Ther. Patents.* 4(1): 7–16, (1994); *Curr. Medicinal Chem.*, 2: 743–762, (1995); *Exp. Opin. Ther. Patents*, 5(2): 1087–110, (1995); *Exp. Opin. Ther. Patents*, 5(12): 1287–1196, (1995); "Inhibition of Matrix Metallo-proteinases: Structure Based Design", *Current Pharmaceutical Design*, 2:524–661, (1996). "Matrix Metalloproteinase Inhibitor Drugs", *Emerging Drugs*, 2:205–230 (1997).

TNF-α converting enzyme (TACE) catalyzes the formation of TNF-α from membrane bound TNF-α precursor protein. TNF-α is a pro-inflammatory cytokine that is believed to have a role in rheumatoid arthritis, septic shock, graft rejection, cachexia, anorexia, inflammation, congestive heart failure, inflammatory disease of the central nervous system, inflammatory bowel disease, insulin resistance and HIV infection, in addition to its well-documented antitumor properties. Research with anti-TNF-α antibodies in transgenic animals has demonstrated that blocking the formation of TNF-α inhibits the progression of arthritis. This observation has recently been extended to humans as described in "TNF-α in Human Diseases", *Current Pharmaceutical Design*, 2:662–667 (1996).

It is expected that small molecule inhibitors of MMPs and TACE would have the potential for treating a variety of disease states. Although a variety of MMP and TACE inhibitors are known, many of these molecules are peptidic and peptide-like which demonstrate bioavailability and pharmacokinetic problems. Long acting, orally bioavailable non-peptide inhibitors of MMPs and/or TACE would thus be highly desirable for the treatment of the disease states discussed above.

U.S. Pat. No. 5,455,258 discloses 2-substituted-2-(arylsulfonylamino) hydroxyamic acids and their use as MMP inhibitors. WO 97/18194, discloses N-(arylsulfonyl) tetrahydroisoquinolone-hydroxamic acids and related bicyclic derivatives thereof and their use as MMP inhibitors. WO 97/20824 and U.S. Pat. No. 5,753,653 disclose 1-(arylsulfonyl)-4-(substituted)piperazine-2-hydroxamic acids, 4-(arylsulfonyl)morpholine-3-hydroxamic acids, 4-(arylsulfonyl)-tetrahydro-2H,1,4-thiazine-3-hydroxamic acids, 3-(substituted-1-(arylsulfonyl)hexahydro-2-hydroxamic acids and related compounds as useful MMP inhibitors.

WO 98/08822, WO 98/08823 and WO 98/08825, disclose 6-membered 1-(arylsulfonyl)hexahydropyrimidine-2-hydroxamic acids, 1-substituted-3-[(4-methoxybenzenesulfonyl)]hexahydropyrimidine-4-hydroxamic acids, 4-(arylsulfonyl)-tetrahydro-1,2-thiazine-3-hydroxamic acids and (arylsulfonyl)-4-substitutedpiperazine-2-hydroxamic acids. WO 98/08827 discloses 4-(arylsulfonyl)-hexahydrothiazepine-3-hydroxamic acids and 4-(arylsulfonyl)-hexadydro[1,4]diazepine-3-hydroxamic acids.

SUMMARY OF THE INVENTION

This invention relates to novel derivatives of substituted 2,3,4,5-tetrahydro-1H-[1,4]benzodiazepine-3-carboxylic acid, hydroxamide which exhibit inhibitory activity against MMPs. The compounds of the present invention are represented by the following formula 1

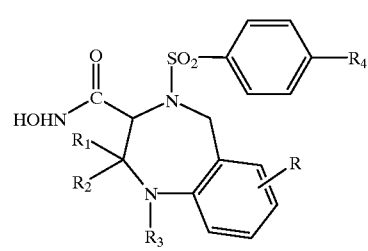

wherein
R is selected from hydrogen, $(C_1-C_3)$alkyl, —CN, —OR', —SR', —CF$_3$, —OCF$_3$, Cl, F, NH$_2$, NH$(C_1-C_3)$alkyl, —N(R')CO$(C_1-C_3)$alkyl, —N(R')(R'), NO$_2$, —CONH$_2$, —SO$_2$NH$_2$, —SO$_2$N(R')(R'), or —N(R')COCH$_2$O—$(C_1-C_3)$alkyl, wherein R' is $(C_1-C_3)$ alkyl or hydrogen;

$R_4$ is $(C_2-C_6)$ alkyl-O— containing one triple bond;

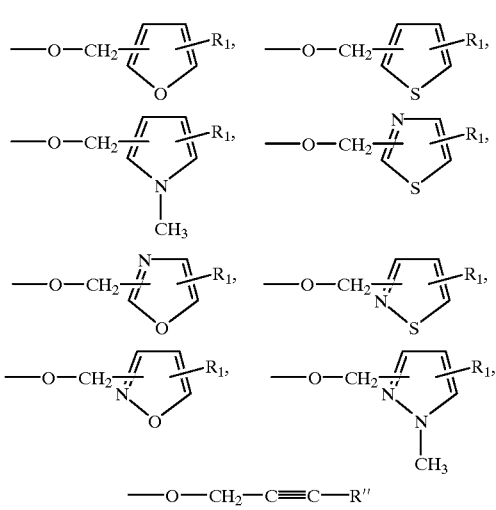

wherein R" is hydrogen, —$CH_2OH$, $(C_1-C_6)$alkyl, $(C_1-C_6)$alkyl-O—$CH_2$—, $(C_1-C_6)$alkyl-S—$CH_2$—, $(C_1-C_6)$alkyl-NH—$CH_2$—, $[(C_1-C_3)$alkyl$]_2$-$NCH_2$—, $(C_1-C_6)$oydodkyl-O—$CH_2$—, $((C_1-C_3)$dkyl$)_2$-N—$(CH_{22-4}NHCH_2$—, $[(C_1-C_3)$dkyl$)_2$-N—$(CH_2)_{2-4}$N$(CH_3)CH_2$—,

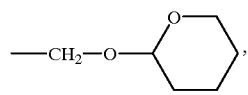

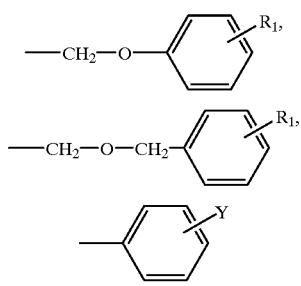

$R_1$ and $R_2$ are each, independently, hydrogen or $C_1-C_3$alkyl; $R_3$ is $(C_1-C_8)$alkyl, $NH_2CH_2CO$—, $(C_1-C_6)$alkyl$NHCH_2CO$—, $HO(CH_2)_mCO$—, HCO—, Aryl$(CH_2)_nCO$—, Heteroaryl$(CH_2)_nCO$—, $(C_1-C_3)$alkyl-O—$(CH_2)_nCO$—, $(C_1-C_3)$alkylCO—, $(C_1-C_3)$alkylCO—$NHCH_2CO$—, $(C_3-C_7)$cycloalkylCO—, $(C_1-C_3)$alkyl$SO_2$—, Aryl$(CH_2)_nSO_2$—, Heteroaryl$(CH_2)_nSO_2$—, $(C_1-C_3)$alkyl-O—$(CH_2)_m$—$SO_2$—, $(C_1-C_3)$alkyl-O—$(CH_2)_m$—, $(C_1-C_3)$alkyl-O—$(C_1-C_3)$alkyl, HO—$(C_1-C_3)$alkyl-O—$(C_1-C_3)$alkyl, Aryl-O—$CH_2CO$—, Heteroaryl-O—$CH_2CO$—, ArylCH=CHCO—, HeteroarylCH=CHCO—, $(C_1-C_3)$alkylCH=CHCO—,

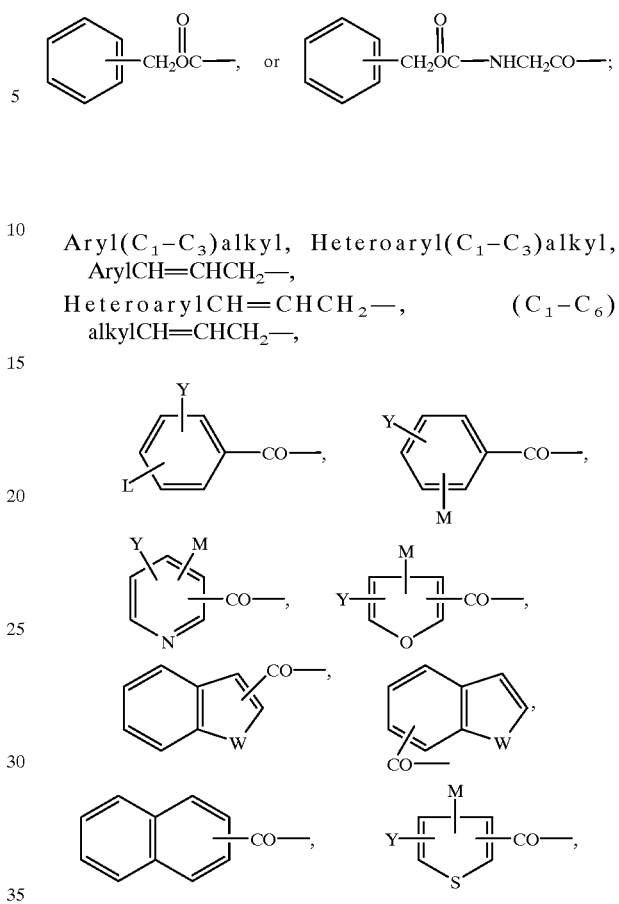

Aryl$(C_1-C_3)$alkyl, Heteroaryl$(C_1-C_3)$alkyl, ArylCH=CHCH$_2$—, HeteroarylCH=CHCH$_2$—, $(C_1-C_6)$alkylCH=CHCH$_2$—,

R'OCH$_2$CH(OR')CO—, (R'OCH$_2$)$_2$C(R')CO—,

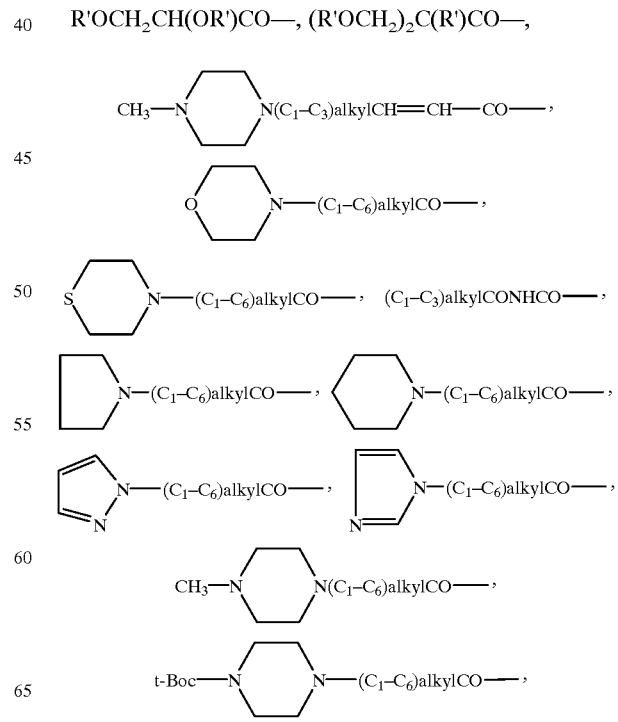

-continued

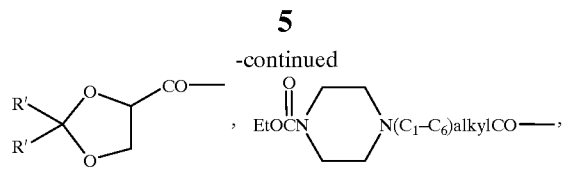

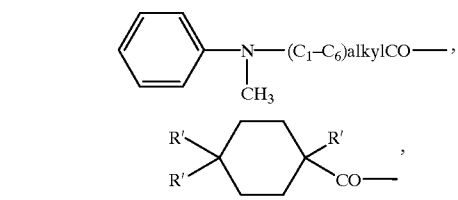

[(C$_1$–C$_6$)alkyl]$_2$-N—(C$_1$–C$_6$)alkyl CO—, or (C$_1$–C$_6$)alkyl-NH—(C$_1$–C$_6$)alkylCO—;

wherein m=1 to 3; n=0 to 3;

Aryl is

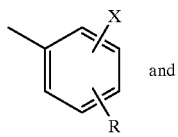 and

Heteroaryl is

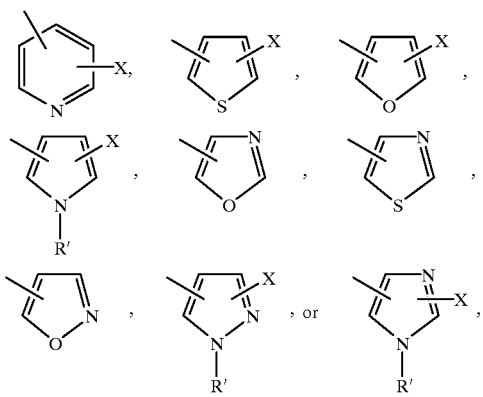

wherein X is hydrogen, halogen, (C$_1$–C$_3$) alkyl or —OCH$_3$ and R and R' are as defined above;

L is hydrogen, (C$_1$–C$_3$)alkyl, —CN, —OR', —SR', —CF$_3$, —OCF$_3$, Cl, F, NH$_2$, —NH—(C$_1$–C$_3$)alkyl, —N(R')CO(C$_1$–C$_3$)alkyl, N(R')(R'), —NO$_2$, —CONH$_2$, —SO$_2$NH$_2$, —SO$_2$N(R')(R'), —N(R')COCH$_2$O—(C$_1$–C$_3$)alkyl,

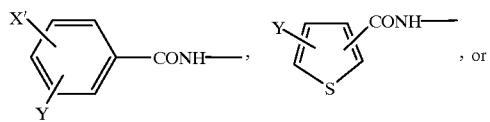

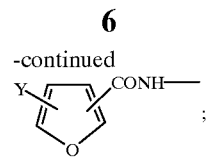

M is

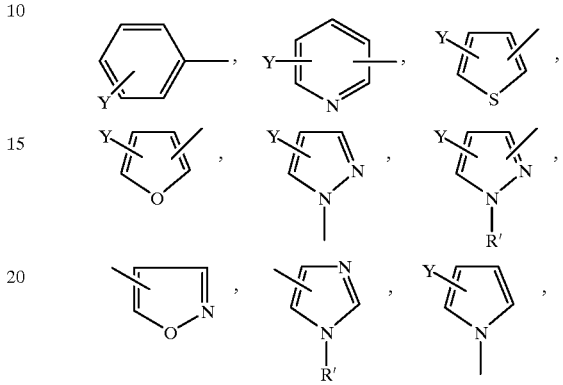

or N(R')(R') where R' is as defined above;

W is O, S, NH or N(C$_1$–C$_3$)alkyl;

Y is hydrogen, F, Cl, CF$_3$ or OCH$_3$; and X' is halogen, hydrogen, (C$_1$–C$_3$)alkyl, O—(C$_1$–C$_3$)alkyl, or —CH$_2$OH; and pharmaceutically acceptable salts thereof.

DETAILED DESCRIPTION OF THE INVENTION

Preferably, the compounds of the present invention are those of formula 1 wherein R is hydrogen, (C$_1$–C$_3$) alkyl, —CN, —OR', —SR', —CF$_3$, —OCF$_3$, Cl, F, NH$_2$, NH(C$_1$–C$_3$)alkyl, —N(R')CO(C$_1$–C$_3$)alkyl, —N(R')(R'), NO$_2$, —CONH$_2$, —SO$_2$NH$_2$, —SO$_2$N(R')(R'), or —N(R')COCH$_2$O—(C$_1$–C$_3$)alkyl, wherein R' is (C$_1$–C$_3$) alkyl or hydrogen;

$R_4$ is $(C_1-C_6)$ alkyl-O— containing one triple bond,

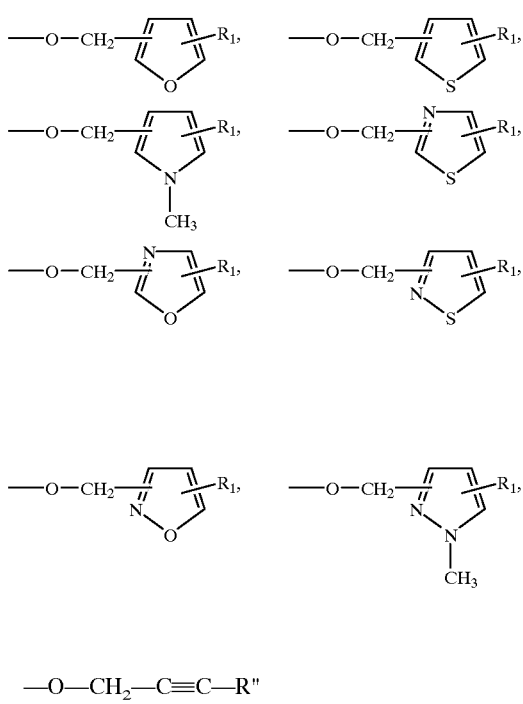

—O—CH$_2$—C≡C—R"

wherein R" is hydrogen, —CH$_2$OH, $(C_1-C_6)$alkyl, $(C_1-C_6)$alkyl-O—CH$_2$—, $(C_1-C_6)$akyl-S—CH$_2$—, $(C_1-C_6)$alkyl-NH—CH$_2$—, $[(C_1-C_3)$alkyl$]_2$-NCH$_2$—, $(C_1-C_6)$cycloalkyl-O—CH$_2$—, $[(C_1-C_3)$alkyl$]_2$-N—(CH$_2$)$_{2-4}$NHCH$_2$—, $[(C_1-C_3)$alkyl$]_2$-N—(CH$_2$)$_{2-4}$N(CH$_3$)CH$_2$—,

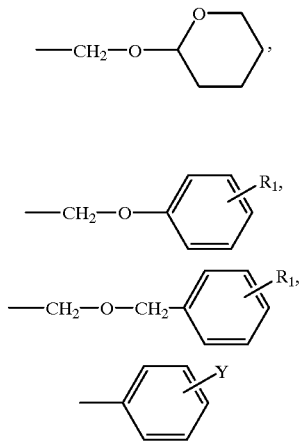

$R_1$ and $R_2$ are each, independently, hydrogen or CH$_3$;

$R_3$ is $(C_1-C_8)$alkyl, NH$_2$CH$_2$CO—, $(C_1-C_6)$alkylNHCH$_2$CO—, HO(CH$_2$)$_m$CO—, HCO—, Aryl(CH$_2$)$_n$CO—, Heteroaryl(CH$_2$)$_n$CO—, $(C_1-C_3)$alkyl-O—(CH$_2$)$_n$CO—, $(C_1-C_3)$alkylCO—, $(C_1-C_3)$alkylCO—NHCH$_2$CO—, $(C_3-C_7)$cycloalkylCO—, Aryl-O—CH$_2$CO—, HeteroarylOCH$_2$CO—,

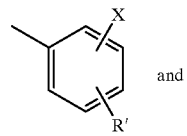

wherein m=1 to 3; n=0 to 3;

Aryl is

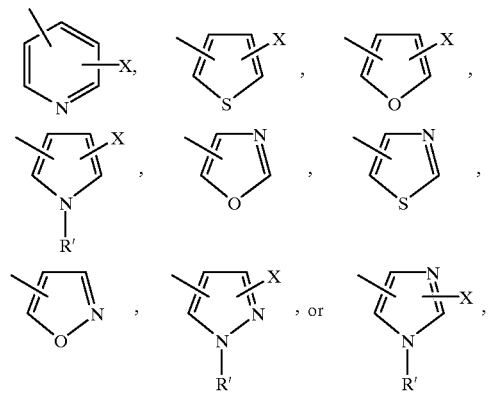

and

Heteroaryl is wherein X is hydrogen, halogen, $(C_1-C_3)$alkyl, or —OCH$_3$ wherein R and R' are as defined above; and pharmaceutically acceptable salts thereof.

It is more preferred that the compounds of the present invention include those of formula 1 wherein R is hydrogen, $(C_1-C_3)$ alkyl, —CN, —OR', —SR', —CF$_3$, —OCF$_3$, Cl, F, NH$_2$, NH(C$_1$-C$_3$)alkyl, —N(R')CO(C$_1$-C$_3$)alkyl, —N(R')(R'), NO$_2$, —CONH$_2$, —SO$_2$NH$_2$, —SO$_2$N(R')(R'), or —N(R')COCH$_2$O—(C$_1$-C$_3$)alkyl, wherein R' is (C$_1$-C$_3$) alkyl or hydrogen;

$R_4$ is $(C_1-C_6)$ alkyl-O— containing one triple bond,

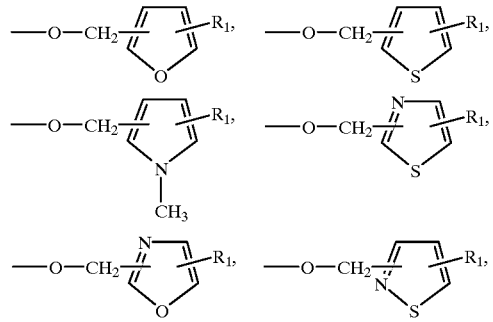

-continued

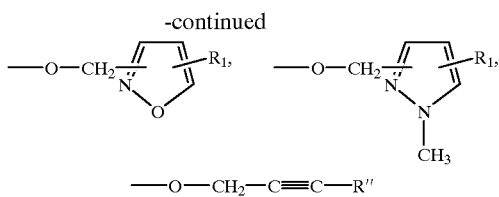

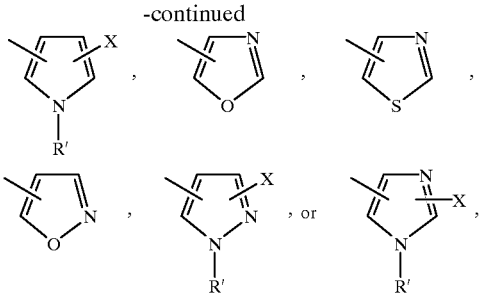

wherein R" is hydrogen, —CH$_2$OH (C$_1$–C$_6$)alkyl, (C$_1$–C$_6$)alkyl-O—CH$_2$—, (C$_1$–C$_6$)alkyl-S—CH$_2$—, (C$_1$–C$_6$)alkyl-NH—CH$_2$—, [(C$_1$–C$_3$)alkyl]$_2$-NCH$_2$—, (C$_1$–C$_6$)cycloalkyl-O—CH$_2$—, [(C$_1$–C$_3$) alkyl]$_2$-N—(CH$_2$)$_{2-4}$NHCH$_2$—, [(C$_1$–C$_3$) alkyl]$_2$-N—(CH$_2$)$_{2-4}$N(CH$_3$)CH$_2$—,

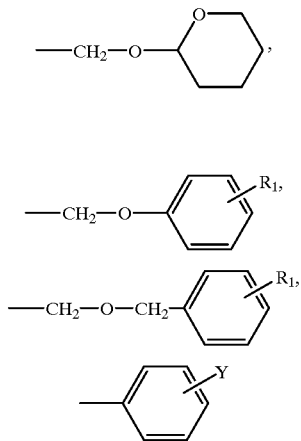

R$_1$ and R$_2$ are each, independently hydrogen or CH$_3$;

R$_3$ is (C$_1$–C$_3$)alkylCO—, (C$_1$–C$_3$)alkyl-O—(CH$_2$)$_m$CO—, ArylCO— wherein m=1 to 3; n=0 to 3;

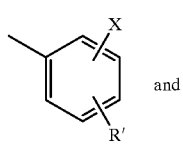 and

Aryl is

Heteroaryl is

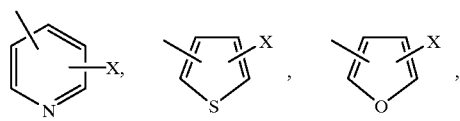

wherein X is hydrogen, halogen, (C$_1$–C$_3$) alkyl or —OCH$_3$ and R and R' are as defined above; and pharmaceutically acceptable salts thereof.

It is more preferred that the compounds of the present invention include those of formula 1 wherein R is hydrogen, (C$_1$–C$_3$) alkyl,—CN,—OR,—SR,—CF$_3$,OCF$_3$,Cl, F, NH$_2$, NH (C$_1$–C$_3$) alkyl, —N(R')CO(C$_1$–C$_3$)alkyl, —N(R')(R'), NO$_2$,—CONH$_2$,—SO$_2$NH$_2$, —SO$_2$ NH$_2$, SO$_2$N(R')(R') or —N(R') COCHO—(C$_1$–C$_3$) alkyl, wherein R' is (C$_1$–C$_3$) alkyl or hydrogen;

R$_4$ is (C$_1$–C$_6$) alkyl-O— containing one triple bond

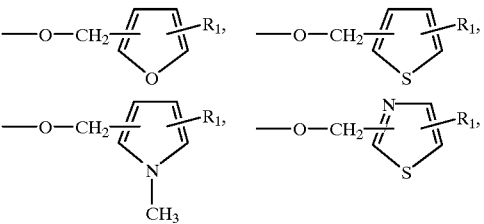

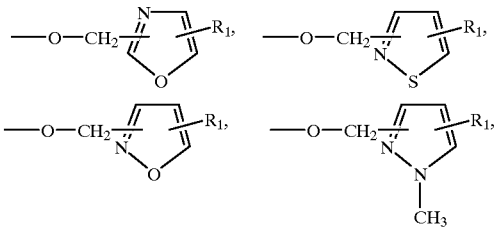

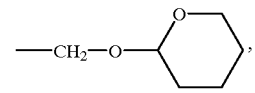

wherein R" is hydrogen, CH$_2$OH ,(C$_1$–C$_6$)alkyl, (C$_1$–C$_6$) alkyl-O—CH$_2$—, (C$_1$–C$_6$)alkyl-S—CH$_2$—, (C$_1$–C$_6$) alkyl-NH—CH$_2$—, [(C$_1$–C$_3$)alkyl]$_2$-NCH$_2$—, (C$_1$–C$_6$) cycloalkyl-O—CH$_2$—, [(C$_1$–C$_3$) alkyl]$_2$-N—(CH$_2$)$_{2-4}$NHCH$_2$—, [(C$_1$–C$_3$) alkyl]$_2$-N—(CH$_2$)$_{2-4}$N(CH$_3$)CH$_2$—,

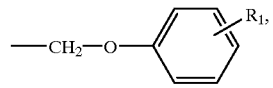

-continued

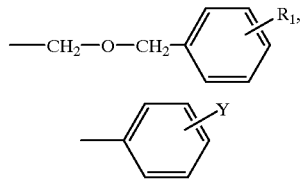

$R_1$ and $R_2$ are each, independently hydrogen or $CH_3$ $R_3$ is $(C_1-C_3)$ alkyl$SO_2$-Aryl $(CH_2)_nSO_2$—, Heteroary $(CH_2)_nSO_2$—, or $(C_1-C_3)$ alkyl-O—$(CH_2)_nSO_2$—, wherein m=1 to 3; n=0 to 3;

Aryl is

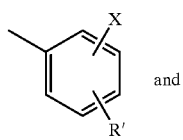 and

Heteroaryl is

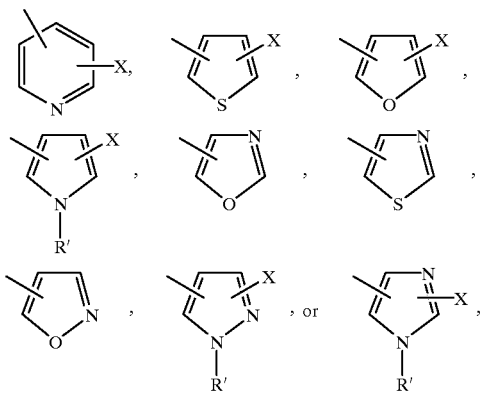

wherein X is hydrogen, halogen, $(C_1-C_3)$ alkyl or —$OCH_3$ and R and R' are as defined above; and pharmaceutically acceptable salts thereof.

It is more preferred that the compounds of the present invention include those of formula 1 wherein R is hydrogen, $(C_1-C_3)$ alkyl,—CN,—OR,—SR,—CF$_3$,OCF$_3$,Cl, F, NH$_2$, NH $(C_1-C_3)$ alkyl, —N(R')CO($C_1-C_3$)alkyl, —N(R')(R'), NO$_2$,—CONH$_2$,—SO$_2$NH$_2$, —SO$_2$NH$_2$, SO$_2$N(R')(R') or —N(R') COCH$_2$O—($C_1-C_3$) alkyl, wherein R' is ($C_1-C_3$) alkyl or hydrogen;

$R_4$ is $(C_1-C_6)$ alkyl-O— containing one triple bond

A further, more preferred embodiment of the present invention includes compounds represented by formula 1 wherein R is selected from hydrogen, $(C_1-C_3)$ alkyl, —CN, —OR', —SR', —CF$_3$, —OCF$_3$, Cl, F, NH$_2$, NH($C_1-C_3$) alkyl, —N(R')CO($C_1-C_3$)alkyl, —N(R')(R'), NO$_2$, —CONH$_2$, —SO$_2$NH$_2$, —SO$_2$N(R')(R'), or —N(R') COCH$_2$O—($C_1-C_3$)alkyl, wherein R' is ($C_1-C_3$) alkyl or hydrogen;

$R_4$ is $(C_1-C_6)$alkyl-O— containing one triple bond,

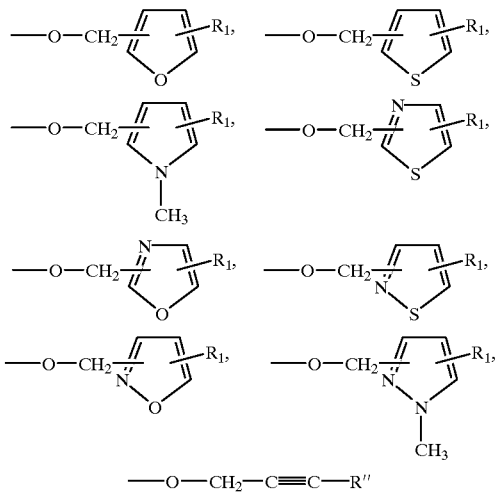

wherein R" is hydrogen, —CH$_2$OH, ($C_1-C_6$)alkyl, ($C_1-C_6$)alkyl-O—CH$_2$—, ($C_1-C_6$)alkyl-S—CH$_2$—, ($C_1-C_6$)alkyl-NH—CH$_2$—, [($C_1-C_3$)alkyl]$_2$-NCH$_2$—, ($C_1-C_6$)cycloalkyl-O—CH$_2$—, [($C_1-C_3$)alkyl]$_2$-N—(CH$_2$)$_{2-4}$NHCH$_2$—, [($C_1-C_3$)alkyl]$_2$-N—(CH$_2$)$_{2-4}$N(CH$_3$)CH$_2$—,

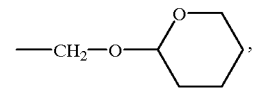

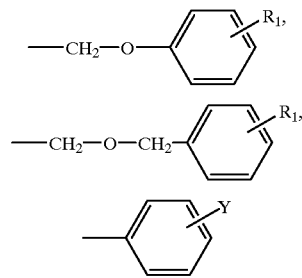

$R_1$ and $R_2$ are each, independently hydrogen or $CH_3$; $R_3$ is ($C_1-C_3$) alkylCO—, ($C_1-C_3$)alkyl-CO—, ($C_1-C_7$) cycloalkyCO—, ($C_1-C_3$)alkyl-O—(CH$_2$)$_m$—CO—, Ar (CH$_2$)$_n$CO—, HO—(CH$_2$)$_m$CO—, Heteroaryl(CH$_2$)$_m$—CO— wherein

Aryl is

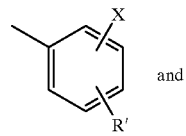 and

Heteroaryl is

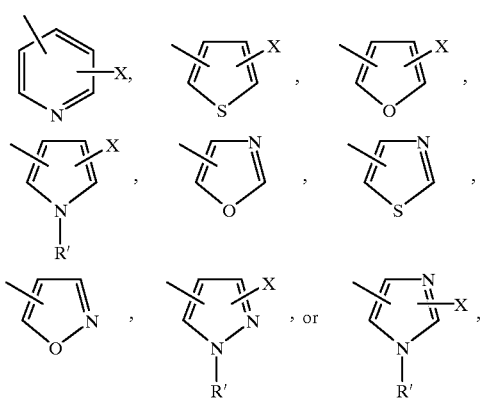

wherein X is hydrogen, halogen, (C₁–C₃) alkyl or —OCH₃ and R and R' are as defined above; and pharmaceutically acceptable salts thereof.

Additionally highly preferred compounds of the present invention include those of formula 1 wherein R is hydrogen, (C₁–C₃) alkyl, —CN, —OR', —SR', —CF₃—OCF₃, Cl, F, NH₂, NH(C₁–C₃)alkyl, —N(R')CO(C₁–C₃)alkyl, —N(R')(R'), NO₂, —CONH₂, —SO₂NH₂, —SO₂N(R')(R'), or —N(R')COCH₂O—(C₁–C₃)alkyl, wherein R' is (C₁–C₃) alkyl or hydrogen;

R₄ is —O—CH₂—C≡C—R'';
  wherein R'' is hydrogen, —CH₂OH, (C₁–C₆)alkyl, (C₁–C₆)alkyl-O—CH₂—, (C₁–C₆)alkyl-S—CH₂—, (C₁–C₆)alkyl-NH—CH₂—, [(C₁–C₃)alkyl]₂-NCH₂—, (C₁–C₆)cycloalkyl-O—CH₂—, [(C₁–C₃) alkyl]₂-N—(CH₂)₂₋₄NHCH₂—, [(C₁–C₃) alkyl]₂-N—(CH₂)₂₋₄N(CH₃)CH₂—,

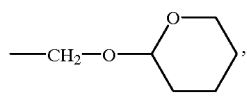

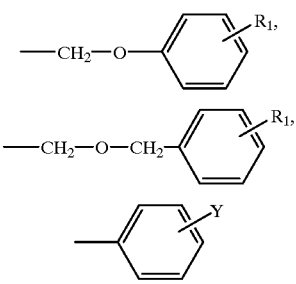

R₁ and R₂ are each, independently hydrogen or CH₃;
R₃ is

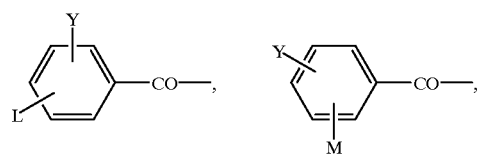

-continued

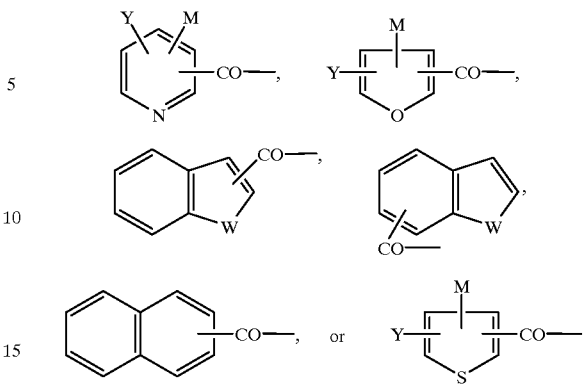

wherein m=1 to 3; n=0 to 3;

L is hydrogen, (C₁–C₃)alkyl, —CN, —OR', —SR', —CF₃, —OCF₃, Cl, F, NH₂, —NH—(C₁–C₃)alkyl, N(R')CO(C₁–C₃)alkyl, N(R')(R'), —NO₂, —CONH₂, —SO₂NH₂, —SO₂N(R')(R'), —N(R')COCH₂O—(C₁–C₃)alkyl,

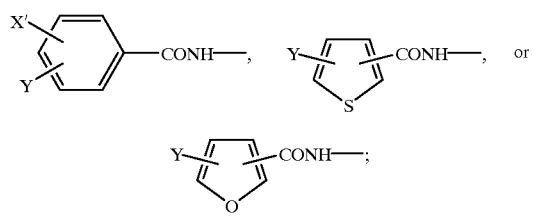

M is

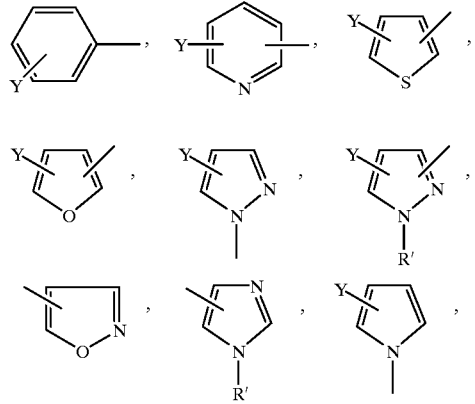

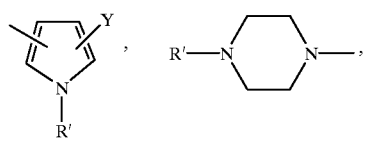

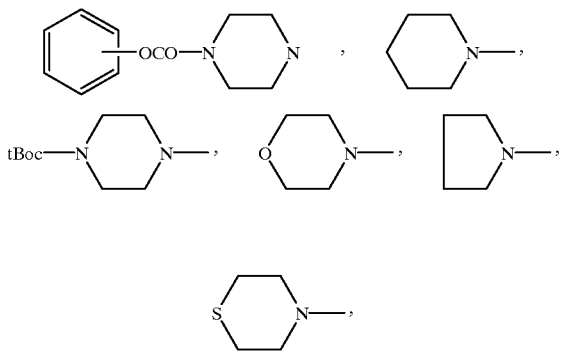

or N(R')(R') where R' is as defined above;

W is O, S, NH or N($C_1$–$C_3$)alkyl;

Y is hydrogen, F, Cl, $CF_3$ or $OCH_3$; and X' is halogen, hydrogen, ($C_1$–$C_3$)alkyl, O—($C_1$–$C_3$)alkyl, or —$CH_2OH$; and pharmaceutically acceptable salts thereof.

Some of the intermediate compounds for the preparation of derivatives of formula 1 are those wherein $R_4$ is $OCH_3$ and they may be advantageously prepared according to the illustrated Reaction Schemes. Ester derivatives of formulae 8,14, 15,20,22,23,24,25,29 and 30 wherein $R_4$ is $OCH_3$ are used to prepare derivatives wherein $R_4$ is OH (via cleavage of O—$CH_3$ group). As illustrated in Scheme 8 derivatives 40 with a phenolic OH group are reacted under standard organic synthetic conditions to convert the OH moiety into the $R_4$ substituents (as previously defined). Variations in these schemes may be made to improve productivity without negatively impacting the amount and nature of the product, by means that will be recognized by those skilled in the art. For example, reactive groups may be blocked with suitable blocking moieties which may then be deblocked under standard conditions (for instance, hydroxy groups may be protected with trimethylsilyl or t-butyl-dimethylsilyl moieties which are then removed in a later reaction step). In addition, those skilled in the art will recognize that catalylic hydrogenation conditions are inappropiate for preparing intermediates with an $R_4$ moiety containing a triple bond; the $R_4$ moiety is then introduced into intermediates not requiring a reduction step.

In general, the compounds of Formula 1 are synthesized from an alkyl ester (such as methyl, ethyl, t-butyl and the like) of serine, threonine, or 3,3-dimethyl-3-hydroxypropionic acids. One reaction pathway is shown in Reaction Scheme 1. It is noted that methyl esters are shown in all of the Reaction Schemes, however, it is to be understood that the use of methyl esters is for purposes of illustration only, and other suitable alkyl esters. benzyl esters and the like may similarly be used.

In Reaction Scheme 1, serine, threonine, beta-hydroxyvaline and related derivatives are converted to the corresponding N-(4-substituted-benzenesulfonyl) derivatives 3 and alkylated with suitable substituted or unsubstituted 2-nitrobenzyl bromides or 2-nitrobenzyl chlorides to provide the corresponding nitro derivatives 5 . Reduction under conventional reducing conditions, such as catalytic hydrogenation (with Pd/C) or chemical reduction (e.g., with $SnCl_2$ or $FeCl_3$) results in amino derivatives 6. Reaction of the N-(2-aminobenzyl) derivatives 6 with alkanoyl chlorides, alkylsulfonyl chlorides, aroyl chlorides, heteroaroyl chlorides, aryl sulfonyl chlorides, heteroarylsulfonyl chlorides and the like, in the presence of trialkylamines or pyridene, provides the dehydroalanine derivatives 7. Ring closure to the [1,4]benzodiazepine compounds 9 is carried out by reaction with a mild base such as sodium or potassium bicarbonate in an alcohol solvent such as methanol or ethanol. Standard conditions which involve hydrolysis of the ester (NaOH), acid chloride formation and reaction of the acid chloride with hydroxylamine are then used to convert the ester derivatives 8 to the hydroxamic acids 9. Ester derivatives 8 (where the ester function is a t-butyl ester) are converted to the acid with trifluoroacetic acid under standard conditions.

As illustrated in Reaction Scheme 2, derivatives 10, which contain a blocked hydroxyl group, are alkylated with 2-nitro or 2-amino benzyl alcohol derivatives 11 by application of the Mitsunobu reaction to give intermediates 12. Reduction of the 2-nitro group and removal of the hydroxy blocking group with derivatives 12, where the $R_4$ group is a protected amino moiety with simultaneous deblocking of the amino and hydroxyl functions, gives intermediate compounds 13. The intermediates 13 may then be reacted with benzyloxycarbonyl chloride to give the closed ring [1,4]benzodiazepines 14. Reaction of the derivatives 14 with acyl chlorides, aroyl chlorides, heteroaroyl chlorides, alkysulfonyl chlorides, arylsulfonyl chlorides and heteroarylsulfonyl chlorides and the like affords the intermediates 15.

Scheme 1

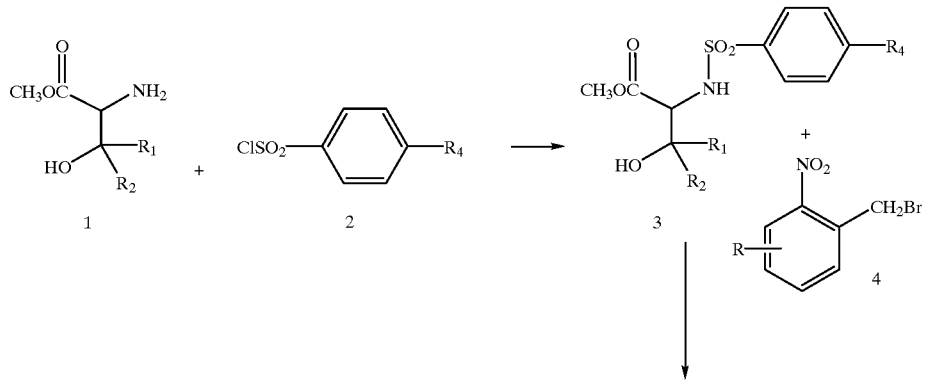

-continued

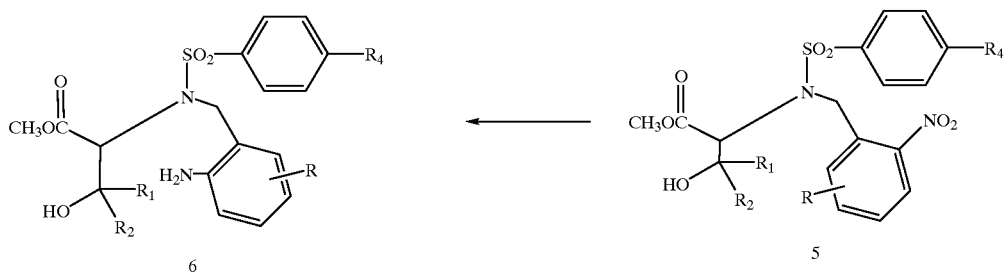

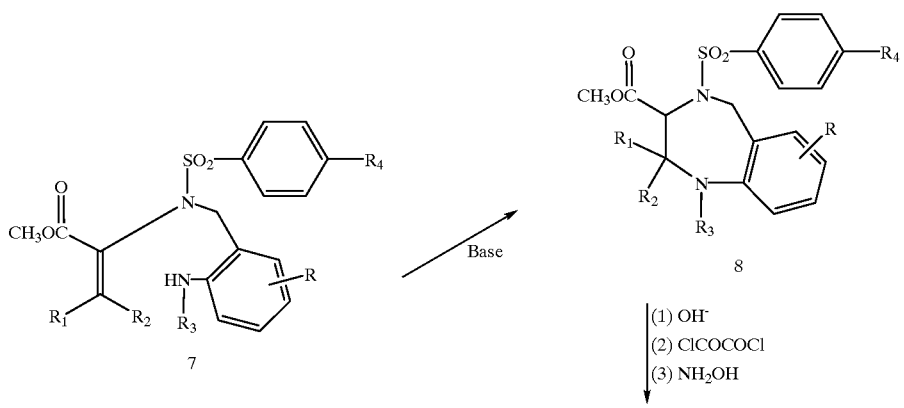

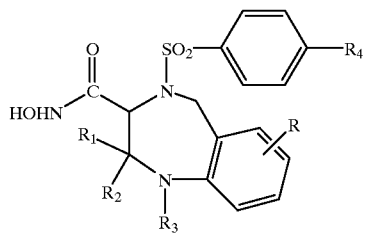

wherein
n=0 to 3;
m=1 to 3;
$R_1$ and $R_2$ are independently hydrogen or $(C_1-C_3)$alkyl;
R=Hydrogen; halogen; $OCH_3$; $NO_2$; $NH_2$; $CF_3$; $NHCOCH_3$; $NHCOCH_2CH_3$; $CONH_2$; —N(R')(R'), —N(R')CO($C_1-C_3$)alkyl; $(C_1-C_3)$alkyl;

$R_3$=Ar$(CH_2)_n$CO—; Heteroaryl$(CH_2)_n$CO—, Ar$(CH_2)_n$SO$_2$—; Heteroaryl$(CH_2)_n$SO$_2$—; Alkyl-O—$CH_2)_n$CO—; Alkyl-O—$(CH_2)_m$SO$_2$—; AlkylCO—; AlkylSO$_2$—; AlkylCO—NHCH$_2$CO—; and cycloalkyl $(C_3-C_7)$CO—; and $R_4$ is as defined herein.

Scheme 2

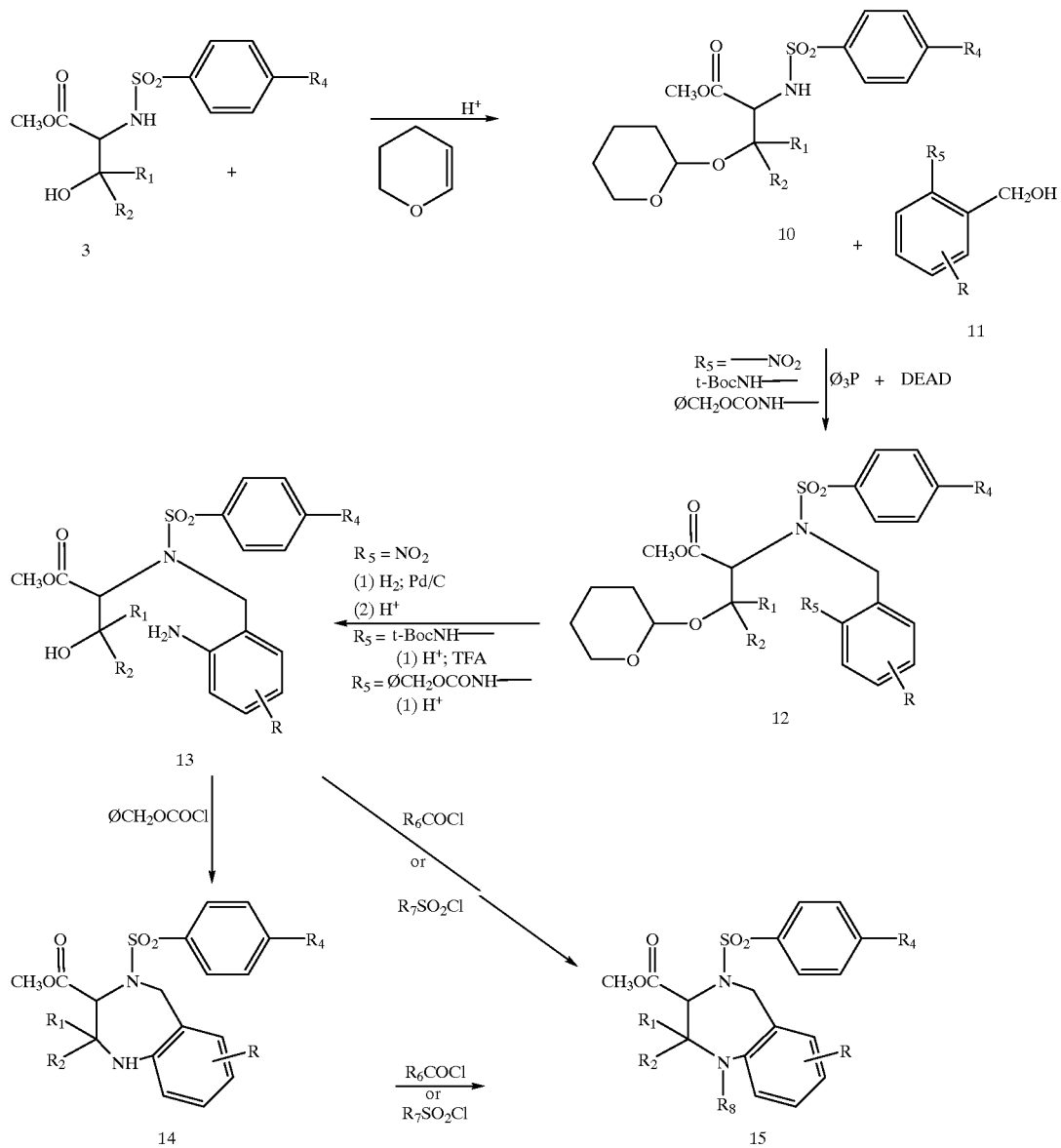

wherein
n=0 to 3;
m=1 to 3;
Ø=phenyl;
DEAD=diethylazodicarboxylate;
$R_6$=Ar$(CH_2)_n$—; Alkyl-; Heteroaryl$(CH_2)_n$—; Alkyl-O—$(CH_2)_n$—; Cycloalkyl$(C_3-C_7)$;
$R_7$=Ar$(CH_2)_n$—; Alkyl-; Heteroaryl$(CH_2)_n$—; Alkyl-O—$(CH_2)_m$—;
$R_8$=Ar$(CH_2)_n$CO—; Ar$(CH_2)_n$SO$_2$—; AlkylCO—; AlkylSO$_2$—; Heteroaryl$(CH_2)_n$CO—; Heteroaryl$(CH_2)_n$SO$_2$—; Alkyl-O—$(CH_2)_n$CO—; Alkyl-O—$(CH_2)_m$SO$_2$—.

1-substituted arylmethyl-2,3,4,5-tetrahydro-1H [1,4]-benzodiazepines may be prepared in the manner illustrated in Reaction Schemes 3 and 4. In Reaction Scheme 3, the methyl 3-hydroxy-2-[4-methoxybenzenesulfonyl)-(2-amino-benzyl)amino]- propionates 6 are subjected to reductive alkylation with arylcarboxaldehydes and heteroarylcarboxaldehydes to provide intermediates 17. Standard reaction conditions such as reactions with triphenylphosphine and diethyl azodicarboxylate (DEAD) or triplenylphosphine with either carbon tetrachloride or carbon tetrabromide, results in the "dehydroalanine" derivatives 18 which are then ring closed to the [1,4]benzodiazepines 20.

In an alternative route to the 3-hydroxamic acid derivatives 21 (Scheme 4), N-aroyl derivatives 22 are reduced with reducing agents such as borane or lithium aluminum hydride to reduce both the ester and amide functions. The 3-(hydroxymethyl)-1-(arylmethyl)-2,3,4,5-tetrahydro-1H-[1,4]benzodiazepines 23 are oxidized with standard reagents known to convert a hydroxymethyl group to a carboxylic acid:reagents such as NaIO$_4$ with catalyst RuO$_2$ (e.g., see J. Org. Chem., 46:3936 (1981); Synlett, p. 143, (1996)). Coupling the acids (via the acid chlorides) to hydroxylamine then gives products 21. Certain intermediates as exemplified by formula 25 may be reduced with borane under mild conditions to give derivatives 25a in which the amide carbonyl is selectively reduced. These intermediates 25a are then converted to hydroxamic acid derivatives via hydrolysis of the ester to the acid and coupling the acid chloride with hydroxylamine.
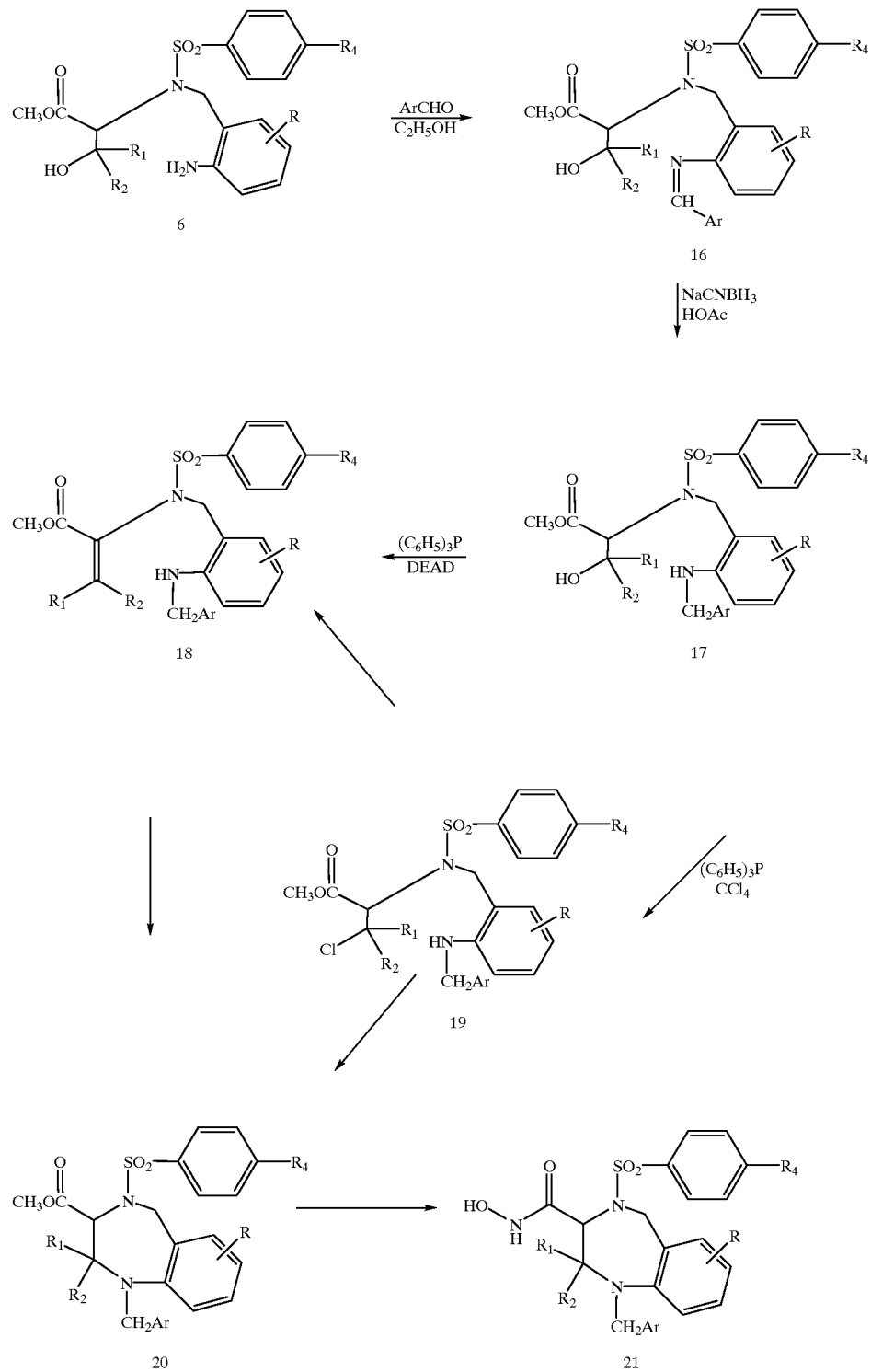
Scheme 3 wherein
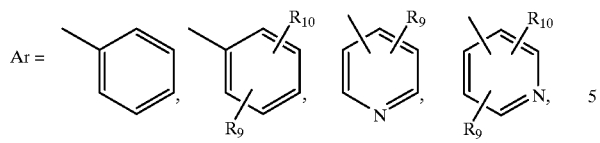
$R_9$ and $R_{10}$ are: Cl, Br, F, $OCH_3$, OEt, $SCH_3$,
$\overset{O}{\overset{\|}{C}}OCH_3$,
$\overset{O}{\overset{\|}{C}}OEt$,
$CF_3$, $OCF_3$,
$\overset{O}{\overset{\|}{C}}NH_2$,
—$NHCOCH_3$, or $Me_2N$—.
Scheme 4
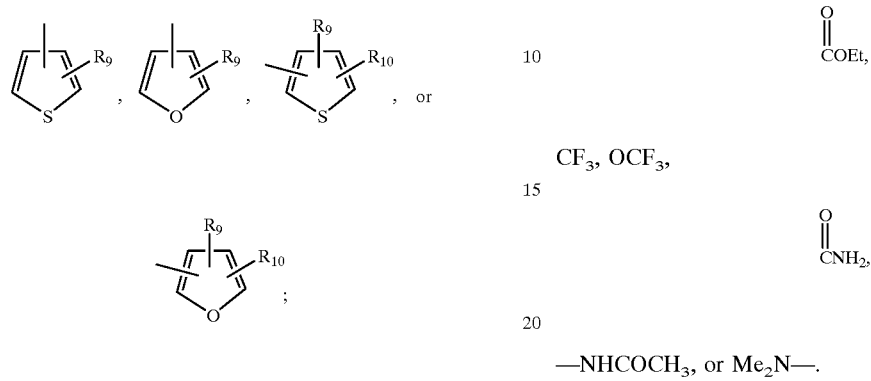
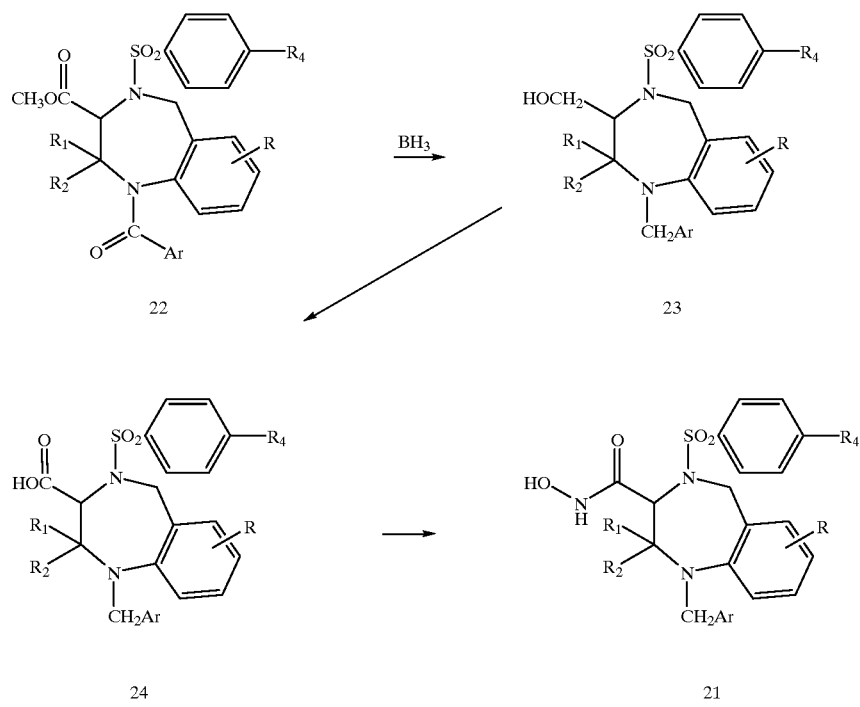
wherein
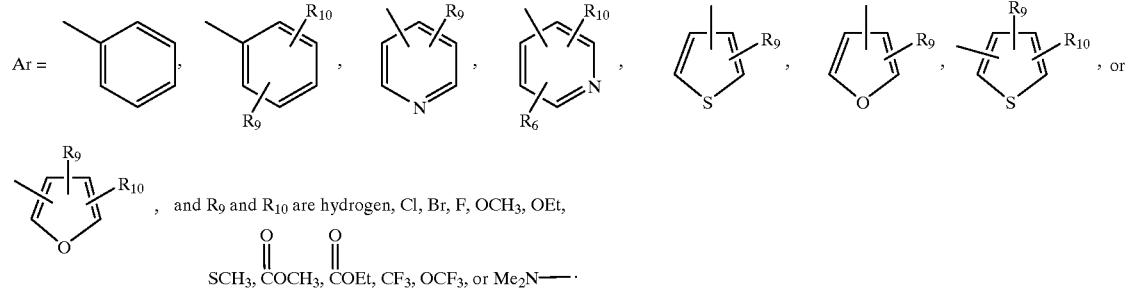
, and $R_9$ and $R_{10}$ are hydrogen, Cl, Br, F, $OCH_3$, OEt, $SCH_3$, $\overset{O}{\overset{\|}{C}}OCH_3$, $\overset{O}{\overset{\|}{C}}OEt$, $CF_3$, $OCF_3$, or $Me_2N$—.

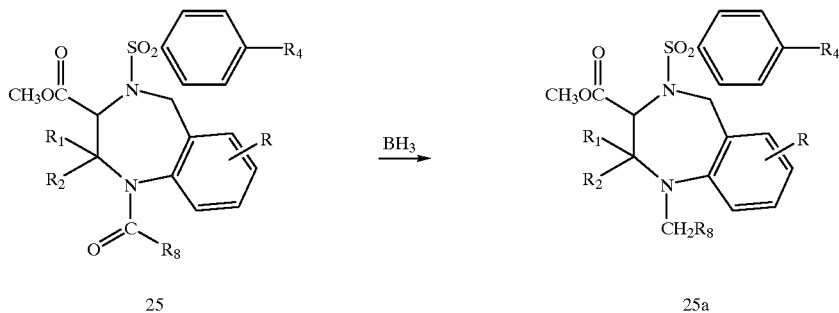

wherein R$_8$=alkyl, arylalkyl, aryloxyalkyl, heterocyclicalkyl, or alkyloxyalkyloxyalkyl.

Other, preferred compounds of the present invention are those with basic moieties in the 1-(substituted carbonyl) group which may be prepared in the manner shown in Reaction Scheme 5. Reaction of the 2,3,4,5-tetrahydro-1H-[1,4]-benzodiazepines 14 (without a substituent at the 1-position) with carbonyl chloride derivatives in the manner depicted in Reaction Scheme 5, results in intermediates 25 which are then converted to acid 26 and hydroxamic acids 27. The intermediates 25 may also be synthesized by reaction of methyl 2-[(2-aminobenzyl)-(4-methoxybenzenesulfonyl)amino]-3-hydroxypropionates 6 with acid chlorides to give "dehydroalanine" derivatives 28. As previously described, mild bases such as NaHCO$_3$ can be reacted with these derivatives to cause ring closure via a 1,4-addition to the double bond in intermediate 28 to provide the 7-membered 2,3,4,5-tetrahydro-1H-[1,4] diazepines 25.

As illustrated in Reaction Scheme 6, aryl-arylcarbonyl, heteroarylarylcarbonyl, aryl-heteroarylcarbonyl, heteroaryl-heteroarylcarbonyl derivatives 30 may be synthesized by standard palladium catalysed coupling of bromoaroyl or bromheteroaroyl derivatives 29 with appropriate arylstannanes, heteroarylstannanes, arylboronic acids, heteroarylboronic acids, aryl triflates, heteroaryl triflates and the like, under known conditions. For example, see *Synthesis*, 563–566 (1997); *J. Org. Chem.*, 62:3405–3406, (1997); *Tetrahedron Lett.*, 36:5247–5250, (1995); *Heterocycles*, 45:467, (1997); *Tetrahedron Lett.*, 38:1118–1182, (1997); *Heterocycles*, 42:189–194, (1996); *Tetrahedron Lett.*, 5005–5006, (1993); *Synthesis*, 843, (1987); *Heterocycles*, 2711–2716, (1987); and *Tetrahedron Lett.*, 4407–4410, (1986).

By coupling with such palladium catalysts, aryl-aryl, heteroaryl-aryl, aryl-heteroaryl and heteroaryl-heteroaryl carboxylic ester derivatives can be prepared and these derivatives converted to carboxylic acid intermediates. The acids are then converted to acid chlorides which are reacted with esters of 2-[(2-aminobenzyl)-(4-substituted-benzenesulfonyl)amino]-3-hydroxypropionate as illustrated for conversion of derivatives 6 to intermediates 31.

The following references describe procedures for the synthesis of methyl 3-arylpyrrole-4-carboxylates as in *J. Org. Chem.*, 62:2649–2651, (1997); methyl (2-methylphenyl) benzoates as in *J. Org. Chem.*, 62:3405–3406, (1997); and methyl benzoates substituted with heterocyclic moieties such as furanyl, thienyl or pyridinyl groups as in *Tetrahedron Lett.*, 27:4407–4410, (1986).

Scheme 5

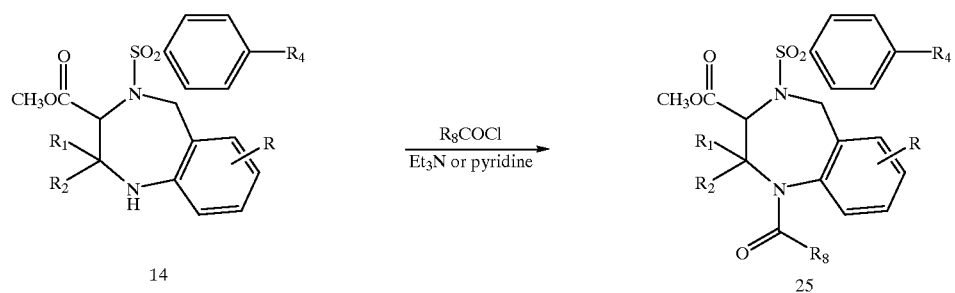

Wherein R$_8$ =
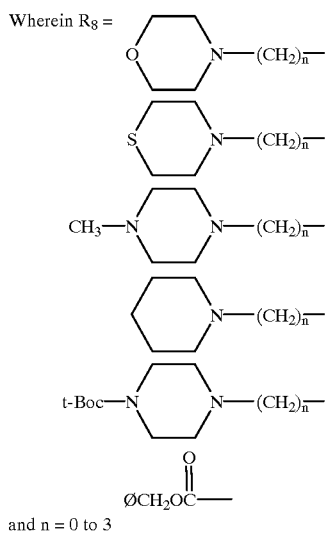
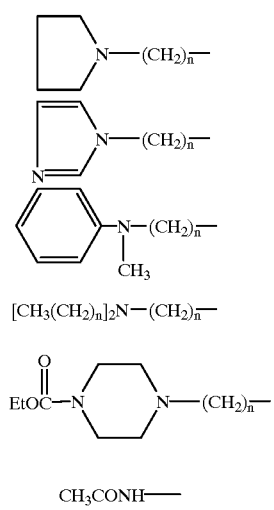
and n = 0 to 3
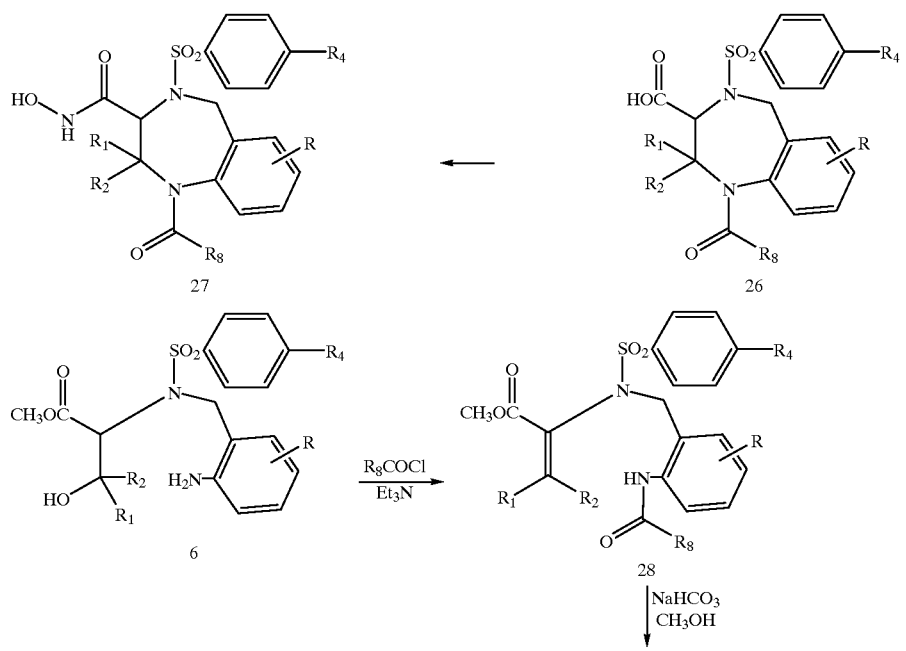
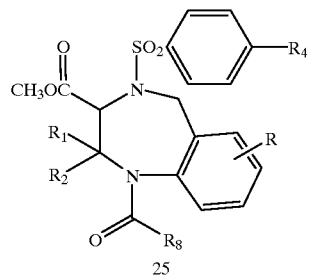

X is halogen, hydrogen, or $(C_1-C_3)$alkyl;
R and R' are as defined herein; and
$R_4$ is as defined herein.
Scheme 6
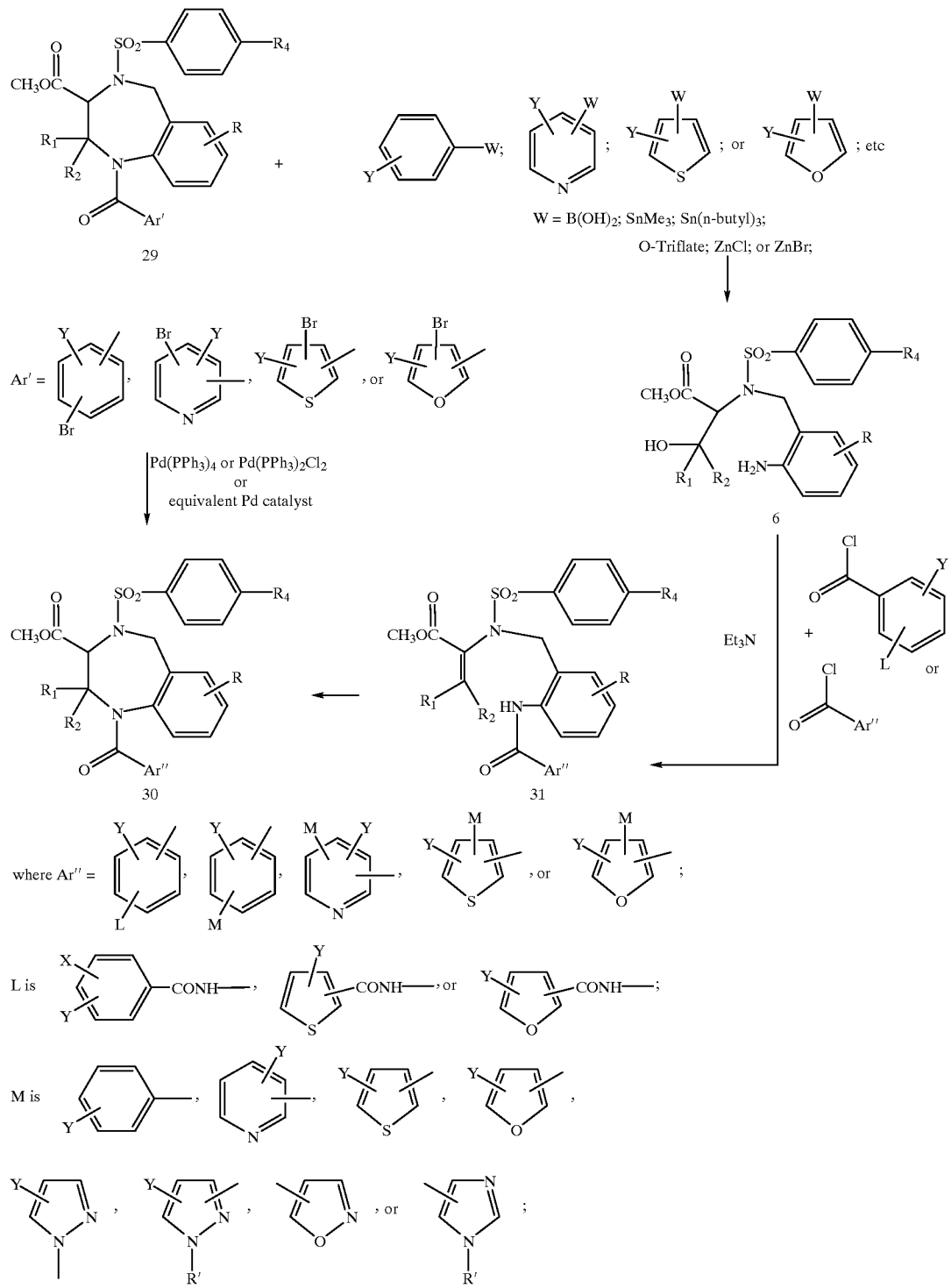
Y is H, F, Cl, $CF_3$, $CH_3$, or $OCH_3$;
X is halogen, hydrogen, or $(C_1-C_3)$alkyl;
R and R' are as defined herein; and
$R_4$ is as defined herein.

The intermediates 2,4,5,6-tetrahydro-1H-[1,4] benzodiazepines 39 and 38 may be prepared from glycine esters in the manner exemplified in Reaction Scheme 7. In this synthetic route, N-(4-substituted-benzenesulfonyl) derivatives of glycine ethyl ester, glycine t-butyl ester or glycine methyl ester 33 are alkylated with a substituted (R) or unsubstituted (R=H) 2-nitrobenzyl bromide in N,N-dimethylformamide or 1-methyl-2-pyrrolidinone in the presence of potassium carbonate to give intermediates 34. Alternatively, the esters of N-(4-substituted-benzenesulfonyl) glycines, such as the methyl ester 33, are first reacted with sodium hydride in N,N-dimethylformamide or 1-methyl-2-pyrrolidinone and the resulting anion reacted with substituted or unsubstituted 2-nitrobenzylbromides to provide compounds 34. Reaction of derivates 34 with N,N-dimethyl(methylene)ammonium chloride or the iodide salts under standard reaction conditions (e.g., as set forth in *Fieser and Fieser,* 10:160–161; 8:194 affords the dimethylaminomethyl (Mannich type) compounds as intermediates for elimination to the "dehydroalanine" derivatives 37 or direct ring closure of 36 to 39 via an elimination-addition reaction. Ring closure of compounds 37 provides intermediates 38 for conversion to hydroxamic acids. Variations of the reactions conditions for conversion of 36 to 39 involve heating in the presence of Lewis acids, such as $BF_3$, or heating an acid salt of 36 to effect the elimination-addition reaction.

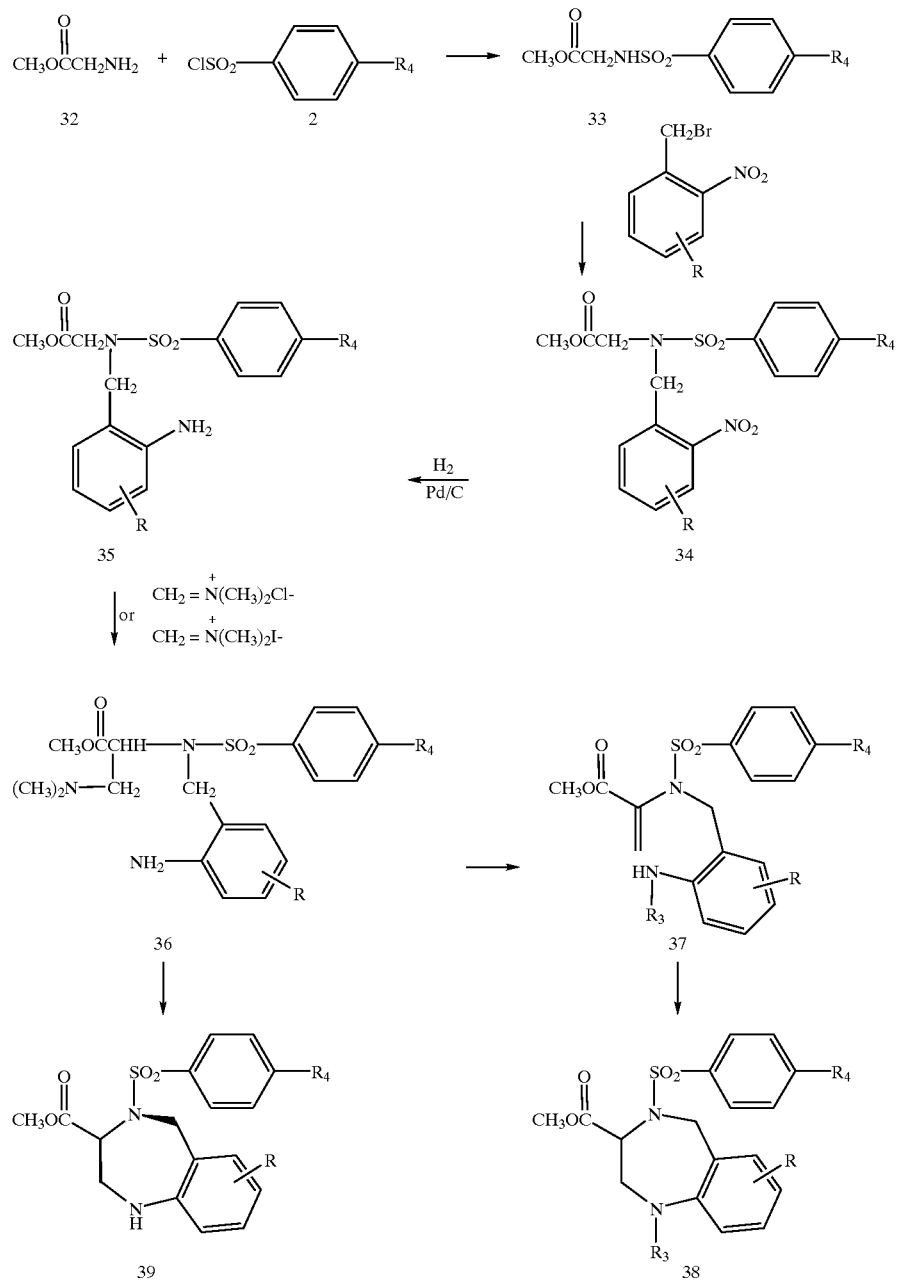

Scheme 7

The intermediate carboxylic acids for conversion to the tetrahydro[1,4]benzodiazepine-3-carboxylic acid, hydroxyamides may be synthesized via different routes as shown in Schemes 1–8. For the synthesis of some of the desired products of Formula 1, alternate routes are preferred as shown in Scheme 8. These routes may be preferred when the $R_4$ group contains a triple bond or when it is preferred to introduce the $R_4$ group toward the end of the synthetic sequence. Under these conditions, intermediate carboxylate esters of formula 41 or acids of formula 44 wherein the $R_4$ substituent is an OH group are prepared. Intermediates with $R_4$ an OH group any be prepared from derivatives wherein the OH group is protected by a group which can be selectively removed. Derivatives 40 wherein $R_4$ is an $OCH_3$ moiety are suitable precurssors to the desired phenolic compounds 41 and 44 through cleavage of the oxygen methyl bond. As shown in Scheme 8 the anion of the phenolic OH group may be prepared in situ and then alkylated. Suitable bases are alkaline metal carbonates, hydrides, alkoxides and organic bases. Reaction with an alkylating moiety represented by the formula $R_{15}CH_2X$ wherein X is a reactive leaving group such as a chloride, bromide, iodide, O-mesylate or an O-tosylate gives the derivatives 42 and 45.

The alkylation reaction may be carried out with carboxylate esters such as 41 or with the carboxylic acids represented by formula 44. Alternatively, the phenolic compounds 41 and 44 may be reacted under Mitsunobe Reaction conditions to afford the O-alkylated derivatives 42 and 45. Standard Mitsunobe Reaction conditions, which are described in the following literature references, may be used in the coupling reactions.

(a) J. Heterocyclic Chem. 34, 349 (1997);(b) Tetrahedron Lett 37, 6439 (1996);(c) J. Org Chem, 56, 7173 (1991);(d) Tetrahedron Lett 5709 (1989;(e) Synthesis 1–28 (1981).

Scheme 8

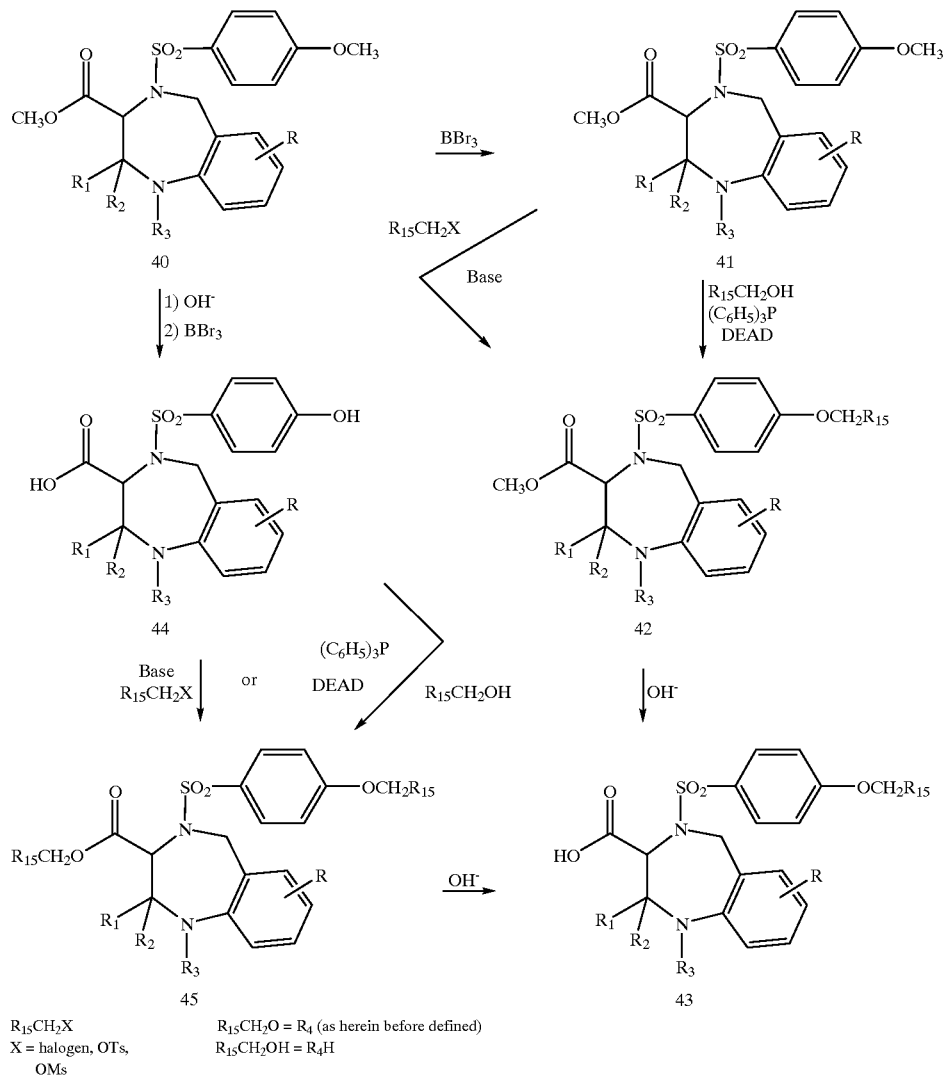

The compounds of the present invention which have a basic moiety may be used in the form of salts derived from pharmaceutically or physiologically acceptable acids. These salts include, but are not limited to, salts with inorganic acids (such as hydrochloric acid, sulfuric acid, nitric acid, phosphoric acid) or organic acids (such as acetic acid, oxalic acid, succinic acid, and maleic acid). Other salts of compounds with an acidic moiety include those with alkali metals or alkaline earth metals (such as sodium, potassium, calcium, and magnesium) or organic bases.

When the present compounds are utilized in pharmaceutical compositions, they may be combined with one or more pharmaceutically acceptable carriers, e.g., solvents, diluents and the like. Such compositions containing the present compounds may be administered orally, in the form of tablets, capsules, dispersible powders, granules, suspensions, syrups or elixirs; parentally, in the form of a sterile injectable solution or suspension; or topically, in the form of creams, lotions, ointments, etc. Such pharmaceutical compositions may contain from about 1 to about 100 mg of active ingredient in combination with the carrier.

The effective dosage of the present compounds utilized to treat a specific condition will vary depending upon the particular compound employed, the mode of administration and the type and severity of the condition being treated. However, in general, satisfactory results are obtained when the present compounds are administered at a dosage of about 0.001 to 1000 mg/kg of body weight.

As noted above, the compounds of the present invention may be administered orally, as well as by intravenous, intramuscular, subcutaneous or topical routes. Solid carriers useful for preparing tablets, capsules, etc., include starch, lactose, dicalcium phosphate, microcrystalline cellulose, sucrose and kaolin. Liquid carriers useful for preparing compositions of the present compounds include sterile water, polyethylene, glycols, non-ionic surfactants, and edible oils such as corn, sesame, and peanut oils. Adjuvants conventionally used in the preparation of pharmaceutical compositions may also be included, such as flavoring agents, coloring agents, preservatives and antioxidants.

The compounds of the present invention were tested for biological activity according to the following procedures.

In Vitro Gelatinase Assay

The assay is based on the cleavage of the thiopeptide substrate ((Ac-Pro-Leu-Gly(2-mercapto-4-methylpentanoyl)-Leu-Gly-OEt), available from Bachem Bioscience) by the enzyme gelatinase, releasing the substrate product which reacts calorimetrically with DTNB ((5,5'-dithio-bis(2-nitro-benzoic acid)). This assay is disclosed in Weingarten et al., "Spectrophotometric Assay for Vertebrate Collegenase", Anal. Biochem., 147:437–440, (1985). The enzyme activity is measured by the rate of the color increase.

The thiopeptide substrate was made up fresh as a 20 mM stock in 100% DMSO and the DTNB was dissolved in 100% DMSO as a 100 mM stock and stored in the dark at room temperature. The substrate and the DTNB were diluted together to 1 mM with substrate buffer (50 mM HEPES, pH 7.5, 5 mM $CaCl_2$) before use. The stock of human neutrophil gelatinase B was diluted with assay buffer (50 mM HEPES, pH 7.5, 5 mM $CaCl_2$, 0.02% Brij) to a final concentration of 0.15 nM.

The assay buffer, enzyme, DTNB/substrate (500 μM final concentration) and vehicle or inhibitor were added to a 96 well plate (total reaction volume of 200 μl) and the increase in color was monitored spectrophotometrically for 5 minutes at 405 nm on a plate reader.

The increase in $OD_{405}$ was plotted and the slope of the line was calculated. The slope represents the reaction rate. The linearity of the reaction rate was confirmed ($r^2>0.85$) and the mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression (IPRED, HTB).

In Vitro Collagenase Assay

This assay was based on the cleavage of a peptide substrate ((Dnp-Pro-Cha-Gly-Cys(Me)-His-Ala-Lys(NMa)-$NH_2$), available from Peptide International, Inc.) by collagenase releasing the fluorescent NMa group which was quantitated on the fluorometer as disclosed in Bickett et al., "A High Throughput Fluorogenic Substrate for Interstitial Collagenase (MMP-1) and Gelatinase (MMP-9)", Anal. Biochem., 212:58–64, (1993). Dnp quenches the NMa fluorescence in the intact substrate.

The assay was run in HCBC assay buffer (50 mM HEPES, pH 7.0, 5 mM $Ca^{+2}$, 0.02% Brij, 0.5% Cysteine), with human recombinant fibroblast collagenase (truncated, mw=18,828, from Wyeth-Ayerst Research, Radnor, Pa.). The substrate was dissolved in methanol and stored frozen in 1 mM aliquots. Collagenase was stored frozen in buffer in 25 μM aliquots. In conducting the assay, the substrate was dissolved in HCBC buffer to a final concentration of 10 μM and collagenase to a final concentration of 5 nM. The compounds being examined were dissolved in methanol, DMSO, or HCBC. The methanol and DMSO were diluted in HCBC to <1.0%. The compounds were added to a 96 well plate containing enzyme and the reaction was started by the addition of substrate.

The reaction was read (excitation 340 nm, emission 444 nm) for 10 min. and the increase in fluorescence over time was plotted as a linear line. The slope of the line was calculated representing the reaction rate. The linearity of the reaction rate was confirmed ($r^2>0.85$). The mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression.

Procedure for Measuring TACE Inhibition

In a 96-well black microtiter plate, each well received a solution composed of 10 μL TACE (available from Immunex) at a final concentration of 1 μg/mL, 70 μL Tris buffer, have a pH of 7.4 and containing 10% glycerol (final concentration 10 mM), and 10 μL of test compound solution in DMSO (final concentration 1 μM, DMSO concentration <1%). The plates were incubated for 10 minutes at room temperature. The reaction was initiated by addition of a fluorescent peptidyl substrate (final concentration 100 μM) to each well with shaking on a shaker for 5 sec.

The reaction was read (excitation 340 nm, emission 420 nm) for 10 min. and the increase in fluorescence over time was plotted as a linear line. The slope of the line was calculated and this represents the reaction rate. The linearity of the reaction rate was confirmed ($r^2>0.85$). The mean (x±sem) of the control rate was calculated and compared for statistical significance (p<0.05) with drug-treated rates using Dunnett's multiple comparison test. Dose-response relationships were generated using multiple doses of drug and $IC_{50}$ values with 95% CI were estimated using linear regression.

Some results obtained following these standard experimental test procedures are present in Table 1.

TABLE 1

[Structure: benzodiazepine with HOHN-C(O)- group, R1, R2 substituents, N-R3, and N-SO2-phenyl-R4]

| R3 | Compound of Example | R | R1 | R2 | R4 | MMP-1 | MMP-9 | MMP-13 | TACE |
|---|---|---|---|---|---|---|---|---|---|
| —COCH3 | 1 | H | H | H | —OCH2C≡CCH3 | 835 | 228 | 77 | 16 |
| —CO-(2-thienyl) | 2 | H | H | H | —OCH2C≡CCH3 | 250 | 24 | 8 | 38 |
| —CO-phenyl | 3 | H | H | H | —OCH2C≡CCH3 | 165 | 36 | 10 | 59 |
| —CO-(2-furyl) | 57 | H | H | H | —OCH2C≡CCH3 | 125 | 2 | 7 | 33 |
| —CO-cyclopropyl | 58 | H | H | H | —OCH2C≡CCH3 | 841 | 33 | 29 | 10 |

IC$_{50}$ (nM)

Some intermediate compounds for the synthesis of derivatives of formula 1 are presented in Table 2 (Reference Examples 10,11,41,43–90,92–97,99,100,162,166,176,181,182,186,188,190)

TABLE 2

[Structure: benzodiazepine with CH3O-C(O)- group, R1, R2 substituents, N-R3, and N-SO2-phenyl-R4]

| R3 | R | R1 | R2 | R4 |
|---|---|---|---|---|
| —SO2-(4-methylphenyl) | H | R | H | —OCH3 |
| —SO2CH3 | H | H | H | —OCH3 |
| —SO2CH2CH2CH3 | H | H | H | —OCH3 |
| —SO2-(4-methoxyphenyl) | H | H | H | —OCH3 |

TABLE 2-continued
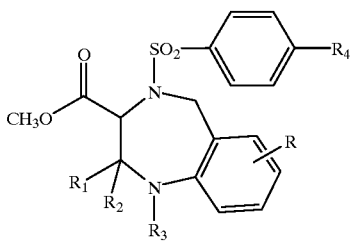
| R₃ | R | R₁ | R₂ | R₄ |
|---|---|---|---|---|
| —COCH₃ | H | H | H | —OCH₃ |
|  | H | H | H | —OCH₃ |
| —COCH₂OCH₃ | 7-CH₃ | H | H | —OCH₃ |
| 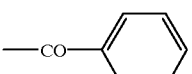 | 7-CH₃ | H | H | —OCH₃ |
|  | 8-Cl | H | H | —OCH₃ |
| —CH₂CH₂OCH₃ | H | H | H | —OCH₃ |
| 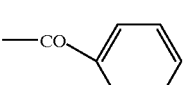 | 7-CH₃ | H | H | —OCH₃ |
| 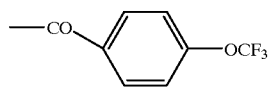 | 8-Cl | H | H | —OCH₃ |
| 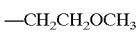 | H | H | H | —OCH₃ |
| 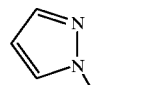 | H | H | H | —OCH₃ |
| 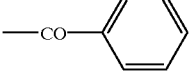 | H | H | H | —OCH₃ |

TABLE 2-continued
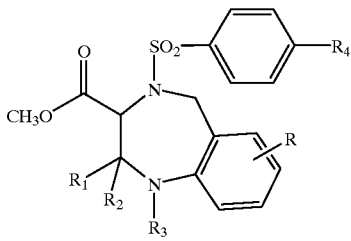
| R₃ | R | R₁ | R₂ | R₄ |
|---|---|---|---|---|
| 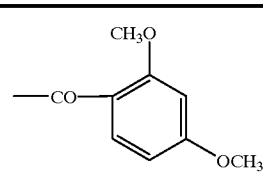 | H | H | H | —OCH₃ |
| 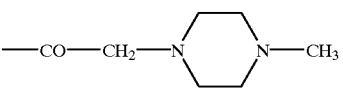 | H | H | H | OCH₃ |
| 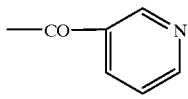 | H | H | H | —OCH₃ |
| 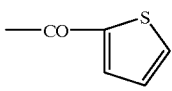 | H | H | H | —OCH₃ |
| 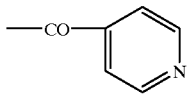 | H | H | H | —OCH₃ |
| COCH₂OCH₃ | H | H | H | —OCH₃ |
| 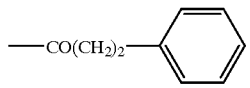 | H | H | H | —OCH₃ |
| 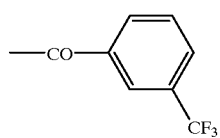 | H | H | H | —OCH₃ |
| 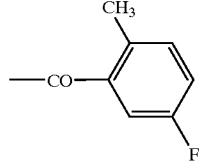 | H | H | H | —OCH₃ |
| 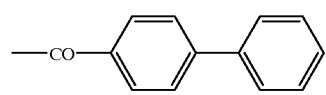 | H | H | H | —OCH₃ |

TABLE 2-continued

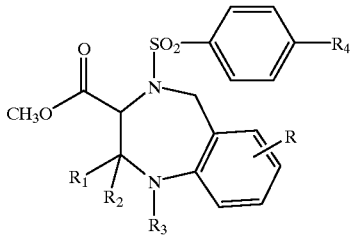

| $R_3$ | R | $R_1$ | $R_2$ | $R_4$ |
|---|---|---|---|---|
| 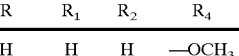 | H | H | H | —OCH$_3$ |
| 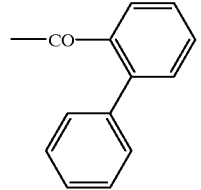 | H | H | H | —OCH$_3$ |
|  | H | H | H | —OCH$_3$ |
|  | H | H | H | —OCH$_3$ |
|  | H | H | H | —OCH$_3$ |
|  | H | H | H | —OCH$_3$ |

The present invention will now be illustrated with reference to the following, non-limiting examples.

REFERENCE EXAMPLE 1

(L) N-(Benzyloxycarbonyl)-O-benzylserine, t-butyl ester

Into a solution of 25 g (0.076 mol) of N-(benzyloxycarbonyl)-O-benzylserine in 600 ml of CH$_2$Cl$_2$ cooled to −6° C. in an ice-salt bath was bubbled isobutylene, while 4.1 ml of concentrated sulfuric acid was added dropwise thereto. The mixture was stirred for 4 hours and worked up as described in *Synthetic Commun.*, 26:2723 (1996) to give 29.24 g of product as a yellow oil.

REFERENCE EXAMPLE 2

L-Serine, t-butyl ester

A mixture of 29.24 g (0.076 mol) of (L) N-(benzyloxycarbonyl)-O-benzylserine, t-butyl ester from Reference Example 1, 24.1 g (0.38 mol) of ammonium formate and 38.3 g of 10% palladium on carbon in 600 ml of methanol was heated at 65° C. for 20 hours and stirred at room temperature overnight. The mixture was filtered through diatomaceous earth and the filter pad was washed with methanol. The filtrate was concentrated to give 12.18 g (99.6%) of product as described in *Synthetic Commun.*, 26:2723 (1996).

REFERENCE EXAMPLE 3

N-(4-Methoxybenzenesulfonyl)-L-serine, t-butyl ester (3-hydroxy-2-(4-methoxybenzenesulfonylamino)propionic acid, tert-butyl ester)

To a solution of 12.18 g (0.0756 mol) of L-serine, t-butyl ester, 26.52 ml of triethylamine in 160 ml of CH$_2$Cl$_2$ (cooled in an ice bath) was added, in small portions, 16.1 g (0.0771 mol) of 4-methoxybenzene-sulfonyl chloride. The mixture was stirred at 0° C. for 0.5 hours and at room temperature overnight. The mixture was washed with H$_2$O, 2N citric acid, brine and dried with $Na_2SO_4$. The solvent was removed under vacuum to give 25.34 g of solid which was triturated with hexane. The solid was recrystallized from 120 ml of toluene to give 12.18 g (48.7%) of product as a white solid. The filtrate was concentrated and the residue chromatographed on silica gel with hexane-ethyl acetate (7:3) as eluent to give 5.71 g (22.8%) of white solid. m.p. 70–75° C. Anal. for $C_{14}H_{21}NO_6S$: Calc'd: C, 50.7; H, 6.4; N, 4.2; Found: C, 50.4; H, 6.3; N, 4.4.

REFERENCE EXAMPLE 4

3-Hydroxy-2-[(4-methoxybenzenesulfonyl)-(2-nitrobenzyl)amino]propionic acid, tert-butyl ester To 6.16 g (18.6 mmol) of 3-hydroxy-2-(4-methoxybenzenesulfonylamino)-propionic acid tert-butyl ester in 50 ml of N,N-dimethylformamide, cooled in an ice bath, was added 0.781 g (19.5 mmol) of sodium hydride. After gas evolution ceased, a solution of 4.02 g (18.6 mmol) of 2-nitrobenzylbromide in 18 ml of N,N-dimethylformamide was added dropwise. The mixture was stirred under nitrogen at room temperature for 4 hours and 1.0 g of 2-nitrobenzyl bromide was added. The mixture was stirred at room temperature overnight and the solvent removed under vacuum. The residue was diluted with water and extracted with $CH_2Cl_2$. The organic extract was washed with $H_2O$, brine and dried with $Na_2SO_4$. The solvent was removed to give 11.2 g of solid which was chromatographed on silica gel with hexane-ethyl acetate (1:1) as eluent followed by hexane-ethyl acetate (35:65) as eluent. The fractions containing product were combined and the solvent was then removed to gave 7.7 g (89%) of solid. A sample from a 3 mmol run gave a gum. Anal. for $C_{21}H_{26}N_2O_8S$: Calc'd: C, 54.1; H, 5.6; N, 6.0; Found: C, 54.0; H, 5.7; N, 6.0.

REFERENCE EXAMPLE 5

2-[(2-Aminobenzyl)-(4-methoxybenzenesulfonyl)amino]-3-hydroxypropionic acid, tert-butyl ester A mixture of 0.60 g (1.28 mmol) of 3-hydroxy-2-[(4-methoxybenzenesulfonyl)-(2-nitrobenzyl)amino]propionic acid, tert-butyl ester and 1.45 g (6.45 mmol) of $SnCl_2.2H_2O$ in 20 ml of methanol was heated in an oil bath at 90° C. for 2 hours. The solvent was removed under vacuum and ethyl acetate added to the residue. The mixture was neutralized with saturated sodium bicarbonate solution and filtered through diatomaceous earth. The ethyl acetate layer was separated and washed with $H_2O$, brine and dried with $Na_2SO_4$. The solvent was removed under vacuum to give 0.30 g (53%) of a gum. Anal. for $C_{21}H_{28}N_2O_6S$: Calc'd: C, 57.8; H, 6.5; N, 6.4; Found: C, 57.8; H, 7.0; N, 6.2.

REFERENCE EXAMPLE 6

2-[(2-Aminobenzyl)-(4-methoxybenzenesulfonyl)amino]-3-hydroxypropionic acid

A solution of 0.75 g (1.72 mmol) of 2-[(2-aminobenzyl)-(4-methoxybenzenesulfonyl)amino]-3-hydroxypropionic acid, tert-butyl ester and 6 ml of trifluoroacetic acid in 6 ml of $CH_2Cl_2$ was stirred at room temperature for 3 hours and then concentrated to dryness under vacuum. To the residue was added $H_2O$, $CH_2Cl_2$ and 1N NaOH until the aqueous layer reached pH 8. The aqueous layer was then separated, acidified with 2 N citric acid and extracted with ethyl acetate. The extract was washed with $H_2O$, brine and dried $Na_2SO_4$. The solvent was removed under vacuum to give 0.35 g (54%) of a solid. Anal. for $C_{17}H_{20}N_2O_6S$: Calc'd: C, 53.7; H, 5.3; N, 7.4; Found: C, 53.0; H, 5.3; N, 6.9.

REFERENCE EXAMPLE 7

2-{(2-[3-(Trifluoromethylbenzoyl)aminobenzyl]-(4-methoxybenzenesulfonyl)amino}acrylic acid, tert-butyl ester A mixture of 0.431 g (1 mmol) of 2-[(2-amino-benzyl)-(4-methoxybenzenesulfonyl)amino]-3-hydroxy-propionic acid, tert-butyl ester, 0.474 g (2.2 mmol) of 3-(trifluoromethyl)benzoyl chloride and 1 ml of pyridine in 2 ml of $CH_2Cl_2$ was stirred at room temperature for 3.5 hours. The mixture was poured into $H_2O$ and extracted with $CH_2Cl_2$. The extract was washed with $H_2O$, 2 N citric acid, $H_2O$, 1 N $NaHCO_3$, brine and dried with $Na_2SO_4$. The solvent was removed to give 0.72 g of solid. The solid was dissolved in 2 ml of tetrahydrofuran and 1.5 ml of triethylamine was added thereto. The solution was heated at 65° C. overnight and concentrated to dryness under vacuum. The residue was extracted with $CH_2Cl_2$ and the extract washed with $H_2O$ and dried with $Na_2SO_4$. The solvent was removed under vacuum to give 0.55 g of product as a solid. From a similar run the product was chromatographed on silica gel with hexane-ethyl acetate to give a solid, m.p. 65–72° C. Anal. for $C_{29}H_{29}F_3N_2O_6S$: Calc'd: C, 59.0; H, 5.0; N, 4.7; Found: C, 59.2; H, 5.2; N, 4.4.

REFERENCE EXAMPLE 8

4-(4-Methoxybenzenesulfonyl)-1-(3-trifluoromethylbenzoyl)-2,3,4,5-tetrahydro-1H-[1,4]benzodiazepine-3-carboxylic acid, tert-butyl ester A mixture of 0.55 g (0.932 mmol) of 2-{(2-[3-(trifluoromethyl)benzoyl]-aminobenzoyl]-(4-methoxybenzenesulfonyl)amino} acrylic acid, tert-butyl ester and 0.102 g (1.21 mmol) of $NaHCO_3$ in 4 ml of methanol was stirred at room temperature overnight and the solvent removed. The residue was extracted with $CH_2Cl_2$ and the extract washed with $H_2O$, brine and dried with $Na_2SO_4$. The solvent was removed to give 0.57 g of solid. The solid was chromatographed on thick layer silica gel plates with hexane-ethyl acetate (1:1) as solvent to give 0.30 g of a light yellow solid, m.p. 57–60° C. Anal. for $C_{29}H_{29}F_3N_2O_6S$: Calc'd: C, 59.0; H, 5.0; N, 4.7; Found: C, 58.8; N, 5.0; N, 4.6.

REFERENCE EXAMPLE 9

4-(4-Methoxybenzenesulfonyl)-1-(3-trifluoromethylbenzoyl)-2,3,4,5-tetrahydro-1H-[1,4]benzodiazepine-3-carboxylic acid A mixture of 0.36 g (0.61 mmol) of 4-(4-methoxybenzenesulfonyl)-1-(3-trifluoromethylbenzoyl)-2,3,4,5-tetrahydro-1H-[1,4]benzodiazepine-3-carboxylic acid, tert-butyl ester and 3 ml of trifluoroacetic acid in 3 ml of $CH_2Cl_2$ was stirred at room temperature for 3 hours. The mixture was concentrated to dryness under vacuum and the residue extracted with $CH_2Cl_2$. The $CH_2Cl_2$ was washed with 1 N NaHCO$_3$ and the aqueous layer (pH 8) was acidified with 2 N citric acid and extracted with ethyl acetate. The extract was dried (Na$_2$SO$_4$). The original CH$_2$Cl$_2$ extract was washed with 2 N citric acid, H$_2$O, brine and dried with Na$_2$SO$_4$. The CH$_2$Cl$_2$ extract and the ethyl acetate extract were combined and the solvent removed under vacuum to give 0.31 g of solid, m.p. 105–110° C. Anal. for C$_{25}$H$_{21}$F$_3$N$_2$O$_6$S: Calc'd: C, 56.2; H, 4.0; N, 5.2; Found: C, 55.1; H, 3.7; N, 5.0.

REFERENCE EXAMPLE 10

Methyl 1-([1,1'-Biphenyl]-2-carbonyl)-4-(4-methoxybenzenesulfonyl)-2,3,4,5-tetrahydro-1H-[1,4]benzodiazepine-3-carboxylate To a mixture of 1.5 g (3.8 mmol) of methyl 2-[(2-aminobenzyl)-(4-methoxybenzenesulfonyl)amino]-3-hydroxypropionate and 2.65 ml of triethylamine in 12 ml of CH$_2$Cl$_2$ chilled at 0° C. was added a solution of [1,1'-biphenyl]-2-carbonyl chloride in 6 ml of CH$_2$Cl$_2$. The mixture was stirred at room temperature overnight and diluted with CH$_2$Cl$_2$ and H$_2$O. The organic layer was separated and washed with 2 N citric acid, brine and dried with Na$_2$SO$_4$. The solvent was removed under vacuum to give 2.2 g of a white foam. Anal. for C$_{31}$H$_{28}$N$_2$O$_6$S: Calc'd: C, 66.9; H, 5.1; N, 5.0; Found: C, 67.3; H, 5.2;N, 4.7.

REFERENCE EXAMPLE 11

Methyl 4-(4-Methoxybenzenesulfonyl)-1-(2-methyl-5-fluorobenzoyl)-2,3,4,5-tetrahydro-1H-[1,4]benzodiazepine-3-carboxylate To a mixture of 1.5 g (3.80 mmol) of methyl 2-[(2-aminobenzyl)-(4-methoxybenzenesulfonyl)amino]-3-hydroxypropionate and 2.64 ml (18.97 mmol) of triethylamine in 15 ml of CH$_2$Cl$_2$, chilled to 0° C., was added 1.36 g (11.4 mmol) of 2-methyl-5-fluorobenzoyl chloride. The mixture was stirred at room temperature overnight. The solution was then diluted with CH$_2$Cl$_2$ and water and the organic layer separated. The organic layer was washed with 2 N citric acid, brine and dried with Na$_2$SO$_4$. The solvent was removed under vacuum to give 2.2 g of a white foam. Anal. for C$_{26}$H$_{25}$FN$_2$O$_6$S: Calc'd: C, 60.9; H, 4.9; N, 5.5; Found: C, 60.9; H, 5.0; N, 5.0;

Mass spectrum (ES) 513.4 (M+H).

REFERENCE EXAMPLE 12

Methyl 4-(4-Methoxybenzenesulfonyl)-2,3,4,5-tetrahydro-1H-[1,4]benzodiazepine-3-carboxylate To a mixture of 5.0 g (12.68 mmol) of methyl 2-[(2-aminobenzyl)-(4-methoxybenzenesulfonyl)amino]-3-hydroxypropionate and 17.7 ml (26.8 mmol) of triethylamine in 50 ml of CH$_2$Cl$_2$ chilled to 0° C. was added 9.05 ml (63.4 mmol) of benzyl chloroformate. The mixture was stirred overnight and then cooled to 0° C. and 0.8 ml of triethylamine and 9.05 ml (63.4 mmol) of benzyl chloroformate were added thereto. The mixture was stirred overnight and then washed with H$_2$O, 2 N citric acid, brine and dried with Na$_2$SO$_4$. The solvent was removed under vacuum to give 6.95 g of solid. The solid was chromatographed on silica gel with hexane-ethyl acetate (1:1) to give 2.7 g of product as a viscous yellow oil. From a similar 0.5 g run, there was obtained 0.178 g of an oil. Anal. for C$_{18}$H$_{20}$N$_2$O$_5$S: Calc'd: C, 57.4; H, 5.4; N, 7.4; S, 8.5; Found: C, 57.9; H, 5.4; N, 6.7; S, 7.9;

Mass spectrum (ES) 377.2 (M+H).

REFERENCE EXAMPLE 13

Methyl 3-Hydroxy-2-(4-methoxybenzenesulfonylamino)propionate

To a mixture of 5.0 g (32.14 mmol) of D,L-serine, methyl ester and 15.7 ml (0.012 mol) of triethylamine in 100 ml of CH$_2$Cl$_2$, cooled to 0° C., was added portionwise 6.64 g (32.14 mmol) of 4-methoxybenzenesulfonyl chloride. The mixture was then stirred under argon at room temperature for 2 days. The mixture was diluted with 100 ml of CH$_2$Cl$_2$ and then washed with 60 ml each of H2O, 2 N citric acid, brine and dried with Na$_2$SO$_4$. The solvent was removed under vacuum to give a solid. Crystallization from ethyl acetate gave 5.0 g (54%) of white crystals, m.p. 92–94° C. Anal. for C$_{11}$H$_{15}$NO$_6$S: Calc'd: C, 45.7; H, 5.2; N, 4.8; S, 11.1; Found: C, 45.6; H, 5.2; N, 4.8; S, 11.1.

REFERENCE EXAMPLE 14

Methyl 3-Hydroxy-2-[(4-methoxybenzenesulfonyl)-(2-nitrobenzyl)amino]propionate

To a solution of 15.0 g (51.85 mmol) of methyl 3-hydroxy-2-(4-methoxybenzenesulfonylamino)propionate in 125 ml of N,N-dimethylformamide, cooled in an ice bath, was added portionwise 2.29 g (57.03 mmol) of NaH (60% in oil). The mixture was stirred at 0° C. for 20 minutes and then a solution of 12.32 g (57.03 mmol) of 2-nitrobenzyl bromide in 25 ml of dry N,N-dimethylformamide was added dropwise. The solution was stirred at room temperature for 48 hours and diluted with 500 ml of ethyl acetate and water. The organic layer was separated and the aqueous layer extracted with 250 ml of ethyl acetate. The combined organic layer and extract was washed with 200 ml each of H$_2$O, 1 N NaHCO$_3$, brine and dried with Na$_2$SO$_4$. The solvent was removed and the residual solid was triturated with ethyl acetate, cooled and filtered to give 13.5 g (61%) of white crystals, having a m.p. 127–129° C. From a small scale run (3.0 g) there was obtained 2.32 g of white crystals, having a m.p. 127–129° C. Anal. for C$_{18}$H$_{20}$N$_2$O$_8$S: Calc'd: C, 50.9; H, 4.8; N, 6.6; Found: C, 50.9; H, 4.8; N, 6.5.

REFERENCE EXAMPLE 15

Methyl 2-[(2-Aminobenzyl)-(4-methoxybenzenesulfonyl)amino]-3-hydroxypropionate

To a mixture under nitrogen of 1.5 g (3.53 mmol) of methyl 3-hydroxy-2-[(4-methoxybenzenesulfonyl)-(2-nitrobenzyl)amino]propionate in 5 ml of dry ethanol was added 1.12 g (17.69 mmol) of ammonium formate followed by the addition of 0.50 g of 10% palladium on carbon. The mixture was stirred overnight at room temperature and heated at 80° C. for 2 hours. The mixture was filtered through diatomaceous earth and the filtrate concentrated to dryness under vacuum to give a semisolid. Trituration with ethyl acetate gave 0.65 g (47%) of white crystals, m.p. 138–140° C.; Anal. for C$_{18}$H$_{22}$N$_2$O$_6$S: Calc'd: C, 54.8; H, 5.6; N, 7.1; Found: C, 53.0; H, 5.6; N, 6.8.

REFERENCE EXAMPLE 16

Methyl 3-Hydroxy-2-{(4-methoxybenzenesulfonyl)-[2-(2,2,2-trifluoroacetylamino)benzyl]amino}propionate To a solution of 0.50 g (1.27 mmol) of methyl 2-[(2-aminobenzyl)-(4-methoxybenzenesulfonyl)amino]-3-hydroxypropionate in 5 ml of $CH_2Cl_2$ was added 1.8 ml (12.7 mmol) of trifluoroacetic anhydride. The solution was stirred for 1 hour and concentrated to dryness under vacuum. Methanol was added to the residue and the solvent was removed under vacuum. The addition of methanol and concentration to dryness was repeated twice. The residue was chromatographed on silica gel thick layer plates with hexane-ethyl acetate (1:1) to give 0.50 g of a colorless glass. Anal. for $C_{20}H_{21}F_3N_2O_7S$: Calc'd: C, 49.0; H, 4.3; N, 5.7; Found: C, 49.0; H, 4.5; N, 5.4.

REFERENCE EXAMPLE 17

Methyl 2-[(4-Methoxybenzenesulfonyl)-(2-nitrobenzyl)amino]acrylate

To a solution of 1.0 g (2.356 mmol) of methyl 3-hydroxy-2-[(4-methoxybenzenesulfonyl)-(2-nitrobenzyl)amino]propionate in 2 ml of pyridine, cooled to −10° C. was added 0.539 g (2.83 mmol) of 4-methylbenzeuesulfonyl chloride. The solution was chilled overnight and 4 ml of pyridine and 0.539 g (2.83 mmol) of 4-methylbenzene-sulfonyl chloride were added. The mixture was stirred and chilled at −10° C. for 24 hours and diluted with $H_2O$. The mixture was extracted with ethyl acetate and the extract washed with $H_2O$, 2 N citric acid, and brine and then dried ($Na_2SO_4$). The solvent was removed under vacuum to give 1.2 g of an oil. The oil was dissolved in 6 ml of pyridine and 1.08 g of 4-methylbenzenesulfonyl chloride was added thereto. The mixture was stirred at room temperature overnight and diluted with $H_2O$. The mixture was extracted with ethyl acetate and the extract was washed with H2O, 2 N citric acid, and brine and then dried with $Na_2SO_4$. The solvent was removed to give 1.0 g of brown oil. The oil was crystallized from ethanol to give white crystals, m.p. 65–67° C. Anal. for $C_{18}H_{18}N_2O_7S$: Calc'd: C, 53.2; H, 4.5; N, 6.9; Found: C, 53.7; H, 4.5; N, 7.2.

REFERENCE EXAMPLE 18

Methyl 2-{(4-Methoxybenzenesulfonyl)-[2-(4-pyrlidinylcarbonyl)aminobenzyl]amino}acrylate To a mixture of 1.5 g (3.80 mmol) of methyl 2-[(2-aminobenzyl)-(4-methoxybenzenesulfonyl)amino]-3-hydroxypropionate and 3.0 ml (21.6 mmol) of triethylamine in 15 ml of $CH_2Cl_2$, cooled to 0° C. was added 1.7 g (9.5 mmol) ml of 4-pyridinecarbonyl chloride (isonicotinoyl chloride). The mixture was stirred at room temperature overnight and diluted with $CH_2Cl_2$. The mixture was washed with $H_2O$, 2 N citric acid, and brine and then dried with $Na_2SO_4$. The solvent was removed to give 1.8 g of a light tan solid; Anal. for $C_{24}H_{23}N_3O_6S$: Calc'd: C, 59.9; H, 4.8; N, 8.7; S, 6.6; Found: C, 59.0; H, 4.8; N, 8.5; S, 6.9.

Mass spectrum (ES) 482.6(M+H).

Utilizing the procedure described in Reference Example 18, the following intermediate compounds can be prepared from the appropriately unsubstituted methyl 2-[(2-aminobenzyl)-(4-methoxybenzenesulfonyl)amino]-3-hydroxypropionate or the appropriately substituted methyl 2-[(substituted-2-aminobenzyl)-(4-methoxybenzenesulfonyl)amino]-3-hydroxypropionate.

REFERENCE EXAMPLE 19

Methyl 2-{(4-Methoxybenzenesulfonyl)-[2-(2,2,2-trifluoroacetylamino)benzyl]amino}acrylate white crystals, m.p. 120–121° C. Anal. for $C_{20}H_{19}F_3N_2O_6S$: Calc'd: C, 50.9; H, 4.1; N, 5.9; Found: C, 50.8; H, 4.2; N, 5.6.

REFERENCE EXAMPLE 20

Methyl 2-[(2-Benzoylaminobenzyl)-(4-methoxybenzenesulfonyl)amino]acrylate yellow oil. Anal. for $C_{25}H_{24}N_2O_6S$: Calc'd: C, 62.5; H, 5.0; N, 5.8; Found: C, 62.7; H, 5.3; N, 5.0.

REFERENCE EXAMPLE 21

Methyl 2-[(2-Acetylaminobenzyl)-(4-methoxybenzenesulfonyl)amino]acrylate

Reference Example 22

Methyl 2-((4-Methoxybenzenesulfonyl)-{2-[(3-pyridinylcarbonyl)amino]benzyl}amino)acrylate off-white solid. Anal. for $C_{24}H_{23}N_3O_6S$: Calc'd: C, 59.9; H, 4.8; N, 8.7; S, 6.6; Found: C, 58.9; H, 4.8; N, 8.4; S, 6.4.

Mass spectrum (ES) 482.8(M+H).

REFERENCE EXAMPLE 23

Methyl 2-((4-Methoxybenzenesulfonyl)-{[(2-thienylcarbonyl)amino]benzyl}amino)acrylate tan solid. Anal. for $C_{23}H_{22}N_2O_6S_2$: Calc'd: C, 56.8; H, 4.6; N, 5.8; Found: C, 55.7; H, 4.4; N, 4.9.

REFERENCE EXAMPLE 24

Methyl 2-{[2-(-Methoxyacetylamino)benzyl]-(4-methoxybenzenesulfonyl)amino}acrylate yellow oil. Anal. for $C_{21}H_{24}N_2O_7S$: Calc'd: C, 56.2; H, 5.4; N, 6.3; Found: C, 55.3; H, 5.6; N, 5.8.

REFERENCE EXAMPLE 25

Methyl 2-{(4-Methoxybenzenesulfonyl)-[2-(n-propylsulfonylamino)benzyl]amino}acrylate light brown oil. Anal. for $C_{21}H_{26}N_2O_7S_2$: Calc'd: C, 52.3; H, 5.4; N, 5.8; Found: C, 51.9; H, 5.4; N, 5.7.

REFERENCE EXAMPLE 26

Methyl 2-{[2-(3-Phenylpropionyl)aminobenzyl]-(4-methoxybenzenesulfonyl)amino}acrylate light brown oil. Anal. for $C_{27}H_{28}N_2O_6S$: Calc'd: C, 63.8; H, 5.6; N, 5.5; Found: C, 66.7; H, 5.8; N, 4.1.

REFERENCE EXAMPLE 27 tert-Butyl 2-{[2-(3-Trifluoromethylbenzoyl)
aminobenzyl]-(4-methoxybenzenesulfonyl)
amino}acrylate yellow solid; m.p. 65–72° C.

REFERENCE EXAMPLE 28

Methyl 2-{[2-(4-Biphenylcarbonyl)aminobenzyl]-
(4-methoxybenzenesulfonyl)amino}acrylate white solid. Anal for $C_{31}H_{28}N_2O_6S$: Calc'd: C, 66.9; H, 5.1; N, 5.0; Found: C, 66.1; H, 5.0; N, 5.1.

REFERENCE EXAMPLE 29

Methyl 2-{[2-(Cyclopropylcarbonyl)aminobenzyl]-
(4-methoxybenzenesulfonyl)amino}acrylate yellow oil. Anal. for $C_{22}H_{24}N_2O_6S$: Calc'd: C, 59.5; H, 5.4; N, 6.3; Found: C, 60.0; H, 5.7; N, 6.0.
Mass spectrum (ES) 445.5 (M+H).

REFERENCE EXAMPLE 30

Methyl 2-{[2-(Cyclohexylcarbonyl)aminobenzyl]-
(4-methoxybenzenesulfonyl)amino}acrylate white foam. Anal. for $C_{25}H_{30}N_2O_6S$: Calc'd: C, 61.7; H, 6.2; N, 5.8; Found: C, 59.1; H, 6.0; N, 5.4.
Mass spectrum (ES) 487.5 (M+H).

REFERENCE EXAMPLE 31

Methyl 2-{[2-(3-Fluorobenzoyl)aminobenzyl]-(4-
methoxybenzenesulfonyl)amino}acrylate

REFERENCE EXAMPLE 32

Methyl 2-{[2-(3-Chlorobenzoyl)aminobenzyl]-(4-
methoxybenzenesulfonyl)amino}acrylate

REFERENCE EXAMPLE 33

Methyl 2-{[2-(2,4-Dichlorobenzoyl)aminobenzyl]-
(4-methoxybenzenesulfonyl)amino}acrylate

REFERENCE EXAMPLE 34

Methyl 2-{[2-(2,3-Difluorobenzoyl)aminobenzyl]-
(4-methoxybenzenesulfonyl)amino}acrylate

REFERENCE EXAMPLE 35

Methyl 2-{[2-(2-Chloro-4-fluorobenzoyl)
aminobenzyl]-(4-methoxybenzenesulfonyl)
amino}acrylate

REFERENCE EXAMPLE 36

Methyl 2-{[2-(2-Furanylcarbonyl)aminobenzyl]-(4-
methoxybenzenesulfonyl)amino}acrylate off-white solid. Anal. for $C_{23}H_{22}N_2O_7S$. Calc'd: C, 58.7; H, 4.7; N, 6.0; Found: C, 58.0; H, 4.1; N, 3.8.
Mass Spectrum (ES) 470.9 (M+H).

REFERENCE EXAMPLE 37

Methyl 2-((4-Methoxybenzenesulfonyl)-{2-[(3-
thienylcarbonyl)amino]benzyl}amino)acrylate

REFERENCE EXAMPLE 38

Methyl 2-{[2-(2-Acetylaminoacetyl)aminobenzyl]-
(4-methoxybenzenesulfonyl)amino}acrylate

REFERENCE EXAMPLE 39

Methyl 2-{[2-(2-Dimethylacetyl)aminobenzyl]-(4-
methoxybenzenesulfonyl)amino}acrylate

REFERENCE EXAMPLE 40

Methyl 2-{[2-(Cyclobutylcarbonyl)aminobenzyl]-(4-
methoxybenzenesulfonyl)amino}acrylate

REFERENCE EXAMPLE 41

Methyl 1-Methoxyacetyl-4-(4-
methoxybenzenesulfonyl)-2,3,4,5-tetrahydro-1H-[1,
4]benzodiazepine-3-carboxylate To a mixture of 0.449 g (1 mmol) of methyl 2-[[2-(2-methoxyacetamido)benzyl]-(4-methoxybenzene-sulfonyl]amino]acrylate in 5 ml of anhydrous methanol was added 0.109 g (1.3 mmol) of anhydrous sodium bicar-bonate. The mixture was stirred at room temperature overnight and the solvent removed under vacuum. To the residue was added ethyl acetate and water. The organic layer was separated and washed with $H_2O$ and brine and then dried with $Na_2SO_4$. The solvent was removed to give 0.41 g of solid. The solid was crystallized from ethyl acetate to give 0.28 g of white crystals, m.p. 160–163° C. Anal. for $C_{21}H_{24}N_2O_7S$: Calc'd: C, 56.2; H, 5.4; N, 6.3; Found: C, 56.1; H, 5.3; N, 6.3; S, 6.9.
Mass spectrum (ES) 449.1 (M+H).

Utilizing the procedure in Reference Example 41, the following intermediate compounds can be prepared from the appropriate methyl 2-{(4-methoxybenzenesulfonyl)-[2-(substituted amino)benzyl]amino}acrylates.

REFERENCE EXAMPLE 42

Methyl 4-(4-Methoxybenzenesulfonyl)-1-(4-
methylphenylsulfonyl)-2,3,4,5-tetrahydro-1H-[1,4]
benzodiazepine-3-carboxylate white foam. Anal. for $C_{25}H_{26}N_2O_7S_2$: Calc'd: C, 56.6; H, 4.9; N, 5.3 Found: C, 56.2; H, 5.2; N, 5.2.

REFERENCE EXAMPLE 43

Methyl 1,4-Bis-(4-methoxybenzenesulfonyl)-2,3,4,
5-tetrahydro-1H-[1,4]benzodiazepine-3-carboxylate white solid. Anal. for $C_{25}H_{26}N_2O_8S_2$: Calc'd: C, 54.9; H, 4.8; N, 5.1; Found: C, 54.8; H, 4.9; N, 5.1.

REFERENCE EXAMPLE 44

Methyl 1-Methanesulfonyl-4-(4-methoxybenzeuesulfonyl)-2,3,4,5-tetrahydro-1H-[1,4]benzodiazepine-3-carboxylate white crystals, m.p. 136–137° C. Anal. for $C_{19}H_{22}N_2O_7S_2$: Calc'd: C, 50.2; H, 4.9; N, 6.2; Found: C, 50.1; H, 4.9; N, 6.4.

REFERENCE EXAMPLE 45

Methyl 1-Benzoyl-4-(4-methoxybenzenesulfonyl)-2,3,4,5-tetrahydro-1H-[1,4]benzodiazepine-3-carboxylate tan solid. Anal. for $C_{25}H_{24}N_2O_2S$: Calc'd: C, 62.2; H, 5.4; N, 5.8; Found: C, 62.3; H, 5.2; N, 5.6.

REFERENCE EXAMPLE 46

Methyl 1-Acetyl-4-(4-methoxybenzenesulfonyl)-2,3,4,5-tetrahydro-1H-[1,4]benzodiazepine-3-carboxylate white crystals, m.p. 150–155° C. Anal. for $C_{20}H_{22}N_2O_6S$: Calc'd: C, 57.4; H, 5.3; N, 6.7; Found: C, 56.6; H, 5.2; N, 6.5.

REFERENCE EXAMPLE 47

Methyl 4-(4-Methoxybenzenesulfonyl)-1-(3-pyridinylcarbonyl)-2,3,4,5-tetrahydro-1H-[1,4]benzodiazepine-3-carboxylate off-white solid; Anal. for $C_{24}H_{23}N_3O_6S$: Calc'd: C, 59.9; H, 4.8; N, 8.7; Found: C, 59.2; H, 4.8; N, 8.3.
Mass spectrum (ES) 482.2 (M+H).

REFERENCE EXAMPLE 48

Methyl 4-(4-Methoxybenzenesulfonyl)-1-(2-thienylcarbonyl)-2,3,4,5-tetrahydro-1H-[1,4]benzodiazepine-3-carboxylate off-white solid. Anal. for $C_{23}H_{22}N_2O_6S_2$: Calc'd: C, 56.8; H, 4.6; N, 5.8; Found: C, 56.0; H, 4.6; N, 5.2.

REFERENCE EXAMPLE 49

Methyl 4-(4-Methoxybenzenesulfonyl)-1-(4-pyridinylcarbonyl)-2,3,4,5-tetrahydro-1H-[1,4]benzodiazepine-3-carboxylate off-white crystals, m.p. 162–164° C. Anal. for $C_{24}H_{23}N_3O_6S$: Calc'd: C, 59.9; H, 4.8; N, 8.7; Found: C, 59.9; H, 4.8; N, 8.7.

REFERENCE EXAMPLE 50

Methyl 1-(4-Biphenylcarbonyl)-4-(4-methoxybenzenesulfonyl)-2,3,4,5-tetrahydro-1H-[1,4]benzodiazepine-3-carboxylate white solid; Anal. for $C_{31}H_{28}N_2O_6S$: Calc'd: C, 66.9; H, 5.1; N, 5.0; Found: C, 65.8; H, 5.2; N, 5.0.
Mass spectrum (ES) 557.6 (M+H).

REFERENCE EXAMPLE 51

Methyl 4-(4-Methoxybenzenesulfonyl)-1-(propane-1-sulfonyl)-2,3,4,5-tetrahydro-1H-[1,4]benzodiazepine-3-carboxylate yellow oil. Anal. for $C_{21}H_{26}N_2O_7S_2$: Calc'd: C, 52.3; H, 5.4; N, 5.8; Found: C, 51.8; H, 5.4; N, 5.6.

REFERENCE EXAMPLE 52

Methyl 1-([1,1'-Biphenyl]-2-carbonyl)-4-(4-methoxybenzenesulfonyl)-2,3,4,5-tetrahydro-1H-[1,4]benzodiazepine-3-carboxylate white foam. Anal. for $C_{31}H_{28}N_2O_6S$: Calc'd: C, 66.9; H, 5.1; N, 5.0; Found: C, 67.3; H, 5.2; N, 4.7.
Mass spectrum (ES) 557.6 (M+H).

REFERENCE EXAMPLE 53

Methyl 1-(3-Fluorobenzoyl)-4-(4-methoxybenzenesulfonyl)-2,3,4,5-tetrahydro-1H-[1,4]benzodiazepine-3-carboxylate

REFERENCE EXAMPLE 54

Methyl 4-(4-Methoxybenzenesulfonyl)-1-(2-methyl-5-fluorobenzoyl)-2,3,4,5-tetrahydro-1H-[1,4]benzodiazepine-3-carboxylate white solid; Anal. for $C_{26}H_{25}FN_2O_6S$: Calc'd: C, 60.9; H, 4.9; N, 5.5; Found: C, 60.9; H, 5.0; N, 5.0.

REFERENCE EXAMPLE 55

Methyl 4-(4-Methoxybenzenesulfonyl)-1-(2-methyl-3-fluorobenzoyl)-2,3,4,5-tetrahydro-1H-[1,4]benzodiazepine-3-carboxylate

REFERENCE EXAMPLE 56

Methyl 4-(4-Methoxybenzenesulfonyl)1-(3-phenylpropionyl)-2,3,4,5-tetrahydro-1H-[1,4]benzodiazepine-3-carboxylate white solid; Anal. for $C_{27}H_{28}N_2O_6S$: Calc'd: C, 63.8; H, 5.6; N, 5.5; Found: C, 64.0; H, 5.7; N, 5.3; S, 6.5.

REFERENCE EXAMPLE 57

Methyl 4-(4-Methoxybenzenesulfonyl)1-(2-trifluoromethylbenzoyl)-2,3,4,5-tetrahydro-1H-[1,4]benzodiazepine-3-carboxylate

REFERENCE EXAMPLE 58

Methyl 1-(2-Chloro-6-trifluoromethylbenzoyl)-4(4-methoxybenzenesulfonyl)-2,3,4,5-tetrahydro-1H-[1,4]benzodiazepine-3-carboxylate

REFERENCE EXAMPLE 59

Methyl 1-(4-Fluoro-2-trifluoromethylbenzoyl)-4-(4-methoxybenzenesulfonyl)-2,3,4,5-tetrahydro-1H-[1,4]benzodiazepine-3-carboxylate

REFERENCE EXAMPLE 60

Methyl 1-(2-Fluoro-6-trifluoromethylbenzoyl)-4-(4-methoxybenzenesulfonyl)-2,3,4,5-tetrahydro-1H-[1,4]benzodiazepine-3-carboxylate

REFERENCE EXAMPLE 61

Methyl 4-(4-Methoxybenzenesulfonyl)1-(2-methylbenzoyl)-2,3,4,5-tetrahydro-1H-[1,4]benzodiazepine-3-carboxylate

REFERENCE EXAMPLE 62

Methyl 4-(4-Methoxybenzenesulfonyl)-1-(2-methyl-6-chlorobenzoyl)-2,3,4,5-tetrahydro-1H-[1,4]benzodiazepine-3-carboxylate

REFERENCE EXAMPLE 63

Methyl 1-(2,4-Dimethylbenzoyl)-4-(4-methoxybenzenesulfonyl)-2,3,4,5-tetrahydro-1H-[1,4]benzodiazepine-3-carboxylate

REFERENCE EXAMPLE 64

Methyl 1-(2,5-Dimethylbenzoyl)-4-(4-methoxybenzenesulfonyl)-2,3,4,5-tetrahydro-1H-[1,4]benzodiazepine-3-carboxylate

REFERENCE EXAMPLE 65

Methyl 1-(2-Chloro-4-fluorobenzoyl)-4-(4-methoxybenzenesulfonyl)-2,3,4,5-tetrahydro-1H-[1,4]benzodiazepine-3-carboxylate

REFERENCE EXAMPLE 66

Methyl 1-(2-Chlorobenzoyl)-4-(4-methoxybenzenesulfonyl)-2,3,4,5-tetrahydro-1H-[1,4]benzodiazepine-3-carboxylate

REFERENCE EXAMPLE 67

Methyl 1-(2-Fluorobenzoyl)-4-(4-methoxybenzenesulfonyl)-2,3,4,5-tetrahydro-1H-[1,4]benzodiazepine-3-carboxylate

REFERENCE EXAMPLE 68

Methyl 1-(2-Chloro-6-fluorobenzoyl)-4-(4-methoxybenzenesulfonyl)-2,3,4,5-tetrahydro-1H-[1,4]benzodiazepine-3-carboxylate

REFERENCE EXAMPLE 69

Methyl 1-(2,3-Difluorobenzoyl)-4-(4-methoxybenzenesulfonyl)-2,3,4,5-tetrahydro-1H-[1,4]benzodiazepine-3-carboxylate

REFERENCE EXAMPLE 70

Methyl 1-(2,4-Dichlorobenzoyl)-4-(4-methoxybenzenesulfonyl)-2,3,4,5-tetrahydro-1H-[1,4]benzodiazepine-3-carboxylate Prepared according to the procedure set forth in Reference Example 10; white solid. Anal. for $C_{25}H_{22}Cl_{12}N_2O_6S$: Calc'd: C, 54.7; H, 4.0; N, 5.1; Found: C, 54.4; H, 3.8; N, 4.9.

Mass spectrum (548.9) (M+H); 550.9 (M+H).

REFERENCE EXAMPLE 71

Methyl 1-(2,3-Dichlorobenzoyl)-4-(4-methoxybenzenesulfonyl)-2,3,4,5-tetrahydro-1H-[1,4]benzodiazepine-3-carboxylate

REFERENCE EXAMPLE 72

Methyl 1-(2,5-Dichlorobenzoyl)-4-(4-methoxybenzenesulfonyl)-2,3,4,5-tetrahydro-1H-[1,4]benzodiazepine-3-carboxylate

REFERENCE EXAMPLE 73

Methyl 1-(2-Methoxybenzoyl)-4-(4-methoxybenzenesulfonyl)-2,3,4,5-tetrahydro-1H-[1,4]benzodiazepine-3-carboxylate

REFERENCE EXAMPLE 74

Methyl 1-(4-Chloro-2-methoxybenzoyl)-4-(4-methoxybenzenesulfonyl)-2,3,4,5-tetrahydro-1H-[1,4]benzodiazepine-3-carboxylate

REFERENCE EXAMPLE 75

Methyl 4-(4-Methoxybenzenesulfonyl)-1-(2-methylthiobenzoyl)-2,3,4,5-tetrahydro-1H-[1,4]benzodiazepine-3-carboxylate

REFERENCE EXAMPLE 76

Methyl 4-(4-Methoxybenzenesulfonyl)-1-(3-methyl-2-thienylcarbonyl)-2,3,4,5-tetrahydro-1H-[1,4]benzodiazepine-3-carboxylate

REFERENCE EXAMPLE 77

Methyl 4-(4-Methoxybenzenesulfonyl)-1-(4-methyl-2-thienylcarbonyl)-2,3,4,5-tetrahydro-1H-[1,4]benzodiazepine-3-carboxylate

REFERENCE EXAMPLE 78

Methyl 1-(3-Chloro-2-thienylcarbonyl)-4-(4-methoxybenzenesulfonyl)-2,3,4,5-tetrahydro-1H-[1,4]benzodiazepine-3-carboxylate

REFERENCE EXAMPLE 79

Methyl 1-(2-Furanylcarbonyl)-4-(4-methoxybenzenesulfonyl)-2,3,4,5-tetrahydro-1H-[1,4]benzodiazepine-3-carboxylate off-white solid, m.p. 165–167° C. Anal. for $C_{23}H_{22}N_2O_7S$: Calc'd: C, 58.7; H, 4.7; N, 6.0; Found: C, 58.4; H, 4.6; N, 5.7.
Mass spectrum (ES) 470.9 (M+H).

REFERENCE EXAMPLE 80

Methyl 4-(4-Methoxybenzenesulfonyl)-1-(3-methyl-2-furanylcarbonyl)-2,3,4,5-tetrahydro-1H-[1,4]benzodiazepine-3-carboxylate

REFERENCE EXAMPLE 81

Methyl 4-(4-Methoxybenzenesulfonyl)1-(4-methyl-2-furanylcarbonyl)-2,3,4,5-tetrahydro-1H-[1,4]benzodiazepine-3-carboxylate

REFERENCE EXAMPLE 82

Methyl 1-(5-Chloro-2-furanylcarbonyl)-4-(4-methoxybenzenesulfonyl)-2,3,4,5-tetrahydro-1H-[1,4]benzodiazepine-3-carboxylate

REFERENCE EXAMPLE 83

Methyl 1-(5-Chloro-2-thienylcarbonyl)-4-(4-methoxybenzenesulfonyl)-2,3,4,5-tetrahydro-1H-[1,4]benzodiazepine-3-carboxylate

REFERENCE EXAMPLE 84

Methyl 1-Propionyl-4(4-methoxybenzenesulfonyl)-2,3,4,5-tetrahydro-1H-[1,4]benzodiazepine-3-carboxylate

REFERENCE EXAMPLE 85

Methyl 1-Hexanoyl-4-(4-methoxybenzenesulfonyl)-2,3,4,5-tetrahydro-1H-[1,4]benzodiazepine-3-carboxylate

REFERENCE EXAMPLE 86

Methyl 1-(3-Methoxypropionyl)-4-(4-methoxybenzenesulfonyl)-2,3,4,5-tetrahydro-1H-[1,4]benzodiazepine-3-carboxylate

REFERENCE EXAMPLE 87

Methyl 4-(4-Methoxybenzenesulfonyl)1-(3-thienylcarbonyl)-2,3,4,5-tetrahydro-1H-[1,4]benzodiazepine-3-carboxylate

REFERENCE EXAMPLE 88

Methyl 1-(3-Furanylcarbonyl)-4-(4-methoxybenzenesulfonyl)-2,3,4,5-tetrahydro-1H-[1,4]benzodiazepine-3-carboxylate

REFERENCE EXAMPLE 89

Methyl 1-(trans-Crotonyl)-4-(4-methoxybenzenesulfonyl)-2,3,4,5-tetrahydro-1H-[1,4]benzodiazepine-3-carboxylate

REFERENCE EXAMPLE 90

Methyl 1-(Methacryloyl)-4-(4-methoxybenzenesulfonyl)-2,3,4,5-tetrahydro-1H-[1,4]benzodiazepine-3-carboxylate

REFERENCE EXAMPLE 91

Methyl 1-(Chloroacetyl)-4-(4-methoxybenzenesulfonyl)-2,3,4,5-tetrahydro-1H-[1,4]benzodiazepine-3-carboxylate Following the method described for Reference Example 18, 3.0 g (7.61 mmol) of methyl 2-[2-aminobenzyl)-(4-methoxy-benzenesulfonyl)-amino]-3-hydroxy-propionate was reacted with 1.82 ml (22.8 mmol) of chloroacetylchloride to give 4.0 g of solid. Chromatography on silica gel with ethyl acetate-hexane (1:1) as a solvent gave 1.5 g of methyl 2-[(2-chloroacetylaminobenzyl)-(4-methoxybenzenesulfonyl)-amino]acrylate. A 1.3 g sample of the preceding compound was reacted with 0.312 g of anhydrous $NaHCO_3$ in 10 ml of anhydrous methanol at room temperature overnight and the mixture was then heated at 80° C. for 5 hours. The solvent was removed and the residue partitioned between $H_2O$ and ethyl acetate. The ethyl acetate extract was washed with brine, dried with $Na_2SO_4$ and the solvent removed. The residue was triturated with hexane-ethyl acetate, chilled and filtered to give the product; Mass spectrum (ES) 453.1 (M+H).

REFERENCE EXAMPLE 92

Methyl 1-(Acetylaminoacetyl)-4-(4-methoxybenzenesulfonyl)-2,3,4,5-tetrahydro-1H-[1,4]benzodiazepine-3-carboxylate

REFERENCE EXAMPLE 93

Methyl 1-(N,N-Dimethylaminoacetyl)-4-(4-methoxybenzenesulfonyl)-2,3,4,5-tetrahydro-1H-[1,4]benzodiazepine-3-carboxylate

REFERENCE EXAMPLE 94

Methyl 1-(Cyclopropylcarbonyl)-4-(4-methoxybenzenesulfonyl)-2,3,4,5-tetrahydro-1H-[1,4]benzodiazepine-3-carboxylate white crystals, m.p. 98–100° C. Anal. for $C_{22}H_{24}N_2O_6S$: Calc'd: C, 59.5; H, 5.4; N, 6.3; Found: C, 59.3; H, 5.6; N, 6.2.
Mass spectrum (ES) 445.1 (M+H).

REFERENCE EXAMPLE 95

Methyl 1-(Cyclobutylcarbonyl)-4-(4-methoxybenzenesulfonyl)-2,3,4,5-tetrahydro-1H-[1,4]benzodiazepine-3-carboxylate

REFERENCE EXAMPLE 96

Methyl 4-(4-Methoxybenzenesulfonyl)1-(trifluoroacetyl)-2,3,4,5-tetrahydro-1H-[1,4]benzodiazepine-3-carboxylate To a solution of 1.0 g (2.54 mmol) of methyl 3-hydroxy-2-{(4-methoxybenzenesulfonyl)-[2-(2,2,2-trifluoroacetylamino)benzyl]amino}propionate in 10 ml of $CH_2Cl_2$ was added 1.8 ml (12.7 mmol) of trifluoroacetic anhydride. After 1 hour at room temperature, the solvent was removed. Dichloromethane was added several times and the solvent removed under vacuum after each addition. Methanol was then added 2 times and the solvent removed under vacuum to give methyl 2-{(4-methoxybenzenesulfonyl)-[2-(2,2,2-trifluoroacetylamino)benzyl]-amino}acrylate as a glass. The glass was dissolved in methanol and 0.213 g of anhydrous $NaHCO_3$ was added. The mixture was stirred at room temperature overnight and concentrated under vacuum to dryness. To the residue was added ethyl acetate and water. The organic layer was separated, washed with $H_2O$, brine and dried with $Na_2SO_4$. The solvent was removed and the residue (1.0 g) was chromatographed on silica gel thick layer plates with hexane-ethyl acetate (1:1) as solvent to give 0.365 g of product as a glass. Anal. for $C_{20}H_{19}F_3N_2O_6S$: Calc'd: C, 50.9; H, 4.1; N, 5.9; F, 12.1; S, 6.7; Found: C, 50.8; H, 4.4; N, 5.5; F, 11.7; S, 6.7.

Mass spectrum (ES) 473.1 (M+H).

REFERENCE EXAMPLE 97

Methyl 4-(4-Methoxybenzenesulfonyl)-1-(4-methylphenylsulfonyl)-2,3,4,5-tetrahydro-1H-[1,4]benzodiazepine-3-carboxylate To 0.50 g (1.26 mmol) of 2-[(2-aminobenzyl)-(4-methoxybenzenesulfonyl)amino]-3-hydroxypropionate in 5 ml of pyridine cooled to 0° C. was added 0.284 g (2.59 mmol) of tosyl chloride. The mixture was stirred at 0° C. for 2 hours and then concentrated to remove the solvent. To the residue was added 8 ml of anhydrous ethanol and the mixture refluxed for 2 days. The mixture was concentrated to dryness and ethyl acetate added. The mixture was washed with $H_2O$, 2 N citric acid, brine and dried with $Na_2SO_4$. The filtrate was filtered through a thin pad of hydrous magnesium silicate and the filter pad washed with ethyl acetate. The filtrate was concentrated to dryness to give 0.60 g of a foam. Anal. for $C_{25}H_{26}N_2O_7S_2$: Calc'd: C, 56.6; H, 4.9; N, 5.3; S, 12.1; Found: C, 56.2; H, 5.2; N, 5.2; S, 11.4.

Mass spectrum (ES) 531.6 (M+H).

REFERENCE EXAMPLE 98

Methyl 2-[(4-Methoxybenzenesulfonyl)-(2-methylsulfonylaminobenzyl)amino]acrylate To a solution of 1.0 g (2.54 mmol) of methyl [(2-aminobenzyl)-(4-methoxybenzenesulfonyl)amino]-3-hydroxypropionate in 10 ml of pyridine cooled to −5° C. was added 0.432 ml (5.58 mmol) of methanesulfonyl chloride. The mixture was stirred at 0° C. for 48 hours. To the mixture was added ice and $H_2O$ and the mixture was extracted with ethyl acetate. The extract was washed with $H_2O$, 2 N citric acid, brine and dried with $Na_2SO_4$. The solvent was removed under vacuum and the residue triturated with ethyl acetate-hexane to give 0.90 g of a solid, 128–142° C. Anal. for $C_{19}H_{22}N_2O_7S_2$: Calc'd: C, 50.2; H, 4.9; N, 6.2; S, 14.1; Found: C, 49.6; H, 5.0; N, 6.9; S, 14.0.

Mass spectrum (ES) 455.5 (M+H).

REFERENCE EXAMPLE 99

Methyl 1,4-Bis-(4-Methoxybenzenesulfonyl)-2,3,4,5-tetrahydro-1H-[1,4]benzodiazepine-3-carboxylate To a solution of 1.0 g (2.34 mmol) of methyl 2-[(2-aminobenzyl)-(4-methoxybenzenesulfonyl)amino]-3-hydroxypropionate in 6 ml of pyridine cooled to 0° C. to −5° C. was added 1.07 (5.18 mmol) of 4-methoxybenzenesulfonyl chloride. After 2 hours, the mixture was concentrated to dryness under vacuum. To the residue was added 12 ml of ethanol and the mixture refluxed overnight. The solvent was removed under vacuum and the residue chromatographed on silica gel thick layer plates with ethyl acetate-hexane (1:1) as solvent to give 0.83 g (60%) of product as a white foam; Anal. calc'd for $C_{25}H_{26}N_2O_8S_2$: C, 54.9; H, 4.8; N, 5.1; S, 11.7. Found: C, 54.8; H, 4.9; N, 5.0; S, 11.5; Mass spectrum (ES) 547.1 (M+H); and a second component (0.38 g) methyl 2-{[2-(4-methoxybenzenesulfonyl)aminobenzyl]-(4-methoxybenzenesulfonyl)amino}-3-hydroxypropionate. Anal. for $C_{25}H_{28}N_2O_9S_2$: Calc'd: C, 53.2; H, 5.0; N, 5.0; S, 11.4; Found: C, 51.8; H, 5.1; N, 4.7; S, 11.3.

Mass spectrum (ES) 565.2 (M+H).

REFERENCE EXAMPLE 100

Methyl 1-Acetyl-4-(4-methoxybenzenesulfonyl)-2,3,4,5-tetrahydro-1H-[1,4]benzodiazepine-3-carboxylate To a solution of 0.70 g (1.52 mmol) of methyl 2-[(2-diacetylaminobenzyl)-(4-methoxybenzenesulfonyl)amino]acrylate in 5 ml of anhydrous methanol was added 0.332 g (3.95 mmol) of anhydrous sodium bicarbonate. The mixture was stirred at room temperature overnight and the solvent removed under vacuum. To the residue was added ethyl acetate and $H_2O$. The organic layer was separated, washed with brine and dried with $Na_2SO_4$. The solvent was removed and the residue dried under vacuum to give 0.59 g of white crystals, m.p. 150–155° C. Anal. for $C_{20}H_{22}N_2O_6S$: Calc'd: C, 57.4; H, 5.3; N, 6.7; S, 7.7; Found: C, 56.6; H, 5.2; N, 6.5; S, 7.5.

Mass spectrum (ES) 419.9 (M+H).

REFERENCE EXAMPLE 101

Methyl 3-Acetoxy-2-[(2-diacetylamlnobenzyl)-(4-methoxybenzenesulfonyl)amino]propionate A mixture of 1.0 g (2.54 mmol) of methyl 2-[(2-aminobenzyl)-(4-methoxybenzenesulfonyl)amino]-3-hydroxypropionate and 1.3 ml of acetic anhydride in 8 ml of toluene was heated at 100° C. for 2 hours. The mixture was concentrated and 3 ml of acetic anhydride added thereto. The mixture was heated at 100° C. overnight and concentrated to dryness under high vacuum to give an oil. The oil was dried at 75° C. under vacuum for 48 hours to give 1.2 g of a yellow oil. Anal. for $C_{24}H_{28}N_2O_9S$: Calc'd: C, 54.5; H, 5.2; N, 5.5; S, 6.2; Found: C, 54.6; H, 5.1; N, 5.4; S, 6.4.

Mass spectrum (ES) 520.8 (M+H).

REFERENCE EXAMPLE 102

Methyl 2-[(2-Diacetylaminobenzyl)-(4-methoxybenzenesulfonyl)amino]acrylate

A mixture of 1.0 g (1.97 mmol) of methyl 3-acetoxy-2-[(2-diacetylaminobenzyl)-(4-methoxybenzenesulfonyl)

amino]propionate and 0.826 ml (5.92 mmol) of triethylamine in 5 ml of $CH_2Cl_2$ was stirred at room temperature overnight. The solution was diluted with 30 ml of $CH_2Cl_2$ and washed with 20 ml each of $H_2O$, 2 N citric acid, brine and dried with $Na_2SO_4$. The solvent was removed under vacuum to give a brown oil. Anal. for $C_{22}H_{24}N_2O_7S$: Calc'd: C, 57.4; H, 5.3; N, 6.1; S, 7.0; Found: C, 56.2; H, 5.5; N, 5.6; S, 7.2.

REFERENCE EXAMPLE 103

Methyl 2-{(4-Methoxybenzenesulfonyl)-[2-(2,2,2-trifluoroacetylamino)benzyl]amino}acrylate To a suspension of 1.0 g (2.54 mmol) of methyl 2-[(2-aminobenzyl)-(4-methoxybenzenesulfonyl)amino]-3-hydroxypropionate in 10 ml of toluene was added 1.8 ml (12.7 mmol) of trifluoroacetic anhydride (solid dissolves). The solution was stirred for 2 hours at room temperature and heated at 100° C. overnight. The mixture was then concentrated to dryness under vacuum. To the residue was added 0.9 ml of trifluoroacetic anhydride and the solution stirred at room temperature for 1.5 hours and concentrated to dryness. To the residue was added 10 ml of toluene and the mixture refluxed for 2 hours. The solution was cooled to room temperature and 2.5 ml of triethylamine added and the mixture stirred at room temperature overnight. The solution was concentrated to dryness and the residue dissolved in ethyl acetate. The ethyl acetate was washed with $H_2O$, brine and dried ($Na_2SO_4$). The solvent was removed under vacuum to give 1.0 g of colorless oil. Crystallization from ethyl acetate-hexane gave 0.625 g of colorless crystals, m.p. 120–121° C. Anal. for $C_{20}H_{19}F_3N_2O_6S$: Calc'd: C, 50.9; H, 4.1; N, 5.9; S, 6.7; F,12.1; Found: C, 50.8; H, 4.2; N, 5.6; S, 6.8; F,11.9.

Mass spectrum (ES) 473.1 (M+H).

REFERENCE EXAMPLE 104

4-(4-Methoxybenzenesulfonyl)-1-(2-methyl-5-fluorobenzoyl)-2,3,4,5-tetrahydro-1H-[1,4]benzodiazepine-3-carboxylic Acid To a mixture of 1.9 g (3.71 mmol) of methyl 4-(4-methoxybenzenesulfonyl)-1-(2-methyl-5-fluorobenzoyl)-2,3,4,5-tetrahydro-1H-[1,4]benzodiazepine-3-carboxylate in 10 ml of tetrahydrofuran was added 5 ml (4.82 mmol) of 1 N NaOH. The mixture was stirred at room temperature for 1.5 hours and the solvent removed under vacuum. To the residue was added ethyl acetate and the mixture neutralized with 1 N HCl. The organic layer was separated, washed with brine and dried with $Na_2SO_4$. The solvent was removed under vacuum to give 1.41 g of white solid. Anal. for $C_{25}H_{23}FN_2O_6S$: Calc'd: C, 60.2; H, 4.7; N, 5.6; Found: C, 60.2; H, 4.8; N, 5.4 S, 6.4; F, 3.6.

Mass spectrum (ES) 497.5 (M−H).

Utilizing the method described in Reference Example 104, the following benzodiazepine-3-carboxylic acids can be prepared.

REFERENCE EXAMPLE 105

4-(4-Methoxybenzenesulfonyl)-1-(4-methylphenylsulfonyl)-2,3,4,5-tetrahydro-1H-[1,4]benzodiazepine-3-carboxylic acid white foam. Anal. for $C_{24}H_{24}N_2O_7S_2$: Calc'd: C, 55.8; H, 4.7; N, 5.4; Found: C, 53.9; H, 5.1; N, 4.8.

Mass spectrum (ES) 512.2 (M+H).

REFERENCE EXAMPLE 106

1,4-Bis-(4-methoxybenzenesulfonyl)-2,3,4,5-tetrahydro-1H-[1,4]benzodiazepine-3-carboxylic acid off-white solid. Anal. for $C_{24}H_{24}N_2O_8S_2$: Calc'd: C, 54.1; H, 4.5; N, 5.3; Found: C, 52.4; H, 4.8; N, 4.7.

Mass spectrum (ES) 533.1 (M+H).

REFERENCE EXAMPLE 107

1-Methanesulfonyl-4-(4-methoxybenzenesulfonyl)-2,3,4,5-tetrahydro-1H-[1,4]benzodiazepine-3-carboxylic acid white solid. Anal. for $C_{18}H_{20}N_2O_7S_2$: Calc'd: C, 49.1; H, 4.6; N, 6.3; Found: C, 47.5; H, 5.0; N, 5.5.

Mass spectrum (ES) 441.1 (M+H).

REFERENCE EXAMPLE 108

1-Benzoyl-4-(4-methoxybenzenesulfonyl)-2,3,4,5-tetrahydro-1H-[1,4]benzodiazepine-3-carboxylic acid white foam. Anal. for $C_{24}H_{22}N_2O_6S$: Calc'd C, 61.5; H, 5.2; N, 6.0; Found: C, 60.8; H, 5.2; N, 5.7.

Mass spectrum (ES) 467.9 (M+H).

REFERENCE EXAMPLE 109

1-Acetyl-4-(4-methoxybenzenesulfonyl)-2,3,4,5-tetrahydro-1H-[1,4]benzodiazepine-3-carboxylic acid white solid; Anal. for $C_{19}H_{22}N_2O_6S$: Calc'd: C, 56.4; H, 5.0; N, 6.9; Found: C, 55.2; H, 4.9; N, 6.6; S, 7.8.

Mass spectrum (ES) 404.9 (M+H).

REFERENCE EXAMPLE 110

4-(4-Methoxybenzenesulfonyl)-1-(3-pyridinylcarbonyl)-2,3,4,5-tetrahydro-1H-[1,4]benzodiazepine-3-carboxylic acid white solid; m.p. 250–255. Anal. for $C_{23}H_{21}N_3O_6S$: Calc'd: C, 59.1; H, 4.5; N, 9.0; Found: C, 58.3; H, 4.7; N, 8.3.

Mass spectrum (ES); 468.2 (M+H).

REFERENCE EXAMPLE 111

4-(4-Methoxybenzenesulfonyl)-1-(2-thienylcarbonyl)-2,3,4,5-tetrahydro-1H-[1,4]benzodiazepine-3-carboxylic acid white solid; Anal. for $C_{22}H_{20}N_2O_6S_2$: Calc'd: C, 55.9; H, 4.3; N, 5.9; Found: C, 54.9; H, 4.4; N, 5.4.

Mass spectrum (ES) 473.1 (M+H).

REFERENCE EXAMPLE 112

1-Methoxyacetyl-4-(4-methoxybenzenesulfonyl)-2,3,4,5-tetrahydro-1H-[1,4]benzodiazepine-3-carboxylic acid white crystals, m.p. 193–194° C. Anal. for $C_{20}H_{22}N_2O_7S$: Calc'd: C, 55.3; H, 5.1; N, 6.5; Found: C, 55.1; H, 4.9; N, 6.2.

Mass spectrum (ES) 433.1 (M−H).

REFERENCE EXAMPLE 113

4-(4-Methoxybenzenesulfonyl)-1-(4-pyridinylcarbonyl)-2,3,4,5-tetrahydro-1H-[1,4]benzodiazepine-3-carboxylic acid white crystals, m.p. 258–261° C. Anal. for $C_{23}H_{21}N_3O_6S$: Calc'd: C, 59.1; H, 4.5; N, 9.0; Found: C, 58.8; H, 4.5; N, 8.8.
Mass spectrum (ES) 483.3 (M+H).

REFERENCE EXAMPLE 114

1-(4-Biphenylcarbonyl)-4-(4-methoxybenzenesulfonyl)-2,3,4,5-tetrahydro-1H-[1,4]benzodiazepine-3-carboxylic acid white foam. Anal. for $C_{30}H_{26}N_2O_6S$: Calc'd: C, 66.4; H, 4.8; N, 5.2; Found: C, 64.7; H, 5.2; N, 4.8.
Mass spectrum (ES) 543.6 (M+H).

REFERENCE EXAMPLE 115

4-(4-Methoxybenzenesulfonyl)-1-(propane-1-sulfonyl)-2,3,4,5-tetrahydro-1H-[1,4]benzodiazepine-3-carboxylic acid white foam. Anal. for $C_{20}H_{24}N_2O_7S_2$: Calc'd: C, 51.3; H, 5.2; N, 6.0; Found: C, 50.3; H, 5.3; N, 5.7.
Mass spectrum (ES) 467.3 (M–H).

REFERENCE EXAMPLE 116

1-([1,1'-Biphenyl]-2-carbonyl)-4-(4-methoxybenzenesulfonyl)-2,3,4,5-tetrahydro-1H-[1,4]benzodiazepine-3-carboxylic acid white foam; m.p. 106–145° C. Anal. for $C_{30}H_{26}N_2O_6S$: Calc'd: C, 66.4; H, 4.8; N, 5.2; Found: C, 65.7; H, 5.0; N, 4.8.
Mass spectrum (ES) 541.1 (M–H).

REFERENCE EXAMPLE 117

1-(3-Fluorobenzoyl)-4-(4-methoxybenzenesulfonyl)-2,3,4,5-tetrahydro-1H-[1,4]benzodiazepine-3-carboxylic acid

REFERENCE EXAMPLE 118

4-(4-Methoxybenzenesulfonyl)-1-(2-methyl-3-fluorobenzoyl)-2,3,4,5-tetrahydro-1H-[1,4]benzodiazepine-3-carboxylic acid

REFERENCE EXAMPLE 119

4-(4-Methoxybenzenesulfonyl)-1-(3-phenylpropionyl)-2,3,4,5-tetrahydro-1H-[1,4]benzodiazepine-3-carboxylic acid white solid. Anal. for $C_{26}H_{26}N_2O_6S$: Calc'd: C, 63.1; H, 5.3; N, 5.7; Found: C, 61.5; H, 5.4; N, 5.2.
Mass spectrum (ES) 493.2 (M–H).

REFERENCE EXAMPLE 120

4-(4-Methoxybenzenesulfonyl)-1-(2-trifluoromethylbenzoyl)-2,3,4,5-tetrahydro-1H-[1,4]benzodiazepine-3-carboxylic acid

REFERENCE EXAMPLE 121

1-(2-Chloro-6-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 122

1-(4-Fluoro-2-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 123

1-(2-Fluoro-6-trifluoromethylbenzoyl)-4-(4-methoxybenzenesulfonyl)-2,3,4,5-tetrahydro-1H-[1,4]benzodiazepine-3-carboxylic acid

REFERENCE EXAMPLE 124

4-(4-Methoxybenzenesulfonyl)-1-(2-methylbenzoyl)-2,3,4,5-tetrahydro-1H-[1,4]benzodiazepine-3-carboxylic acid

REFERENCE EXAMPLE 125

4-(4-Methoxybenzenesulfonyl)-1-(2-methyl-6-chlorobenzoyl)-2,3,4,5-tetrahydro-1H-[1,4]benzodiazepine-3-carboxylic acid

REFERENCE EXAMPLE 126

1-(2,4-Dimethylbenzoyl)-4-(4-methoxybenzenesulfonyl)-2,3,4,5-tetrahydro-1H-[1,4]benzodiazepine-3-carboxylic acid

REFERENCE EXAMPLE 127

1-(2,5-Dimethylbenzoyl)-4-(4-methoxybenzenesulfonyl)-2,3,4,5-tetrahydro-1H-[1,4]benzodiazepine-3-carboxylic acid

REFERENCE EXAMPLE 128

1-(2-Chloro-4-fluorobenzoyl)-4-(4-metboxybenzenesulfonyl)-2,3,4,5-tetrahydro-1H-[1,4]benzodiazepine-3-carboxylic acid

REFERENCE EXAMPLE 129

1-(2-Chlorobenzoyl)-4-(4methoxybenzenesulfonyl)-2,3,4,5-tetrahydro-1H-[1,4]benzodiazepine-3-carboxylic acid

REFERENCE EXAMPLE 130

1-(2-Fluorobenzoyl)-4-(4-methoxybenzenesulfonyl)-2,3,4,5-tetrahydro-1H-[1,4]benzodiazepine-3-carboxylic acid

REFERENCE EXAMPLE 131

1-(2-Chloro-6-fluorobenzoyl)-4-(4-methoxybenzenesulfonyl)-2,3,4,5-tetrahydro-1H-[1,4]benzodiazepine-3-carboxylic acid

REFERENCE EXAMPLE 132

1-(2,3-Difluorobenzoyl)-4-(4-methoxybenzenesulfonyl)-2,3,4,5-tetrahydro-1H-[1,4]benzodiazepine-3-carboxylic acid

REFERENCE EXAMPLE 133

1-(2,4-Dichlorobenzoyl)-4-(4-methoxybenzenesulfonyl)-2,3,4,5-tetrahydro-1H-[1,4]benzodiazepine-3-carboxylic acid white solid. Anal. for $C_{24}H_{20}Cl_2N_2O_6S$: Calc'd: C, 53.8; H, 3.8; N, 5.2; Found: C, 52.8; H, 3.9; N, 4.9.
Mass spectrum (ES) 533 (M–H).

REFERENCE EXAMPLE 134

1-(2,3-Dichlorobenzoyl)-4-(4-methoxybenzenesulfonyl)-2,3,4,5-tetrahydro-1H-[1,4]benzodiazepine-3-carboxylic acid

REFERENCE EXAMPLE 135

1-(2,5-Dichlorobenzoyl)-4-(4-methoxybenzenesulfonyl)-2,3,4,5-tetrahydro-1H-[1,4]benzodiazepine-3-carboxylic acid

REFERENCE EXAMPLE 136

1-(2-Methoxybenzoyl)-4-(4-methoxybenzenesulfonyl)-2,3,4,5-tetrahydro-1H-[1,4]benzodiazepine-3-carboxylic acid

REFERENCE EXAMPLE 137

1-(4-Chloro-2-methoxybenzoyl)-4-(4-methoxybenzenesulfonyl)-2,3,4,5-tetrahydro-1H-[1,4]benzodiazepine-3-carboxylic acid

REFERENCE EXAMPLE 138

4-(4-Methoxybenzenesulfonyl)-1-(2-methylthiobenzoyl)-2,3,4,5-tetrahydro-1H-[1,4]benzodiazepine-3-carboxylic acid

REFERENCE EXAMPLE 139

4-(4-Methoxybenzenesulfonyl)-1-(3-methyl-2-thienylcarbonyl)-2,3,4,5-tetrahydro-1H-[1,4]benzodiazepine-3-carboxylic acid

REFERENCE EXAMPLE 140

4-(4-Methoxybenzenesulfonyl)-1-(4-methyl-2-thienylcarbonyl)-2,3,4,5-tetrahydro-1H-[1,4]benzodiazepine-3-carboxylic acid

REFERENCE EXAMPLE 141

1-(3-Chloro-2-thienylcarbonyl)-4-(4-methoxybenzenesulfonyl)-2,3,4,5-tetrahydro-1H-[1,4]benzodiazepine-3-carboxylic acid

REFERENCE EXAMPLE 142

1-(2-Furanylcarbonyl)-4-(4-methoxybenzenesulfonyl)-2,3,4,5-tetrahydro-1H-[1,4]benzodiazepine-3-carboxylic acid white solid. Anal. for $C_{22}H_{20}N_2O_7S$: Calc'd: C, 57.9; H, 4.4; N, 6.1; Found: C, 56.5; H, 4.5; N, 5.7.
Mass spectrum (ES) 455.1 (M–H).

REFERENCE EXAMPLE 143

4-(4-Methoxybenzenesulfonyl)-1-(3-methyl-2-furanylcarbonyl)-2,3,4,5-tetrahydro-1H-[1,4]benzodiazepine-3-carboxylic acid

REFERENCE EXAMPLE 144

4-(4-Methoxybenzenesulfonyl)-1-(4-methyl-2-furanylcarbonyl)-2,3,4,5-tetrahydro-1H-[1,4]benzodiazepine-3-carboxylic acid

REFERENCE EXAMPLE 145

1-(5-Chloro-2-furanylcarbonyl)-4-(4-methoxybenzenesulfonyl)-2,3,4,5-tetrahydro-1H-[1,4]benzodiazepine-3-carboxylic acid

REFERENCE EXAMPLE 146

1-(5-Chloro-2-thienylcarbonyl)-4-(4-methoxybenzenesulfonyl)-2,3,4,5-tetrahydro-1H-[1,4]benzodiazepine-3-carboxylic acid

REFERENCE EXAMPLE 147

1-Propionyl-4-(4-methoxybenzenesulfonyl)-2,3,4,5-tetrahydro-1H-[1,4]benzodiazepine-3-carboxylic acid

REFERENCE EXAMPLE 148

1-Hexanoyl-4-(4-methoxybenzenesulfonyl)-2,3,4,5-tetrahydro-1H-[1,4]benzodiazepine-3-carboxylic acid

REFERENCE EXAMPLE 149

1-(3-Methoxypropionyl)-4-(4-methoxybenzenesulfonyl)-2,3,4,5-tetrahydro-1H-[1,4]benzodiazepine-3-carboxylic acid

REFERENCE EXAMPLE 150

4-(4-Methoxybenzenesulfonyl)-1-(3-thienylcarbonyl)-2,3,4,5-tetrahydro-1H-[1,4]benzodiazepine-3-carboxylic acid

REFERENCE EXAMPLE 151

4-(3-Furanylcarbonyl)-4-(4-methoxybenzenesulfonyl)-2,3,4,5-tetrahydro-1H-[1,4]benzodiazepine-3-carboxylic acid

REFERENCE EXAMPLE 152

1-(trans-Crotonyl)-4-(4-methoxybenzenesulfonyl)-2,3,4,5-tetrahydro-1H-[1,4]benzodiazepine-3-carboxylic acid

REFERENCE EXAMPLE 153

1-(Methacryloyl)-4-(4-methoxybenzenesulfonyl)-2,3,4,5-tetrahydro-1H-[1,4]benzodiazepine-3-carboxylic acid

REFERENCE EXAMPLE 154

1-(Pyrrolidinoacetyl)-4-(4-methoxybenzenesulfonyl)-2,3,4,5-tetrahydro-1H-[1,4]benzodiazepine-3-carboxylic acid

REFERENCE EXAMPLE 155

1-(Acetylaminoacetyl)-4-(4-methoxybenzenesulfonyl)-2,3,4,5-tetrahydro-1H-[1,4]benzodiazepine-3-carboxylic acid

REFERENCE EXAMPLE 156

1-(Cyclopropylcarbonyl)-4-(4-methoxybenzenesulfonyl)-2,3,4,5-tetrahydro-1H-[1,4]benzodiazepine-3-carboxylic acid white crystals, m.p. 131–135° C. Anal. for $C_{21}H_{22}N_2O_6S$: Calc'd: C, 58.6; H, 5.2; N, 6.5; Found: C, 58.1; H, 5.5; N, 5.8.
Mass spectrum (ES) 431.5 (M+H).

REFERENCE EXAMPLE 157

1-(Cyclobutylcarbonyl)-4-(4-methoxybenzenesulfonyl)-2,3,4,5-tetrahydro-1H-[1,4]benzodiazepine-3-carboxylic acid

REFERENCE EXAMPLE 158

1-(Cyclohexylcarbonyl)-4-(4-methoxybenzenesulfonyl)-2,3,4,5-tetrahydro-1H-[1,4]benzodiazepine-3-carboxylic acid white solid. Anal. for $C_{24}H_{28}N_2O_6S$: Calc'd: C, 61.0; H, 6.0; N, 5.9; Found: C, 57.0; H, 5.7; N, 5.4.
Mass spectrum (ES) 471.5 (M−H).

REFERENCE EXAMPLE 159

(D,L)N-(4-Methoxybenzenesulfonyl)-O-(2-tetrahydropyranyl)serine, Methyl ester

A mixture of 1.44 g (5 mmol) of N-(4-methoxybenzenesulfonyl)serine, methyl ester; 1.05 g (12.5 mmol) of 3,4-dihydro-2H-pyran and 9.5 mg of 4-methylbenzene-sulfonic acid monohydrate in 5 ml of tetrahydrofuran was refluxed overnight and the mixture was concentrated to dryness under vaccum. The residue was extracted with $CH_2Cl_2$ and the extract washed with 2 N $NaHCO_3$, brine and dried with $Na_2SO_4$. The solution was filtered through a thin pad of hydrous magnesium silicate and the filter pad washed with $CH_2Cl_2$. The filtrate was concentrated to dryness and the residue (2.3 g) was extracted with three 50 ml portions of hot hexane to give 1.92 g of product as a yellow oil; Mass spectrum (ES) 374.4 (MH$^+$).

REFERENCE EXAMPLE 160

Methyl 3-Hydroxy-2-{[4-methoxybenzenesulfonyl]-[2-(4-morpholinocarbonylamino)benzyl]amino}propionate To a mixture of 1.0 g (2.54 mmol) of methyl 2-[(2-aminobenzyl)-(4-methoxybenzenesulfonyl)amino]-3-hydroxypropionate in 8 ml of pyridine chilled at 0° to −10° C. was added 740 μL (6.34 mmol) of morpholinocarbonyl chloride. The mixture was kept at 0° to 5° C. overnight. The mixture was concentrated under vacuum and diluted with ethyl acetate. The solution was washed with $H_2O$, 2 N citric acid, and brine and dried with $Na_2SO_4$. The solvent was removed under vacuum to give 1.61 g of solid (yellow-orange foam). The solid was chromatographed on thick layer silica gel plates with hexane-ethyl acetate (1:3) as solvent to give 0.86 g of solid. Anal. for $C_{23}H_{29}N_3O_8S$: Calc'd: C, 54.4; H, 5.8; N, 8.3; Found: C, 53.9; H, 5.7; N, 8.1.
Mass spectrum (ES) 508.4 (M+H).

REFERENCE EXAMPLE 161

Methyl 2-{(4-Methoxybenzenesulfonyl)-[2-(4-morpholinocarbonylamino)benzyl]amino}acrylate To a solution of 0.70 g (1.38 mmol) of methyl 3-hydroxy-2-{[4-methoxybenzenesulfonyl]-[2-(4-morpholinocarbonylamino)benzyl]amino}propionate and 769 μL (5.54 mmol) of triethylamine in 8 ml of $CH_2Cl_2$, cooled to 0° C., was added 0.386 g (2.03 mmol) of 4-methylbenzenesulfonyl chloride. The mixture was stirred at room temperature for 2 hours, diluted with water and extracted with $CH_2Cl_2$. The extract was washed with 2 N citric acid, brine and dried with $Na_2SO_4$. The solvent was removed to give 0.67 g of a yellow oil. Anal. for $C_{23}H_{27}N_3O_7S$: Calc'd: C, 56.4; H, 5.6; N, 8.6; S, 6.6; Found: C, 56.1; H, 5.8; N, 8.3; S, 6.6.

REFERENCE EXAMPLE 162

Methyl 4-(4-Methoxybenzenesulfonyl)-1-(4-morpholinocarbonyl)-2,3,4,5-tetrahydro-1H-[1,4]-benzodiazepine-3-carboxylate A mixture of 0.50 g (1.02 mmol) of methyl 2-{(4-methoxybenzenesulfonyl)-[2-(4-morpholinocarbonylamino)benzyl]amino}acrylate and 0.111 g (1.32 mmol) of anhydrous NaHCO$_3$ in 5 ml of anhydrous methanol was stirred at room temperature for 16 hours. An additional 55 mg of NaHCO$_3$ was added and the mixture stirred at room temperature for 2 hours. The solvent was removed under vacuum and the residue diluted with H$_2$O and extracted with ethyl acetate. The extract was washed with brine and dried with Na$_2$SO$_4$. The solvent was removed and the residue triturated with hexane-ethyl acetate to give 0.36 g of a yellow solid; Anal. calc'd for C$_{23}$H$_{27}$N$_3$O$_7$S: C, 56.4; H, 5.6; N, 8.6; S, 6.6. Found: C, 56.5; H, 5.7; N, 8.4; S, 6.7.

Mass spectrum (ES) 490.3 (M+H).

REFERENCE EXAMPLE 163

4-(4-Methoxybenzenesulfonyl)-1-(4-morpholinocarbonyl)-2,3,4,5-tetrahydro-1H-[1,4]benzodiazepine-3-carboxylic Acid A mixture of 0.36 g (0.735 mmol) of methyl 4-(4-methoxybenzenesulfonyl)-1-(4-morpholinocarbonyl)-2,3,4,5-tetrahydro-1H-[1,4]benzodiazepine-3-carboxyl and 1 ml (0.95 mmol) of 1 N NaOH in 5 ml of tetrahydrofuran was stirred at room temperature for 1 hour. The mixture was concentrated under vacuum and the acidified with 1 N HCl and cooled. The mixture was filtered and the solid washed with water to give 0.26 g of white solid. Anal. for C$_{22}$H$_{25}$N$_3$O$_7$S: Calc'd: C, 55.6; H, 5.3; N, 8.8; Found: C, 53.5; H, 5.6; N, 8.3.

Mass spectrum (ES) 474.3 (M–H).

REFERENCE EXAMPLE 164

Methyl 3-[(2-Tetrahydropyranyl)oxy]-2-[(4-methoxybenzenesulfonyl)-(2-nitro-4-chlorobenzyl)amino]propionate To a mixture of 1.67 g (4.4 mmol) of (D,L) N-(4-methoxybenzenesulfonyl)-O-(2-tetrahydropyranyl) serine, methyl ester, 0.825 g (4.4 mol) of 4-chloro-2-nitrobenzyl alcohol and 1.16 g (4.4 mmol) of triphenylphosphine in 4.5 ml of tetrahydrofuran was added dropwise a solution of 0.766 g (4.4 mmol) of diethyl azodicarboxylate in 1 ml of tetrahydrofuran. The mixture was stirred at room temperature overnight and the solvent removed under vacuum. The residue was triturated with diethyl ether, filtered and the filtrate passed through a thin pad of hydrous magnesium silicate. The pad was washed with ethyl acetate and the total filtrate concentrated to dryness under vacuum to give 4.54 g of solid. The solid was chromatographed on silica gel with hexane-ethyl acetate (55:45) as solvent. The fractions containing product were combined and the solvent removed to give 0.55 g of oily solid; Mass spectrum (ES) 543.1 (M+H).

REFERENCE EXAMPLE 165

Methyl 2-{[2-(4-Pyridinylmethyleneamino)benzyl]-[4-methoxybenzenesulfonyl]amino}-3-hydroxypropionate A mixture of 0.50 g (1.268 mmol) of methyl 2-[(2-aminobenzyl)-(4-methoxy-benzenesulfonyl)amino]-3-hydroxypropionate and 1.268 mmol of 4-pyridinecarboxaldehyde in 7 ml of anhydrous ethanol was refluxed for 1.5 hours and the mixture concentrated under vacuum to dryness. To the residue was added H$_2$O and ethyl acetate.

The ethyl acetate layer was separated and concentrated to dryness under vacuum. The solid was purified by thick layer chromatography on silica gel with hexane-ethyl acetate as solvent to give 0.40 g of solid product (plus a small amount of starting material). Anal. for C$_{24}$H$_{25}$N$_3$O$_6$S: Calc'd: C, 59.6; H, 5.2; N, 8.7; Found: C, 57.6; H, 5.7; N, 7.4.

Mass spectrum (ES) 484 (M+H)-product; 395.1 (M+H)-starting material.

REFERENCE EXAMPLE 166

Methyl 1-(Cyclohexylcarbonyl)-4-(4-methoxybenzenesulfonyl)-2,3,4,5-tetrahydro-1H-[1,4]benzodiazepine-3-carboxylate To a solution of 0.80 g (1.64 mmol) of methyl 2-{[2-(cyclohexylcarbonyl)-aminobenzyl]-(4-methoxybenzenesulfonyl)amino}acrylate in 10 ml of methanol was added 0.207 g (2.46 mmol) of anhydrous sodium bicarbonate. The mixture was stirred for 2 days and then an additional 0.207 g of NaHCO$_3$ added. The mixture was stirred overnight and the solvent removed under vacuum. To the residue was added H$_2$O and ethyl acetate and the organic layer separated. The ethyl acetate extract was washed with brine, dried with Na$_2$SO$_4$ and the solvent removed under vacuum to give 0.83 g of the product as a yellow oil. Anal. for C$_{25}$H$_{30}$N$_2$O$_6$S: Calc'd: C, 61.7; H, 6.2; N, 5.8; Found: C, 61.0; H, 6.4; N, 5.3.

Mass spectrum (ES) 487.0 (M+H).

REFERENCE EXAMPLE 167

Methyl 3-Hydroxy-2-[(4-methoxybenzenesulfonyl)-(4-chloro-2-nitrobenzyl)amino]propionate To a solution of 0.289 g (1 mmol) of methyl 3-hydroxy-2-(4-methoxy-benzenesulfonylamino)propionate in 4 ml of N N-dimethylformamide cooled in an ice bath was added 40 mg of NaH (60% in oil) (1 mmol). After the gas evolution ceased, 0.165 g (1.1 mmol) of sodium iodide was added, followed by the addition of 0.226 g (1.1 mmol) of 4-chloro-2-nitrobenzyl chloride in 1 ml of dimethylformamide. The solution became purple and was stirred at room temperature over the weekend. The solvent was removed under vacuum and the residue extracted with CH$_2$Cl$_2$. The extract was washed with H$_2$O, brine and dried with Na$_2$SO$_4$. The solvent was removed to give 0.53 g of solid which was chromatographed on thick layer silica gel plates with hexane-ethyl acetate (2:1) as solvent to give 0.143 g (31%) of product, as crystals, m.p. 112°–114° C. Anal. for C$_{18}$H$_{19}$ClN$_2$O$_8$S: Calc'd: C, 47.2; H, 4.2; N, 6.1; Found: C, 47.0; H, 4.1; N, 6.0.

Mass spectrum (ES) 459.2 (M+H).

REFERENCE EXAMPLE 168

Methyl 3-Hydroxy-2-[(4-methoxybenzenesulfonyl)-(4-chloro-2-aminobenzyl)amino]propionate A mixture of 0.454 g (1 mmol) of methyl 3-hydroxy-2-[(4-methoxy-benzenesulfonyl)-(4-chloro-2-nitrobenzyl)amino]propionate and 0.451 g (2 mmol) of SnCl$_2$.2H$_2$O in 12 ml of methanol was refluxed for 2 hours. An additional 0.451 g (2 mmol) of SnCl$_2$.2H$_2$O was added and the mixture refluxed for 2 hours. The solvent was removed and ethyl acetate added. The mixture was neutralized with 1 N NaHCO$_3$ and then stirred for 1 hour and filtered. The ethyl acetate layer was separated and washed with H$_2$O, brine and dried with Na$_2$SO$_4$. The solvent was removed to give 0.42 g of solid which was chromatographed on thick layer silica gel plates with hexane-ethyl acetate (45:55) as solvent to give 60 mg of product (R$_f$0.66) as a glass, m.p. 99°–112° C. Anal. for C$_{18}$H$_{21}$ClN$_2$O$_6$S: Calc'd: C, 50.4; H, 4.9; N, 6.5; Found: C, 49.7; H, 4.9; N, 6.4.

Mass spectrum (ES) 429.1 (M+H).

REFERENCE EXAMPLE 169

Methyl 3-Hydroxy-2-[(4-methoxybenzenesulfonyl)-(4-chloro-2-aminobenzyl)amino]propionate To a solution of 0.458 g (1 mmol) of methyl 3-hydroxy-2-[(4-methoxy-benzenesulfonyl)-(4-chloro-2-nitrobenzyl)amino]propionate in 25 ml of ethanol and 25 ml of ethyl acetate was added 0.045 g of 10% Pd/C (wet –50% H$_2$O). The mixture was shaken in a Parr hydrogenator under 35 pounds per square inch of hydrogen for 3 hours. The mixture was filtered through diatomaceous earth and the filtrate was concentrated to dryness under vacuum to give 0.47 g of the product as a solid (approximately 90% pure). Thin layer chromatography on silica gel, NMR and Mass spectrum (ES) 429.1 (M+H) 395.1 (M+H) indicated approximately 10% of deschloro derivative.

A mixture of 4.74 g of methyl 3-hydroxy-2-[(4-methoxybenzenesulfonyl)-(4-chloro-2-aminobenzyl)amino} propionate, and 0.470 g of 10% Pd/C (wet –50% H$_2$O) in 200 ml of ethyl acetate-ethanol (1:1) was shaken in a Parr hydrogenator under 35 psi of hydrogen for 4 hours. The mixture was filtered through diatomaceous earth and the solvent removed to give 4.5 g of solid. The solid was chromatographed by HPLC on a Waters Prep machine with a 4×30 cm silica gel column with a step gradient of hexane-ethyl acetate (9:1 to 6:4 to 1:1 to 0:100) to give 1.56 g of a glass, m.p. 110°–123° C. Anal. for C$_{18}$H$_{21}$ClN$_2$O$_6$S: Calc'd: C, 50.4; H, 4.9; N, 6.5; Cl, 8.3; Found: C, 50.3; H, 4.8; N, 6.5; Cl, 7.8.

REFERENCE EXAMPLE 170

N-(4-Methoxybenzenesulfonyl)-glycine, Methyl Ester

To a mixture of 12.5 g (0.1 mol) of glycine, methyl ester hydrochloride in 120 ml of CH$_2$Cl$_2$, cooled in an ice bath was added 41.7 ml (0.3 mol) of triethylamine, followed by the dropwise addition of a solution of 20.65 g (0.1 mol) of 4-methoxy-benzenesulfonyl chloride in 40 ml of CH$_2$Cl$_2$. The mixture was stirred at room temperature overnight and poured into water. The organic layer was separated and washed with 2 N citric acid, H$_2$O, 1 N NaHCO$_3$, brine and dried with Na$_2$SO$_4$. The solvent was removed under vacuum to give 24.6 g of residue which was triturated with ethyl acetate to give 19.9 g of crystals, m.p. 59°–61° C. Anal. for C$_{10}$H$_{13}$NSO$_5$: Calc'd: C, 46.3; H, 5.1; N, 5.4; Found: C, 46.2; H, 5.0; N, 5.2.

REFERENCE EXAMPLE 171

Methyl 2-[(4-methoxybenzenesulfonyl)-(2-nitrobenzyl)anino]acetate

To a stirred and cooled mixture of 1.2 g (30 mmol) of NaH (58% in oil) in 50 ml of N,N-dimethylformamide was added dropwise a solution of 7.78 g (30 mmol) of N-(4-methoxybenzenesulfonyl)glycine, methyl ester in 40 ml of N,N-dimethylformamide. After gas evolution ceased, a solution of 6.80 g (32 mmol) of 2-nitrobenzyl bromide in 40 ml of N,N-dimethylformamide was added dropwise to the mixture. The mixture was then stirred at room temperature overnight under nitrogen and the solvent removed under vacuum. The residue was extracted with CH$_2$Cl$_2$ and the extract washed with H$_2$O, 2 N citric acid, H$_2$O, 1 N NaHCO$_3$, brine and dried with Na$_2$SO$_4$. The solution was filtered through a thin pad of hydrous magnesium silicate and the filter pad washed with CH$_2$Cl$_2$. The filtrate was concentrated under vacuum to give 11.79 g of solid. Trituration with ethyl acetate gave 2.64 g (22%) of crystals, m.p. 114° C.–116° C. Anal. for C$_{17}$H$_{18}$N$_2$O$_7$S: Calc'd: C, 51.8; H, 4.6; N, 7.1; Found: C, 51.7; H, 4.6; N, 7.1.

From the mother liquors an additional 6.49 g (55%) of product as crystals was obtained by chilling at 0C and filtering the mother liquors.

REFERENCE EXAMPLE 172

Methyl 2-[(2-Aminobenzyl)-(4-methoxybenzenesulfonyl)amino]acetate (A) To a mixture of 2.15 g (5.45 mmol) of methyl-2-[(4-methoxy-benzenesulfonyl)-(2-nitrobenzyl)amino]acetate and 1.57 g (25 mmol) of ammonium formate in 10 ml of anhydrous methanol was added 0.42 g of 10% palladium on carbon. The mixture was stirred at room temperature for 1.5 hours and then filtered through diatomaceous earth. The filtrate was concentrated to dryness under vacuum and the residue diluted with H$_2$O (25 ml) and extracted with CH$_2$Cl$_2$ (75 ml). The extract was washed with brine, dried with Na$_2$SO$_4$ and the solvent removed to give 0.45 g of solid. Crystallization from ethyl acetate gave 0.124 g of white crystals, m.p. 100°–102° C. Anal. for C$_{17}$H$_{20}$N$_2$O$_5$S: Calc'd: C, 56.0; H, 5.5; N, 7.7; Found: C, 56.1; H, 5.6; N, 7.6.

(B) To a solution of 4.2 g of methyl 2-[(4-methoxybenzenesulfonyl)-(2-nitrobenzyl)amino]acetate in 200 ml of ethanol-ethyl acetate (1:1) was added 0.42 g of 10% Pd on carbon (wet –50% H$_2$O) and the mixture shaken in a Parr hydrogenator under 35 pounds per square inch of hydrogen for 4.5 hours at room temperature. The mixture was filtered through diatomaceous earth and the filtrate concentrated to dryness under vacuum to give 4.0 g of crystals, m.p. 100°–102° C.

REFERENCE EXAMPLE 173

2-[(2-Aminobenzyl)-(4-methoxybenzenesulfonyl)amino]acetic Acid

To a solution of 5.14 g (14.1 mmol) of methyl 2-[(2-aminobenzyl)-(4-methoxybenzenesulfonyl)amino] acetate in 50 ml of methanol-tetrahydrofuran (1:1) was added 2.86 ml of 10 N NaOH and the mixture refluxed for 2 hours. The solvent was removed under vacuum and the residue partitioned between water and ether. The water layer was separated and acidified with 2 N citric acid. The solid was filtered, washed with H$_2$O and dried in a vacuum oven at room temperature to give 4.45 g (91%) of crystals, m.p. 145°–147° C. Anal. for C$_{16}$H$_{18}$N$_2$O$_5$S: Calc'd: C, 54.9; H, 5.2; N, 8.0; Found: C, 55.1; H, 5.2; N, 7.9.

REFERENCE EXAMPLE 174

Methyl 4-(4-Methoxybenzenesulfonyl)-1-(phenoxyacetyl)-2,3,4,5-tetrahydro-1H-[1,4]benzodiazepine-3-carboxylate To a cooled (0° C.) mixture of 1.5 g (3.8 mmol) of methyl 2-[(2-aminobenzyl)-(4-methoxybenzenesulfonyl)amino]-3- hydroxypropionate and 2.7 ml (19 mmol) of triethylamine in 15 ml of $CH_2Cl_2$ was added 1.58 g (11.4 mol) of phenoxyacetyl chloride. The mixture was stirred at room temperature overnight and filtered. The filtrate was washed with $H_2O$, 2 N citric acid, and brine and dried with $Na_2SO_4$. The solvent was removed to give 2.4 g of crude methyl 2-{(4-methoxybenzenesulfonyl)-[2-(phenoxyacetylamino)benzyl]amino}acrylate as an oil. Anal. for $C_{26}H_{26}N_2O_7S$: Calc'd: C, 61.2; H, 5.1; N, 5.5; Found: C, 62.6; H, 5.1; N, 4.0.

Mass spectrum (ES) 511 (M+H).

To a 2.0 g (3.92 mmol) sample of the preceding compound in 15 ml of methanol was added 0.494 g of anhydrous $NaHCO_3$ and the mixture stirred for 5 hours. The mixture was concentrated under vacuum and ethyl acetate and $H_2O$ were added to the residue. The mixture was filtered and the organic layer of the filtrate separated, washed with brine and dried with $Na_2SO_4$. The solvent was removed to give 0.36 g of product as off-white crystals, m.p. 151°–153° C. Anal. for $C_{26}H_{26}N_2O_7S$: Calc'd: C, 61.2; H, 5.1; N, 5.5; Found: C, 61.1; H, 5.1; N, 5.4.

Mass spectrum (ES) 511 (M+H).

REFERENCE EXAMPLE 175

3-hydroxymethyl-4-(4-Methoxybenzenesulfonyl)-1-(3-pyridinylmethyl)-2,3,4,5-tetrahydro-1H-[1,4]benzodiazepine A mixture of 0.100 g (0.208 mmol) of methyl 4-(4-methoxybenzenesulfonyl)-1-(3-pyridinylcarbonyl)-2,3,4,5-tetrahydro-1 H-[1,4]benzodiazepine-3-carboxylate and 3 ml of borane-tetrahydrofuran complex in tetrahydrofuran (1.0 M) was refluxed overnight. The solution was cooled to room temperature, diluted with methanol and the solvent removed. Methanol was added several times and, after each addition, the solvent was removed. To the residue was added IN $NaHCO_3$. The mixture was stirred for 45 minutes and then extracted with ethyl acetate. The extract was concentrated and then washed with $H_2O$, brine and dried with $Na_2SO_4$. The solvent was removed under vacuum and the residue chromatographed on thick layer silica gel plates with 10% methanol in ethyl acetate as solvent to give 60 mg of solid ($R_f$0.26). Crystallization from ethyl acetate gave 30 mg of white crystals. Anal. for $C_{23}H_{25}N_3O_4S$: Calc'd: C, 62.8; H, 5.7; N, 9.6; S, 7.3; Found: C, 61.1; H, 5.6; N, 9.2; S, 7.3.

Mass spectrum (ES) 440.2 (M+H).

REFERENCE EXAMPLE 176

Methyl 4-(4-Methoxybenzenesulfonyl)-1-(2-methoxypyridinyl-3-carbonyl)-2,3,4,5-tetrahydro-1H-[1,4]benzodiazepine-3-carboxylate To a cooled (0° C.) mixture of 1.0 g (2.54 mmol) of methyl 2-[(2-aminobenzyl)-(4-methoxybenzenesulfonyl)amino]-3-hydroxypropionate and 1.8 ml (12.68 mmol) of triethylamine in 10 ml of $CH_2Cl_2$ was added 0.957 g (5.58 mmol) of 2-methoxypyridine-3-carbonyl chloride in 4 ml of $CH_2Cl_2$. The solution was stirred at room temperature overnight, diluted with $H_2O$ and $CH_2Cl_2$ and the organic layer separated. The organic layer was washed with $H_2O$, 2 N citric acid, and brine and dried with $Na_2SO_4$. The solvent was removed under vacuum to give 1.2 g of solid. The solid was chromatographed on thick layer silica gel plates with ethyl acetate-hexane (3:1) as solvent to give 0.27 g of yellow foam. Anal. for $C_{25}H_{25}N_3O_7S$: Calc'd: C, 58.7, H, 4.93; N, 8.21; Found: C, 57.8; H, 4.5; N, 8.3; S, 6.2.

REFERENCE EXAMPLE 177

5-Methyl-2-nitrobenzyl Bromide

To a cooled (ice-water bath) mixture of 30% HBr in acetic acid (3 ml) was added 2.5 g 5-methyl-2-nitrobenzyl alcohol and the chilled solution stirred for 2 hours. The mixture was poured into ice-water and extracted with diethyl ether. The extract was washed with $H_2O$, brine and the solvent removed under vacuum to give a mixture of product (50%) and starting material (50%).

REFERENCE EXAMPLE 178

Methyl 3-Hydroxy-2-[(4-methoxybenzenesulfonyl)-(5-methyl-2-nitrobenzyl)amino]propionate A solution of 23.14 g (0.08 mol) of methyl 3-hydroxy-2-(4-methoxy-benzenesulfonylamino)propionate in 120 ml of dry N,N-dimethylformamide was added dropwise to a stirred suspension of 3.2 g (0.08 mol) of sodium hydride (57% in oil) in 120 ml of N, N-dimethylformide. When gas evolution ceased, the mixture was chilled in an ice bath and a solution of 16.4 g (0.084 mol) of 5-methyl-2-nitrobenzyl chloride in 100 ml of N,N-dimethylformamide was added. To the mixture was added 12.6 g (0.084 mol) of anhydrous sodium iodide and the mixture was chilled in an ice bath and stirred for 20 minutes. The mixture was allowed to warm to room temperature and was stirred overnight. The solvent was removed under vacuum and the residue diluted with 200 ml of $H_2O$ and extracted with 500 ml of ethyl acetate. The aqueous layer was extracted with an additional 200 ml of ethyl acetate. The combined extract was washed with $H_2O$, brine and dried with $Na_2SO_4$. The solvent was removed to give 41.18 g of crude product. The product was chromatographed on silica gel with hexane-ethyl acetate (1:1) as solvent to give 8.14 g ($R_f$0.38) of product as a yellow semi-solid. From a small scale run (1 mmol) the product was chromatographed twice on thick silica gel plates with hexane-ethyl acetate (1:1) to give 0.12 g of a yellow semi-solid. Anal. for $C_{19}H_{22}N_2SO_8$: Calc'd: C, 52.0; H, 5.1; N, 6.4; Found: C, 51.7; H, 5.1; N, 6.0.

REFERENCE EXAMPLE 179

Methyl 3-Hydroxy-2-[(4-methoxybenzenesulfonyl)-(2-anino-5-methylbenzyl)amino]propionate To a solution of 3.4 g of methyl 3-hydroxy-2-[(4-methoxybenzenesulfonyl)-(5-methyl-2-nitrobenzyl)-amino]propionate in 200 ml of ethanol-ethyl acetate (1:1) was added 0.34 g of 10% palladium on carbon (wet –50% $H_2O$). The mixture was then shaken in a Parr hydrogenator under 35 psi of hydrogen for 2.5 hours. The mixture was filtered through diatomaceous earth and the filtrate concentrated under vacuum to give 2.86 g of a brown oil. Anal. for $C_{19}H_{24}N_2O_6S$: Calc'd: C, 55.9; H, 5.9; N, 6.9; Found: C, 55.6; H, 5.9; N, 6.4.

Mass spectrum (ES) 409 (M+H).

REFERENCE EXAMPLE 180

Methyl 3-[(2-Tetrahydropyranyl)oxy]-2-[(-4-methoxybenzenesulfonyl)-(5-methyl-2-nitrobenzyl)anino]propionate To a mixture of 1.75 g (4.68 mmol) of (D,L)N-(4-methoxybenzenesulfonyl)-O-(2-tetrahydropyranyl) serine, methyl ester, 0.790 g (4.68 mmol) of 5-methyl-2-nitrobenzyl alcohol and 1.23 g (4.68 mmol) of triphenylphosphine in anhydrous tetrahydrofuran was added dropwise (over 15 minutes) a solution of 0.815 g (4.68 mmol) of diethyl azodicarboxylate (DEAD) in 1 ml of tetrahydrofuran. The mixture was stirred at room temperature overnight and the solvent removed under vacuum. The residue was triturated with diethyl ether and the solid filtered off. The filtrate was concentrated to dryness under vacuum to give 4.67 g of solid. The solid was chromatographed on silica gel with hexane-ethyl acetate (1:1) to give 0.56 g of product ($R_f$ 0.48).

REFERENCE EXAMPLE 181

Methyl 1-Methoxyacetyl-4-(4-methoxybenzenesulfonyl)-7-methyl-2,3,4,5-tetrahydro-1H-[1,4]benzodiazepine-3-carboxylate To a cooled (0° C.) mixture of 1.598 g (3.91 mmol) of methyl 3-hydroxy-2-[(4-methoxybenzenesulfonyl)-(2-amino-5-methylbenzyl)amino]propionate and 1.97 g (19.5 mmol) of triethylamine in 15 ml of dichloromethane was added 0.787 ml (8.60 mmol) of methoxyacetylchloride. The mixture was stirred at room temperature overnight. The mixture was then diluted with $CH_2Cl_2$ and washed with $H_2O$, 2 N citric acid, $H_2O$, brine and dried with $Na_2SO_4$. The solution was filtered through a thin pad of hydrous magnesium silicate and the filtrate concentrated to give 1.94 g of crude methyl 2-{[2-(methoxyacetylamino)-5-methylbenzyl]-(4-methoxy-benzene-sulfonyl)-amino}acrylate as a brown oil. Mass spectrum (ES) 463.4 (M+H).

To a solution of 1.62 g (3.5 mmol) of the preceding compound in 15 ml of anhydrous methanol was added 0.382 g (4.50 mmol) of anhydrous $NaHCO_3$ and the mixture was stirred overnight at room temperature. The solvent was removed under vacuum and the residue partitioned between 100 ml of ethyl acetate and 20 ml of water. The ethyl acetate layer was separated and washed with $H_2O$, brine and dried with $Na_2SO_4$. The solution was filtered through a thin pad of hydrous magnesium silicate and the filtrate concentrated under vacuum to give a yellow oil. Trituration with ethyl acetate-hexane gave 1.26 g (78%) of tan crystals, m.p. 122°–124° C. Anal. for $C_{22}H_{26}N_2O_7S$: Calc'd: C, 57.1; H, 5.7; N, 6.1; Found: C, 57.4; H, 5.7; N, 6.0.

REFERENCE EXAMPLE 182

Methyl 1-Benzoyl-4-(4-methoxybenzenesulfonyl)-7-methyl-2,3,4,5-tetrahydro-1H-[1,4]benzodiazeprine-3-carboxylate To a cooled (0° C.) mixture of 1.465 g (3.586 mmol) of methyl 3-hydroxy-2-[4-methoxybenzenesulfonyl)-(2-amino-5-methylbenzyl)amino]propionate and 2.49 ml (17.93 mmol) of triethylamine in 20 ml of $CH_2Cl_2$ was added 0.915 ml (7.89 mmol) of benzoyl chloride. The mixture was stored at room temperature overnight, diluted with $CH_2Cl_2$ and washed with $H_2O$, 2 N citric acid, $H_2O$, brine and dried with $Na_2SO_4$. The solution was filtered through a thin pad of hydrous magnesium silicate and the filtrate concentrated under vacuum to give 1.8 g of crude methyl 2-[(2-benzoylamino-5-methylbenzyl)-(4-methoxybenzenesulfonyl)amino]acrylate as a brown oil. Anal. for $C_{26}H_{26}N_2O_6S$: Calc'd: C, 63.1; H, 5.3; N, 5.7; Found: C, 63.9; H, 5.2; N, 5.2.

As described for Reference Example 181, 1.825 g (3.68 mmol) of the preceding compound was stirred with 0.402 g (4.78 mmol) of $NaHCO_3$ in 1.5 ml of methanol to give an oil. Trituration with hexane (plus several drops of ethyl acetate) gave crystals, m.p. 58°–62° C.

REFERENCE EXAMPLE 183

Methyl 1-(trans-Crotonyl)-4-(4-methoxybenzenesulfonyl)-7-methyl-2,3,4,5-tetrahydro-1H-[1,4]benzadiazepine-3-carboxylate As described for Reference Examples 181 and 182, a mixture of 1.41 g (3.455 mmol) of methyl 3-hydroxy-2-[-(4-methoxybenzenesulfonyl)-(2-amino-5-methyl-benzyl)amino]propionate, 1.75 g (17.3 mmol) of triethylamine and 0.809 ml of trans-crotonyl chloride in 15 ml of $CH_2Cl_2$ was stirred overnight to give 1.52 g of methyl 2-{[2-(trans-crotonylamino)-5-methylbenzyl]-(4-methoxybenzenesulfonyl) amino acrylate as a brown oil; Mass spectrum (ES) 459.4 (M+H).

As described in Reference Example 181, 1.52 g (3.31 mmol) of the preceding product was stirred with 0.362 g (4.3 mmol) of $NaHCO_3$ in 15 ml of methanol at room temperature overnight. To the mixture was added 0.056 g of $NaHCO_3$ and the mixture was heated at 80° C. for 3 hours and worked up as for Reference Example 181 to give a 1.05 g of a yellow glass, m.p. 75°–84° C. Mass spectrum (ES) 459.4 (M+H).

REFERENCE EXAMPLE 184

1-(trans-Crotonyl)-4-(4methoxybenzenesufonyl)-7-methyl-2,3,4,5-tetrahydro-1H-[1,4]benzodiazepene-3-carboxylic acid A mixture of 1.26 g (2.72 mmol) of methyl 1-(trans-crotonyl)-4-(4-methoxybenzenesulfonyl)-7-methyl-2,3,4,5-tetrahydro-1H-[1,4]benzodiazepine-3-carboxylate and 3.53 ml (3.53 mmol) of 1 N NaOH in 10 ml of tetrahydrofuran was stirred at room temperature for 3 hours. The solvent was removed under vacuum and the residue dissolved in $H_2O$ and the solution extracted with ethyl acetate. The aqueous layer was acidified with 1$\underline{N}$ HCl (pH 2) and extracted with $CH_2Cl_2$. The $CH_2Cl_2$ extract was dried with $Na_2SO_4$ and the solvent removed to give 1.06 g (after drying under vacuum) of solid, m.p. 101°–105° C.

REFERENCE EXAMPLE 185

1-(Benzoyl)-4-(4-methoxybenzenesulfonyl)-7-methyl-2,3-4,5-tetrahydro-1H-[1,4]benzodiazepine-3-carboxylic acid A mixture of 1.18 g (2.38 mml) of methyl 1-(benzoyl)-4-(4-methoxy-benzenesulfonyl)-7-methyl-2,3,4,5-tetrahydro-1H-[1,4]benzodiazepine-3-carboxylate and 3.09 ml (3.09 mmol) of 1N NaOH in 10 ml of tetrahydrofuran was stored at room temperature overnight and the solvent removed under vacuum. The residue was diluted with $H_2O$, extracted with ethyl acetate and the aqueous layer acidified with 2N citric acid. The mixture was extracted with $CH_2Cl_2$ and the $CH_2Cl_2$ extracts were washed with $H_2O$, brine and dried with $Na_2SO_4$. The solvent was removed to give 0.82 g of a light yellow glass, m.p. 95°–100° C.; Mass spectrum (ES) 481.4 (M+H).

REFERENCE EXAMPLE 186

Methyl 4-(4-Methoxybenzenesulfonyl)-1-(2-methoxyethyl)-2,3,4,5-tetrahydro-1H-[1,4]benzodiazepine-3-carboxylate A mixture of 1.6 g (3.57 mmol) of methyl 1-(methoxyacetyl)-4-(4-methoxybenzenesulfonyl)-2,3,4,5-tetrahydro-1H-[1,4]benzodiazepine-3-carboxylate and 32 ml of borane in tetrahydrofuran (1.0 M) was refluxed under nitrogen overnight. Methanol was added and the solvent removed. To the residue was added 25 ml of $CH_2Cl_2$ and 25 ml of 2 N HCl and the mixture stirred at room temperature for 1 hour. The organic layer was separated and washed with $H_2O$ and concentrated to dryness. The residue was triturated with ethyl acetate-hexane, cooled and filtered to give 1.2 g of white crystals, m.p. 86°–90° C.; Mass spectrum (ES) 435.4 (M+H). Anal. for $C_{21}H_{26}N_2O_6S$: Calc'd: C, 58.1; H, 6.0; N, 6.5; Found: C, 58.5; H, 6.0; N, 6.5.

REFERENCE EXAMPLE 187

4-(4-Methoxybenzenesulfonyl)-1-(2-methoxyethyl)-2,3,4,5-tetrahydro-1H-[1,4]benzodiazepine-3-carboxylic acid A mixture of 1.0 g (2.3 mmol) of methyl 4-(4-methoxybenzenesulfonyl)-1-(2-methoxyethyl)-2,3,4,5-tetrahydro-1H-[1,4]benzodiazepine-3-carboxylate and 3.0 ml of 1 N NaOH in 10 ml of tetrahydrofuran was stirred at room temperature for 2 hours and the solvent removed. To the residue was added water and the mixture acidified with 1 N HCl. The mixture was extracted with ethyl acetate and the extract was washed with brine and dried with $Na_2SO_4$. The solvent was removed and the residue triturated with ethyl acetate-hexane, cooled and filtered to give 0.65 g of white crystals, m.p. 164°–165° C.; Mass spectrum (ES) 421.4 (M+H). Anal. for $C_{20}H_{24}N_2O_6S$: Calc'd: C, 57.1; H, 5.8; N, 6.7; Found: C, 57.3; H, 5.7; N, 6.4.

REFERENCE EXAMPLE 188

Methyl 1-(Benzyl)-4-(4-methoxybenzenesulfonyl)-2,3,4,5-tetrahydro-1H-[1,4]benzodiazepine-3-carboxylate A mixture of 0.20 g (0.416 mmol) of methyl 1-(benzoyl)-4-(4-methoxybenzenesulfonyl)-2,3,4,5-tetrahydro-1H-[1,4]benzodiazepine-3-carboxylate and 4 ml of borane in tetrahydrofuran (1.0 M) was refluxed overnight and the solvent removed. To the residue was added 5 ml of $CH_2Cl_2$ and 5 ml of 2N HCl and the mixture stirred for 1 hour. The organic layer was separated and concentrated to dryness. The residue was chromatographed on thick layer silica gel plates with hexane-ethyl acetate (2:1) as solvent to give 0.140 g of a colorless oil; Mass spectrum (ES) 467.5 (M+H).

REFERENCE EXAMPLE 189

4-(4-Methoxybenzenesulfonyl)-1-[4-(trifluoromethoxy)benzoyl-8-chloro-2,3,4,5-tetrahydro-1H-[1,4]benzodiazepine-3-carboxylic acid As described for Reference Example 18, 1.46 g (3.40 mmol) of methyl 2-[(2-amino-4-chlorobenzyl)-(4-methoxybenzenesulfonyl)amino]-3-hydroxypropionate was reacted with 4-(trifluoromethoxy)benzoyl chloride to give 2.59 g of methyl 2-{2-[4-(trifluoromethoxy) benzoyl]amino-4-chlorobenzyl]amino}acrylate as a yellow oil; Mass spectrum (ES) 599.3 (M+H). The preceding compound was stirred with 0.445 g (5.29 mmol) of anhydrous $NaHCO_3$ in 15 ml of methanol at room temperature for 16 hours and then was heated at 80° C. for 2 hours. The solvent was removed and the residue extracted with ethyl acetate. The extract was washed with $H_2O$, brine, and dried ($Na_2SO_4$). The solvent was removed and the residue crystallized from ethyl acetate-hexane to give methyl 4-(4-methoxybenzenesulfonyl)-1-[4-(trifluoro-methoxy)benzoyl }-8-chloro-2,3,4,5-tetrahydro-1H-[1,4]benzodiazepine-3-carboxylate as yellow crystals, m.p. 149°–151° C. Anal. for $C_{26}H_{22}ClF_3O_7S$: Calc'd: C, 52.1; H, 3.7; N, 4.7; Cl, 6.0; F, 9.5; Found: C, 51.8; H, 3.6; N, 4.7; Cl, 5.9; F, 9.4.

1.58 g (2.64 mmol) of the preceding compound was stirred with 3.43 ml of 1N NaOH in 10 ml of tetrahydrofuran at room temperature for 2 hours and worked up as for Reference Example 104 to give 1.52 g of product. Crystallization from ethyl acetate-hexane gave 1.2 g of white crystals, m.p. 184°–186° C.

REFERENCE EXAMPLE 190

Methyl 4-(4-Methoxybenzenesulfonyl)-1-(4-morpholinoacetyl)-2,3,4,5-tetrahydro-1H-[1,4]benzodiazepine-3-carboxylate A mixture of 0.10 g (0.22 mmol) of methyl 1-(chloroacetyl)-4-(4-methoxybenzenesulfonyl)-2,3,4,5-tetrahydro-1H-[1,4]benzodiazepine-3-carboxylate, 21.2≈|l of morpholine and 125.4≈|1 of N,N-diisopropylethylamine in 3 ml of $CH_2Cl_2$ was stirred overnight at room temperature. An additional 2.2≈|l of morpholine was added and the solution stirred for 2 days at room temperature. The mixture was diluted with $CH_2Cl_2$ and washed with $H_2O$, brine and dried with $Na_2SO_4$. The solvent was removed to give the product as a solid, Mass spectrum (ES) 504.3 (M+H). Anal. for $C_{24}H_{29}N_3O_7S$: Calc'd: C, 57.2; H, 5.8; N, 8.3; Found: C, 56.5; H, 5.6; N, 8.1.

REFERENCE EXAMPLE 191

Methyl 4-(4-Methoxybenzenesulfonyl)-1-[2-(1-pyrazolyl)phenylcarbonyl]-7-methyl-2,3,4,5-tetrahydro-1H-[1,4]benzodiazepine-3-carboxylate As described for the general reaction of ethyl 2-fluorobenzoate with amines set forth in *Tetrahedron*, 53, 7557–7576 (1997), ethyl 2-fluorobenzoate was reacted with pyrazole by refluxing N, N-dimethylformamide to give ethyl 2-(1-pyrazolyl)benzoate, as a thick yellow oil. Anal. Calc'd: for $C_{12}H_{12}N_2O_2$: C, 66.7,H, 5.6; N 13.0: Found: C, 66.5:H, 5.4: N, 12.9; Mass spectrum (ES) 217.2 (M+H). A sample (7.02 g) of this compound and 8.42 ml of 5N NaOH in 40 ml of ethanol-tetrahydrofuran (2:1) was refluxed for 2 hrs and the solvent removed. The residue was made acidic (pH6) with 2N citric acid and the precipated solid was filtered to obtain 3.7 g of product. The pH of the filtrate was adjusted to 4.5 and extracted with ethyl acetate. The extract was concentrated to dryness to give 1.5 g of product. The two crops were combined to give 5.2 g of 2-(1-pyrazolyl) benzoic acid, mp 140–142° C. To the preceding compound (2.07 g) in 5 ml $CH_2Cl_2$ (chilled in an ice bath) was added 11.1 ml of a 2 Molar solution of oxalyl chloride in $CH_2Cl_2$ and 0.085 ml of N,N-dimethylformamide. The mixture was allowed to warm to room temperature and stirred for 4 hours. The solvent was removed and 25 ml of toluene added (twice) and removed under vacuum to give 2-(1-pyrazolyl) benzoyl chloride as a yellow solid.

A 2.3 g sample of the preceding compound was reacted with 1.5 g of the compound of Reference Example 179 in 15 ml of $CH_2Cl_2$ and 5.12 ml of triethylamine in the manner described for Reference Example 181 to give methyl 2-[(4-methoxybenzenesulfonyl)-{2-[2-(1-pyrazolyl) phenylcarbonyl]amino-5-methylbenzyl}amino]acrylate. This compound was cyclized with $NaHCO_3$ in methanol in the manner described in Reference Example 181 to give methyl 4-(4-methoxybenzenesulfonyl)-1-[2-(1-pyrazolyl) phenylcarbonyl]-7-methyl-2,3,4,5-tetrahydro-1H-[1,4] benzodiazepine-3-carboxylate, m.p. 240–242° C.

A 1.16 g sample of the preceding compound was hydrolysed with 2.69 ml of 1N NaOH in 10 ml of tetrahydrofuran in the manner described for Reference Example 104 to give 0.71 g of 4-(4-methoxybenzenesulfonyl)-1-[2-(1-pyrazolyl) phenyl-carbonyl)-7-methyl-2,3,4,5-tetrahydro-1H-[1,4] benzodiazepine-3-carboxylic acid, mp 149–151° C.

REFERENCE EXAMPLE 192

Methyl 4-(4-Methoxybenzenesulfonyl)-1-[2-(4-morpholino)phenylcarbonyl}-8-chloro-2,3,4,5-tetrahydro-1H-[1,4]benzodiazepine-3-carboxylate Ethyl 2-morpholinobenzoate prepared in the manner described in *Tetrahedron,* 53:7557, (1997) was refluxed with 10 N NaOH in tetrahydrofuran-ethanol (8:2) for 1.5 hrs to give 2-morpholinobenzoic acid, mp 156–157° C. A 1.8 g sample of this compound in 5 ml of $CH_2Cl_2$ (chilled) was added a solution of 7.9 ml of oxalyl chloride in $CH_2Cl_2$ (2M) followed by the addition of 0.058 ml of N,N-dimethylformamide. The solution was stirred at room temperature for 6 hrs and the solvent removed. Toluene was added (2 times) and removed to give 2-(4-morpholino) benzoyl chloride as a yellow solid.

In the manner described in Reference Examples 181 and 189, the preceding 2-(4-morpholino)benzoyl chloride was reacted with methyl 2-[(2-amino-4-chlorobenzyl)-(4-methoxybenzenesulfonyl)amino]-3-hydroxypropionate and the product was stirred with $NaHCO_3$ in methanol to give methyl 4-(4-methoxybenzenesulfonyl)-1-[2-(4-morpholino) phenylcarbonyl]-8-chloro-2,3,4,5-tetrahydro-1H-[1,4] benzodiazepine-3-carboxylate, as a white solid having a mp 100–105° C.

To 0.90 g of this compound in 10 ml of tetrahydrofuran was added 1.95 ml of 1 N NaOH and the solution was stirred at room temperature overnight. Acidification with 2N citric acid gave 0.82 g of solid, mp 136–143° C. [compound, 4-(4-methoxybenzenesulfonyl)-1-[2-(4-morpholino) phenylcarbonyl]-8-chloro-2,3,4,5-tetrahydro-1H-[1,4] benzodiazepine-3-carboxylic acid].

REFERENCE EXAMPLE 193

Methyl 1-(4-Ethoxybenzoyl)-4-(4-methoxybenzenesulfonyl)-2,3,4,5-tetrahydro-1H-[1,4]benzodiazepine-3-carboxylate A mixture of 0.270 g of methyl 4-(4-methoxybenzenesulfonyl)-2,3,4,5-tetrahydro-1H-[1,4] benzodiazepine-3-carboxylate of Reference Example 12, 0.291 g of 4-ethoxybenzoyl chloride and 500 μl of triethylamine in 5 ml of $CH_2Cl_2$ was stirred at room temperature overnight. The mixture was diluted with $CH_2Cl_2$ and $H_2O$ and the $CH_2Cl_2$ layer was separated and concentrated to dryness. The residue was triturated with ethyl acetate to give 0.276 g of methyl 1-(4-ethoxybenzoyl)-4-(4-methoxybenzenesulfonyl)-2,3,4,5tetrahydro-1H-[1,4] benzodiazepine-3-carboxylate as white crystals, mp 187–190° C.

A 0.47 g sample of this compound was hydrolyzed with 1.2 ml of 1N NaOH in 4 ml of tetrahydrofuran. Dilution with $H_2O$ and acidification with 1N HCl gave 0.40 g of the acid as a white solid, mp 144–152° C.

REFERENCE EXAMPLE 194

Methyl 4-(4-Methoxybenzenesulfonyl)-1-[2-chloro-4-(3-methyl-1-pyrazolyl)phenylcarbonyl}-2,3,4,5-tetrahydro -1H-[1,4]benzodiazepine-3-carboxylate As described in Example 65, methyl 4-(4-methoxybenzenesulfonyl)-2,3,4,5-tetrahydro-1H-[1,4] benzodiazepine-3-carboxylate was reacted with 4-(3-methyl-1-pyrazolyl)-2-chlorobenzoyl chloride to give methyl 4-(4-methoxybenzenesulfonyl)-1-[2-chloro-4-(3-methyl-1-pyrazolyl)phenylcarbonyl]-2,3,4,5-tetrahydro-1H-[1,4]benzodiazepine-3-carboxylate as a white solid. Anal. for $C_{29}H_{27}ClN_4O_6S$: Calc'd: C, 58.3; H, 4.6; N, 9.4. Found: C, 58.2; H, 4.9; N, 8.9.

This compound was hydrolysed with 1N NaOH in tetrahydrofuran as described in Reference Example 185 to give the benzodiazepine-3-carboxylic acid derivative as a white solid.

REFERENCE EXAMPLE 195

1-Benzyl-4-(4-methoxybenzenesulfonyl)-2,3,4,5-tetrahydro-1H-[1,4]benzodiazepine-3-carboxylic acid A mixture of 1.7 g of the compound of Reference Example 45 and 25 ml of borane in tetrahydrofuran (1.0 Molar) was refluxed under nitrogen overnight. To the solution was added 5 ml of $CH_3OH$, $CH_2Cl_2$ (40 ml) and 30 ml of 2N HCl and the mixture stirred at room temperature for 1.5 hr. The organic layer was separated, washed with brine, dried with $Na_2SO_4$ and the solvent removed. The residue was crystallized from ethanol-hexane to give 1.15 g of methyl 1-benzyl-4-(4-methoxybenzenesulfonyl)-2,3,4,5-tetrahydro-1H-[1,4]benzodiazepine-3-carboxylate as white crystals, mp 120–122° C. A sample (1.0 g) of this compound was hydrolysed with 2.8 ml of 1 N NaOH in 7 ml of tetrahydrofuran as described in Reference Example 104 to give 0.64 g of the 2,3,4,5-tetrahydro-1H-[1,4] benzodiazepine-3-carboxylic acid derivative as white crystals, mp 183–185° C.

REFERENCE EXAMPLE 196

Methyl 1-(2,4-Dimethoxybenzoyl)-4-(4-methoxybenzenesulfonyl)-2,3,4,5-tetrahydro-1H-[1,4]benzodiazepine-3-carboxylate To a cooled (0° C.) solution of 1.0 g (2.66 mmol) of 4-(4-methoxybenzenesulfonyl)-2,3,4,5-tetrahydro-1H-[1,4]

benzodiazepine-3-carboxylate from Reference Example 12 and 1.85 ml (13.3 mmol) of triethylamine in 8 ml of $CH_2Cl_2$ was added 1.17 g (6.65 mmol) of 2,4-dimethoxybenzoyl chloride. The mixture was stirred at room temperature overnight, diluted with $CH_2Cl_2$ and washed with 2 N citric acid. The organic layer was washed with $H_2O$, 1 N $Na_2CO_3$, brine and dried over $Na_2SO_4$. The solvent was removed and the residue was chromatographed on thick layer silica gel plates with ethyl acetate-hexane (1:1) as an eluent to give 1.0 g of methyl 1-(2,4-dimethoxybenzoyl)-4-(4-methoxybenzenesulfonyl)-2,3,4,5-tetrahydro-1H-[1,4]benzodiazepine-3-carboxylate as a white foam. Anal. for $C_{27}H_{28}H_2O_8S$: Calc'd: C, 60.0; H, 5.2; N, 5.2; Found: C, 60.0; H, 5.2; N, 5.1.

Mass Spectrum (ES): 541.0 (M+H).

A 0.80 g (1.48 mmol) sample of the preceding compound and 1.92 ml (1.92 mmol) of 1 N NaOH in 5 ml of tetrahydrofuran was stirred at room temperature for 1.5 hours. The solvent was removed and the residue diluted with water. The solution was acidified with 1 N HCl, chilled and filtered to give 0.70 g of 1-(2,4-dimethoxy-benzoyl)-4-(4-methoxybenzenesulfonyl)-2,3,4,5-tetrahydro-1H-[1,4]benzodiazepine-3-carboxylic acid as a white solid. Anal. for $C_{26}H_{26}N_2O_8S$: Calc'd: C, 59.3; H, 5.0; N, 5.3; Found: C, 56.1; H, 4.8; N, 5.0.

Mass Spectrum (ES): 527.0 (M+H).

REFERENCE EXAMPLE 197

Methyl 4-(4-Methoxybenzenesulfonyl)-1-[2-(4-methylpiperazin-1-yl)acetyl]-2,3,4,5-tetrahydro-1H-[1,4]benzodiazepine-3-carboxylate To a mixture of 2.5 g (6.64 mmol) of methyl 4-(4-methoxybenzenesulfonyl)-2,3,4,5-tetrahydro-1H-[1,4]benzodiazepine-3-carboxylate (Reference Example 12) and 4.63 ml (33.2 mmol) of triethylamine in 40 ml of $CH_2Cl_2$ cooled to 0° C. was added to 1.65 g (14.63 mmol) of chloroacetyl chloride. The solution was stirred at room temperature for 2 days, chilled to 0° C. and 926 µl of triethylamine and 750 mg of chloroacetyl chloride were added thereto. The mixture was stirred at room temperature overnight, diluted with $CH_2Cl_2$ and $H_2O$. The insoluble solid was filtered off. The organic layer of the filtrate was separated, washed with brine, dried with $Na_2SO_4$ and filtered through diatomaceous earth. The solvent was removed and the residue triturated with ethyl acetate and a trace of ethanol. Chilling and filtering gave 0.75 g of methyl 1-(chloroacetyl)-4-(4-methoxybenzenesulfonyl)-2,3,4,5-tetrahydro-1H-[1,4]benzo-diazepine-3-carboxylate (Reference EXample 91). Anal. for $C_{20}H_{21}ClN_2O_6S$: Calc'd: C, 53.0; H, 4.7; N, 6.2; Found: C, 51.6; H, 4.6; N, 5.7.

Mass Spectrum (ES): 453.0 (M+H).

To a solution of 1.4 g (3.09 mmol) of the preceding compound in 12 ml of $CH_2Cl_2$ cooled to 0° C. was added 1.2 ml (6.79 mmol) of N,N-diisopropylethylamine followed by the addition of 753.2 µl (6.79 mmol) of 1-methylpiperazine. The mixture was stirred at room temperature overnight, diluted with $CH_2Cl_2$, and washed with 2 N citric acid, $H_2O$, 1 M $NaHCO_3$, brine and dried ($Na_2SO_4$). The citric acid wash was made basic with saturated $NaHCO_3$ and then extracted with $CH_2Cl_2$. The extract was dried over $Na_2SO_4$ and the solvent removed under vacuum to give 1.10 g of methyl 4-(4-methoxybenzenesulfonyl)-1-[2-(4-methylpiperazin-1-yl)acetyl]-2,3,4,5-tetrahydro-1H-[1,4]benzodiazepine-3-carboxylate as a white glass.

A mixture of 1.0 g (1.94 mmol) of the preceding compound and 2.3 ml (2.3 mmol) of 1 N KOH in 5 ml of methanol was stirred at room temperature for 2 hours. The solvent was removed under vacuum. To the residue was added toluene (2 times) and the solvent removed under vacuum after each addition. The solid was dried at 65°0 C. under vacuum for 6 hours to give 1.1 g of potassium 4-(4-methoxy-benzenesulfonyl)-1-[2-(4-methylpiperazin-1-yl)acetyl]-2,3,4,5-tetrahydro-1H-[1,4]benzodiazepine-3-carboxylate as a white solid.

REFERENCE EXAMPLE 198

Methyl 1-Acetyl-4-(4-hydroxybenzenesulfonyl)-2,3,4,5-tetrahydro-1H-[1,4]benzodiazepine-3-carboxylate To a cooled (0°) solution of 2.0 g (4.78 mmol) of methyl 1-acetyl-4-(4-methoxybenzenesulfonyl)-2,3,4,5-tetrahydro-1H-[1,4]benzodiazepine-3-carboxylate in 14 ml of $CH_2Cl_2$ was added dropwise 143.3 ml (14.3 mmol) of a 1.0 molar solution of $BBr_3$ in $CH_2Cl_2$. The mixture was stirred at room temperature for 1.5 hours. Ice and $H_2O$ were added to the reaction mixture and the insolubles filtered off. The filtrate was diluted with $CH_2Cl_2$ and $H_2O$ and the $CH_2Cl_2$ layer separated, washed with brine and dried ($Na_2$ $SO_4$) The solvent was removed under vacuum to give 1.5 g of a white foam. The solid was chromatographed on silica gel with hexane-ethyl acetate (1:1) as solvent to give a foam which was dried under vacuum to give 0.52 g of product as a white foam; Anal. Calc'd for $C_{19}H_{20}N_2O_6S$: C, 56 4;H, 5.0; N, 6.9; Found: C 55.1; H, 4.7; N, 6.5.

REFERENCE EXAMPLE 199

Methyl 4-(4-Hydroxybenzenesulfonyl)-1-(2-thienylcarbonyl)-2,3,4,5-tetrahydro-1H-[1,4]benzodiazepine-3-carboxylate To a solution of 4.0 g (8.22 mmol) of methyl 4-(4-methoxybenzenesulfonyl)-1-(2-thienylcarbonyl)-2,3,4,5-tetrahydro-1H-[1,4]benzodiazepine-3-carboxylate ml of $CH_2Cl_2$ chilled to 0° C., was added slowly 16.4 ml (16.44 mmol) of 1.0 molar solution of boron tribromide in $CH_2Cl_2$. The mixture was stirred at room temperature overnight and diluted with $CH_2Cl_2$. The mixture was filtered and the solid washed with $CHCl_2$. and $H_2O$. The filtrate was diluted with $H_2O$ and the organic layer separated. The solvent was removed under vacuum and the solid chromatographed on silica gel with hexane-ethyl acetate (1:1) as solvent to give 0.80 g of off white foam; Mass Spectrum (ES) 473.5 (M+H); Anal. Calc'd for $C_{22}H_{20}N_2O_6S_2$: C, 55.9; H, 4.3; N, 5.9. Found: C, 54.5; H, 4.4; N, 5.5.

REFERENCE EXAMPLE 200

Methyl 1-Benzoyl-4-(4-hydroxybenzenesulfonyl)-2,3,4,5-tetrahydro-1H-[1,4]benzodiazepine-3-carboxylate To a solution of 9.8 g (20.39 mmol) of methyl 1-benzoyl-4-(4-methoxybenzenesulfonyl)-2,3,4,5-tetraydro-1H-[1,4]benzodiazepine in 50 ml of $CH_2Cl_2$ cooled to 0°, was added slowly 40.8 ml (40.8 mmol) of a 1.0 molar solution of $BBr_3$ in $CHCl_2$. The mixture was stirred under nitrogen at room temperature overnight. Ice and $H_2O$ were added and the mixture diluted with $C_2Cl_2$. The organic layer was separated and the aqueous layer extracted with ethyl acetate. The combined organic extracts ($CH_2Cl_2$+ethyl acetate) were concentrated under vacuum and the residue dissolved in ethyl acetate. The solution was washed with $H_2O$, brine and dried ($Na_2SO_4$). The solution was filtered through a thin pad of hydrous magnesium silicate and the filtrate concentrated to dryness. The residue was chromatographed on silica gel with hexane-ethyl acetate as solvent to give 8 g of product as an off-white foam;

Mass Spectrum (ES) 467 (M+H); Anal Calc'd for $C_{24}H_{22}N_2O_6S$: C, 61.8; H 4.8; N, 6.0. Found: C, 61.3; H, 4.6; N, 5.8.

Utilizing the method described in Reference Examples 198–200, the following methyl-1-substituted-4-hydroxybenzenesulfonyl)-2,3,4,5-tetrahydro-H-[1,4]benzodiazepine-3-carboxylates can be prepared.

REFERENCE EXAMPLE 201

Methyl 4-(4-Hydroxybenzenesulfonyl)-1-(4-methylphenylsulfonyl)-2,3,4,5-tetrahydro-1H-[1,4]benzodiazepine-3-carboxylate.

REFERENCE EXAMPLE 202

Methyl 1-Methanesulfonyl-4-(4-hydroxybenzenesulfonyl)-2,3,4,5-tetrahydro-1H-[1,4]benzodiazepine-3-carboxylate

REFERENCE EXAMPLE 203

Methyl 4-(4-Hydroxybenzenesulfonyl)-1-(3-pyridinylcarbonyl) 2,3,4,5-tetrahydro-1H-[1,4]benzodiazepine-3-carboxylate

REFERENCE EXAMPLE 204

Methyl 4-(4-Hydroxybenzenesulfonyl)-1-(4-pyridinylcarbonyl-2,3,4,5-tetrahydro-1H-[1,4]benzodiazepine-3-carboxylate

REFERENCE EXAMPLE 205

Methyl 1-(4-Biphenylcarbonl)-4-(4-hydroxybenzenesulfonyl)-2,3,4,5-tetrahydro-1H-[1,4]benzodiazepine-3-carboxylate

REFERENCE EXAMPLE 206

Methyl 4-(4-Hydroxybenzenesulfonyl)-1-(propane1-sulfonyl)-2,3,4,5-tetrahydro-1H-[1,4]benzodiazepine-3-carboxylate

REFERENCE EXAMPLE 207

Methyl 1-([1,1'-Biphenyl]-2-carbonyl)-4-(4-hydroxybenzene-sulfonyl)-2,3,4,5-tetrahydro-1H-[1,4]benzodiazepine-3-carboxylate

REFERENCE EXAMPLE 208

Methyl 1-(3-Fluorobenzoyl)-4-(4-hydroxybenzenesulfonyl)-2,3,4,5-tetrahydro-1H-[1,4]benzodiazepine-3-carboxylate

REFERENCE EXAMPLE 209

Methyl 4-(4-Hydroxybenzenesulfonyl)-1-(2-methyl-5-fluorobenzoyl)-2,3,4,5-tetrahydro-1H-[1,4]benzodiazepine-3-carboxylate

REFERENCE EXAMPLE 210

Methyl 4-(4-Hydroxybenzenesulfonyl)-1-(2-methyl-3-fluorobenzoyl)-2,3,4,5-tetrahydro-1H-[1,4]benzodiazepine-3-carboxylate

REFERENCE EXAMPLE 211

Methyl 4-(4-Hydroxybenzenesulfonyl)-1-(3-phenylpropionyl)-2,3,4,5-tetrahydro-1H-[1,4]benzodiazepine-3-carboxylate

REFERENCE EXAMPLE 212

Methyl 4-(4-Hydroxybenzenesulfonyl)-1-(2-trifluoromethyl-benzoyl)-2,3,4,5-tetrahydro-1H-[1,4]benzodiazepine-3-carboxylate

REFERENCE EXAMPLE 213

Methyl 1-(2-Chloro-6-trifluoromethylbenzoyl)-4-(4-hydroxybenzenesulfonyl)-2,3,4,5-tetrahydro-1H-[1,4]benzodiazepine-3-carboxylate

REFERENCE EXAMPLE 214

Methyl 1-(4-Fluoro-2-trifluoromethylbenzoyl)-4-(4-hydroxybenzenesulfonyl)-2,3,4,5-tetrahydro-1H-[1,4]benzodiazepine-3-carboxylate

REFERENCE EXAMPLE 215

Methyl 1-(2-Fluoro-6-trifluoromethybenzoyl)-4-(4-hydroxybenzenesulfonyl)-2,3,4,5-tetrahydro-1H-[1,4]benzodiazepine-3-carboxylate

REFERENCE EXAMPLE 216

Methyl 4-(4-Hydroxybenzenesulfonyl)-1-(2 methylbenzoyl)-2,3,4,5-tetrahydro-1H-[1,4]benzodiazepine-3-carboxylate

REFERENCE EXAMPLE 217

Methyl 4-(4-Hydroxybenzenesulfonyl)-1-(2-methyl-6-chlorobenzoyl)-2,3,4,5-tetrahydro-1H-[1,4]benzodiazepine-3-carboxylate

REFERENCE EXAMPLE 218

Methyl 1-(2,4-Dimethylbenzoyl)-4-(4-hydroxybenzenesulfonyl)-2,3,4,5-tetrahydro-1H-[1,4]benzodiazepine-3-carboxylate

REFERENCE EXAMPLE 219

Methyl 1-(2,5-Dimethylbenzoyl)-4-(4-hydroxybenzenesulfonyl)-2,3,4,5-tetrahydro-1H-[1,4]benzodiazepine-3-carboxylate

REFERENCE EXAMPLE 220

Methyl 1-(2-Chloro-4-fluorobenzoyl)-4-(4-hydroxybenzenesulfonyl)-2,3,4,5-tetrahydro-1H-[1,4]benzodiazepine-3-carboxylate

REFERENCE EXAMPLE 221

Methyl 1-(2-Chlorobenzoyl)-4-(4-hydroxybenzenesulfonyl)-2,3,4,5-tetrahydro-1H-[1,4]benzodiazepine-3-carboxylate

REFERENCE EXAMPLE 222

Methyl 1-(2-Fluorobenzoyl)-4-(4-hydroxybenzenesulfonyl)-2,3,4,5-tetrahydro-1H-[1,4]benzodiazepine-3-carboxylate

REFERENCE EXAMPLE 223

Methyl 1-(2-Chloro-6-fluorobenzoyl)-4-(4-hydroxybenzene-sulfonyl)-2,3,4,5-tetrahydro-1H-[1,4]benzodiazepine-3-carboxylate

REFERENCE EXAMPLE 224

Methyl 1-(2,3-Difluorobenzoyl)-4-(4-hydroxybenzenesulfonyl)-2,3,4,5-tetrahydro-1H-[1,4]benzodiazepine-3-carboxylate

REFERENCE EXAMPLE 225

Methyl 1-(2,4-Dichlorobenzoyl)-4-(4-hydroxybenzenesulfonyl)-2,3,4,5-tetrahydro-1H-[1,4]benzodiazepine-3-carboxylate

REFERENCE EXAMPLE 226

Methyl 1-(2,3-Dichlorobenzoyl)-4-(4-hydroxybenzenesulfonyl)-2,3,4,5-tetrahydro-1H-[1,4]benzodiazepine-3-carboxylate

REFERENCE EXAMPLE 227

Methyl-1-(2,5-Dichlorobenzoyl)-4-(4-hydroxybenzenesulfonyl)-2,3,4,5-tetrahydro-1H-[1,4]benzodiazepine-3-carboxylate

REFERENCE EXAMPLE 228

Methyl 4-(4-Hydroxybenzenesulfonyl)-1-(2-methylthiobenzoyl)-2,3,4,5-tetrahydro-1H-[1,4]benzodiazepine-3-carboxylate

REFERENCE EXAMPLE 229

Methyl 4-(4-Hydroxybenzenesulfonyl)-1-(3-methyl-2-thienylcarbonyl)-2,3,4,5-tetrahydro-1H-[1,4]benzodiazepine-3-carboxylate

REFERENCE EXAMPLE 230

Methyl 4-(4-Hydroxybenzenesulfonyl)-1-(4-methyl-2-thienylcarbonyl)-2,3,4,5-tetrahydro-1H-[1,4]benzodiazepine-3-carboxylate

REFERENCE EXAMPLE 231

Methyl 1-(3-Chloro-2-thienylcarbonyl)-4-(hydroxybenzenesulfonyl)-2,3,4,5-tetrahydro-1H-[1,4]benzodiazepine-3-carboxylate

REFERENCE EXAMPLE 232

Methyl 1-(2-Furanylcarbonyl)-4-(4-hydroxybenzenesulfonyl)-2,3,4,5-tetrahydro-1H-[1,4]benzodiazepine-3-carboxylate

REFERENCE EXAMPLE 233

Methyl 4-(4-Hydroxybenzenesulfonyl)-1-(3-methyl-2-furanylcarbonyl)-2,3,4,5-tetrahydro-1H-[-1,4]benzodiazepine-3-carboxylate

REFERENCE EXAMPLE 234

Methyl 4-(4-Hydroxybenzenesulfonyl)-1-(4-methyl-2-furanylcarbonyl)-2,3,4,5-tetrahydro-1H-[1,4]benzodiazepine-3-carboxylate

REFERENCE EXAMPLE 235

Methyl 1-(5-Chloro-2-furanylcarbonyl)-4-(4-hydroxybenzenesulfonyl)-2,3,4,5-tetrahydro-1H-[1,4]benzodiazepine-3-carboxylate

REFERENCE EXAMPLE 236

Methyl 1-(5-Chloro-2-thienylcarbonyl)-4-(4-hydroxybenzenesulfonyl)-2,3,4,5-tetrahydro-1H-[1,4]benzodeiazepine-3-carboxylate

REFERENCE EXAMPLE 237

Methyl 1-Propionyl-4-(4-hydroxybenzenesulfonyl)-2,3,4,5-tetrahydro-1H-[1,4]benzodeiazepine-3-carboxylate

REFERENCE EXAMPLE 238

Methyl 1-Hexanoyl-4-(4-hydroxybenzenesulfonyl)-2,3,4,5-tetrahydro-1H-[1,4]benzodiazepine-3-carboxylate

REFERENCE EXAMPLE 239

Methyl 4-(4-Hydroxybenzenesulfonyl)-1-(3-thienylcarbonyl)-2,3,4,5-tetrahydro-1H-[1,4]benzodiazepine-3-carboxylate

REFERENCE EXAMPLE 240

Methyl 1-(3-Furanylcarbonyl)-4-(4-hydroxybenzenesulfonyl)-2,3,4,5-tetrahydro-1H-[1,4]benzodiazepine-3-carboxylate

REFERENCE EXAMPLE 241

Methyl 1-(Acetylaminoacetyl)-4-(4-hydroxybenzenesulfonyl)-2,3,4,5-tetrahydro-1H-[1,4]benzodiazepine-3-carboxylate

REFERENCE EXAMPLE 242

Methyl 1-(N,N Dimethylaninoacetyl)-4-(4-hydroxybenzenesulfonyl)-2,3,4,5-tetrahydro-1H-[1,4]benzodiazepine-3-carboxylate

REFERENCE EXAMPLE 243

Methyl 1-(Cyclopropylcarbonyl)-4-(4-hydroxybenzenesulfonyl)-2,3,4,5-tetrahydro-1H-[1,4]benzodiazepine

REFERENCE EXAMPLE 244

Methyl 4-(4-Hydroxybenzenesulfonyl)-1-(trifluoroacetyl) -2,3,4,5-tetrahydro-1H-[1,4]benzodiazepine

REFERENCE EXAMPLE 245

Methyl 1-Acetyl-4-(4-but-2-ynyloxybenzenesulfonyl)-2,3,4,5-tetrahydro-1H-[1,4]benzenediazepine-3-carboxylate To a stirred solution of 3.73 g (14.22 mmol) of triphenylphosphine in 80 ml of toluene-tetrahydrofuran (3:1) was added 1.06 ml (14.22 mmol) of 2-butyn1-ol and 5.0 g (12.36 mmol) of methyl 1-acetyl-4-(4-hydroxybenzenesulfonyl)-2,3,4,5-tetrahydro-1H-[1,4]benzodiazepine-3-carboxylate. To this solution under nitrogen was added slowly dropwise 2.24 ml (14.22 mmol) of diethyl azodicarboxylate. The mixture was stirred at room temperature overnight and concentrated to dryness under vacuum. To the residue was added ethyl acetate and $H_2O$ and the solid filtered off. The filtrate was concentrated under vacuum and extracted with $CH_2C_2$. The extract was washed with brine, dried (Na2SO$_4$) and concentrated to dryness under vacuum. The residue was triturated with ethyl acetate-hexane to give 6.5 of solid. This solid was chromatographed on silica gel with ethyl acetate-hexane (1:1) as solvent to give 3.9 g of white solid; Mass Spectrum (ES) 4.57.5 (M+H); Anal. Calc'd for $C_{23}H_{24}N_2O_6S$: C, 60.5; H, 5.3; N, 6.1. Found: C, 60.2; H, 5.2; N, 6.2.

REFERENCE EXAMPLE 246

Methyl 1-Benzoyl-4-(4-but-2-ynyloxybenzenesulfonyl)-2,3,4,5-tetrahydro-1H-[1,4]benzodiazepine-3-carboxylate To a stirred solution of 1.26 g (4.82 mmol) of triphenylphosphine in 15 ml of toluene-tetrahydrofuran (4:1) under nitrogen was added 360 uL (4.82 mmol) of 2-butyn-1-ol and 1.5 g of (3.22 mmol)of methyl 1-benzoyl-4-(4-hydroxybenzene-sulfonyl)-2,3,4,5-tetrahydro-1H-[1,4]benzodiazepine-3-carboxylate. To the stirred mixture was added slowly 759 uL of diethyl azodicarboxylate and the reddish clear solution stirred overnight at room temperature. The solvent was removed under vacuum and $CH_2Cl_2$ added. The $CH_2Cl_2$ was washed with $H_2O$ and brine, dried ($Na_2SO_4$) and the solvent removed. The residue was chromatographed on silica gel with hexane-ethyl acetate (1:1) to give 1.65 g of white solid; Mass Spectrum (ES) 519 (M+H); Anal Calc'd for $C_{28}H_{26}N_2O_6S$: C, 64.9; H, 5:1; N, 5.4. Found: C, 60.5; H, 5.2; N, 6.9.

REFERENCE EXAMPLE 247

Methyl 4-(4-But-2-ynylbenzenesulfonyl)-1-(2-thienylcarbonyl)-2,3,4,5-tetrahydro-1H-[1,4]benzodiazepine-3-carboxylate To a stirred mixture of 0.475 g (1.81 mmol) of triphenylphosphine, 134.8 uL (1.84 mmol) of 2-butyn-1-ol and 0.74 g of methyl 4-(4-hydroxysbenzenesulfonyl)-1-(2-thienylcarbonyl)-2,3,4,5-tetrahydro-1H-[1,4]benzodiazepine-3-carboxylate in 7 ml of toluene and 2 ml of tetrahydrofuran was added slowly 285 uL (1.81 mmol) of diethyl azodicarboxylate. The mixture was stirred overnight at room temperature and to the mixture was added 0.475 g of triphenylphosphine, 125 uL of 2-butyn-1-ol and 0.285 of diethyl azodicarboxylate. The mixture was stirred for 2.5 hrs. at room temperature and the solvent removed. To the residue was added $CH_2Cl_2$ and the mixture washed with $H_2O$ and brine. The $CH_2Cl_2$ layer was dried ($NaSO_4$) and the solvent removed to give 2.0 g of a yellow oil. Chromatography on silica gel with hexane-ethyl acetate (1.1) gave 1.0 g of off-white foam; Mass Spectrum (ES) 525.6 (M+H); Anal. Calc'd for $C_{26}H_{24}N_2O_6S_2$: C, 59.5; H, 4.6; N, 5.3. Found: C, 56.1;H, 4.9; N, 7.3)

Utilizing the method described in Reference Examples 245–247, the following methyl 1-substituted-4-(4-but-2-ynyloxybenzenesulfonyl)-2,3,4,5-tetrahydro-1H-[1,4]benzodiazepine-3-carboxylate and methyl 1-substituted-4-(4-[4-substituted-but-2-ynyloxy]benzenesulfonyl)-2,3,4,5-tetrahydro-1H-[1 ,4]benzodiazepine-3-carboxylates can be prepared.

REFERENCE EXAMPLE 248

Methyl 1-Butoxyacetyl-4-(4-but-2-ynyloxybenzenesulfonyl)-2,3,4,5-tetrahydro-1H-[1,4]benzodiazepine-3-carboxylate

REFERENCE EXAMPLE 249

Methyl 4-(4-But-2-ynyloxybenzenesulfonyl)-1-(4-methylphenylsulfonyl)-2,3,4,5-tetrahydro-1H-[1,4]benzodiazepine-3-carboxylate

REFERENCE EXAMPLE 250

Methyl 1-Methansulfonyl-4-(4-but-2-ynyloxybenzenesulfonyl)-2,3,4,5-tetrahydro-1H-[1,4]benzodiazepine-3-carboxylate

REFERENCE EXAMPLE 251

Methyl 1-Benzoyl-4-(4-[4-methoxybut-2-ynyloxy]
benzenesulfonyl)-2,3,4,5-tetrahydro-1H-[1,4]
benzodiazepine-3-carboxylate

REFERENCE EXAMPLE 252

Methyl 1-Acetyl-4-(4-[4-methoxybut-2-ynyloxy]
benzenesulfonyl)-2,3,4,5-tetrahydro-1H-[1,4]
benzodiazepine-3-carboxylate

REFERENCE EXAMPLE 253

Methyl 4-[4-But-2-ynyloxy]benzenesulfonyl)-1-(3-
pyridinylcarbonyl)-2,3,4,5-tetrahydro-1H-[1,4]
benzodiazepine-3-carboxylate

REFERENCE EXAMPLE 254

Methyl 4-(4-Pent-2-ynyloxybenzenesulfonyl)-1-(3-
pyridinylcarbonyl)-2,3,4,5-tetrahydro-1H-[1,4]
benzodiazepine-3-carboxylate

REFERENCE EXAMPLE 255

Methyl 4-(4-[4-Methoxybut-2-ynyloxy]
benzenesulfonyl)-1-(2-thienylcarbonyl)-2,3,4,5-
tetrahydro-1H-[1,4]benzodiazepine-3-carboxylate

REFERENCE EXAMPLE 256

Methyl 4-(4-But-2-ynyloxybenzenesulfonyl)-1-(4-
pyridinylcarbonyl)-2,3,4,5-tetrahydro-1H-[1,4]
benzodiazepine-3-carboxylate

REFERENCE EXAMPLE 257

Methyl 1-(4-Biphenylcarbonyl)-4-(4-but-2-
ynyloxybenzenesulfonyl)-2,3,4,5-tetrahydro-1H-[1,
4]benzodiazepine-3-carboxylate

REFERENCE EXAMPLE 258

Methyl 4-(4-[4-Methoxybut-2-ynyloxy]
benzenesulfonyl)-1-(propane1-sulfonyl)-2,3,4,5-
tetrahydro-1H-[1,4]benzodiazepine-3-carboxylate

REFERENCE EXAMPLE 259

Methyl 1-([1,1'-Biphenyl]-2-carbonyl)-4-(4-[4-
methoxybut-2-ynyloxy]benzenesulfonyl)-2,3,4,5-
tetrahydro-1H-[1,4]benzodiazepine-3-carboxylate

REFERENCE EXAMPLE 260

Methyl 1-(3-Fluorobenzoyl)-4-(4-pent-2-
ynyloxybenzenesulfonyl)-2,3,4,5-tetrahydro-1H-[1,
4]benzodiazepine-3-carboxylate

REFERENCE EXAMPLE 261

Methyl 4(4-[4-Ethoxybut-2-ynyloxy]
benzenesulfonyl)-1-(2 methyl-3-fluorobenzoyl) -2,3,
4,5-tetrahydro-1H-[1,4]benzodiazepine-3-
carboxylate

REFERENCE EXAMPLE 262

Methyl 4-(4-[4-Dimethylaminobut-2-ynyloxy]
benzenesulfonyl)-1-(2 methyl-3-fluorobenzoyl)-2,3,
4,5-tetrahydro-1H-[1,4]benzodiazepine-3-
carboxylate

REFERENCE EXAMPLE 263

Methyl 4-(4-But-2-ynyloxybenzenesuflony)-1-(2-
triflouromethylbenzoyl)-2,3,4,5-tetrahydro-1H-[1,4]
benzodiazepine-3-carboxylate

REFERENCE EXAMPLE 264

Methyl 1-(2-Chloro-6-trifluormethylbenzoyl)-4-(4-
pent-2-ynyloxybenzenesulfonyl)-2,3,4,5-tetrahydro-
1H-[1,4]benzodiazepine-3-carboxylate

REFERENCE EXAMPLE 265

Methyl 1-(4-Fluoro-2-trifluoromethylbenzoyl)-4-(4-
[4-methoxybut-2-ynyloxy]benzenesulfonyl)-2,3,4,5-
tetrahydro-1H-[1,4]benzodiazepine-3-carboxylate

REFERENCE EXAMPLE 266

Methyl 1-(2-Fluoro-6-trifluormethylbenzoyl)-4-(4-
pent-2-ynyloxybenzenesulfonyl)-2,3,4,5-tetrahydro-
1H-[1,4]benzodiazepine-3-carboxylate

REFERENCE EXAMPLE 267

Methyl 4-(4-But -2-ynyloxybenzenesulfonyl)-1-(2
methyl-6-chlorobenzoyl)-2,3,4,5-tetrahydro-1H-[1,4]
benzodiazepine-3-carboxylate

REFERENCE EXAMPLE 268

Methyl 1-(2,4-Dimethylbenzoyl)-4-(4-[4-
methoxybut-2-ynyloxy]benzenesulfonyl)-2,3,4,5-
tetrahydro-1H-[1,4]benzodiazepine-3-carboxylate

REFERENCE EXAMPLE 269

Methyl 1-(2,5-Dimethylbenzoyl)-4-(4-[4-
methoxybut-2-ynyloxy]benzenesulfonyl)-2,3,4,5-
tetrahydro-1H-[1,4]benzodiazepine-3-carboxylate

REFERENCE EXAMPLE 270

Methyl 1-(2-Chloro-4-flurobenzoyl)-4-(4-[4-
methoxybut-2-ynyloxy]benzenesulfonyl)-2,3,4,5-
tetrahydro-1H-[1,4]benzodiazepine-3-carboxylate

REFERENCE EXAMPLE 271

Methyl 1-(2-Chlorobenzoyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 272

Methyl 1-(2-Chlorobenzoyl)-4-(4-pent-2-ynyloxybenzenesulfonyl)-2,3,4,5-tetrahydro-1H-[1,4]benzodiazepine-3-carboxylate

REFERENCE EXAMPLE 273

Methyl 1-(2-Fluorobenzoyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 274

Methyl 1-(2-Chloro-6-fluorobenzoyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 275

Methyl 1-(2,3-Difluorobenzoyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 276

Methyl 1-(2,4-Dichlorobenzoyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 277

Methyl 1-(2,4-Dichlorobenzoyl)-4-(4-pent-2-ynyloxybenzenesulfonyl)-2,3,4,5-tetrahydro-1H-[1,4]benzodiazepine-3-carboxylate

REFERENCE EXAMPLE 278

Methyl 1-(2,3-Dichlorobenzoyl)-4(4-[4-methoxybut-2-ynxloxy]benzenesulfonyl)-2,3,4,5-tetrahydro-1H-[1,4]benzodiazepine-3-carboxylate

REFERENCE EXAMPLE 279

Methyl 1-(2,5-Dichlorobenzoyl)-4-(4-[4-hydroxybut-2-ynyloxy]benzenesulfonyl)-2,3,4,5-tetrahydro-1H-[1,4]benzodiazepine-3-carboxylate

REFERENCE EXAMPLE 280

Methyl 1-(Benzoyl)-4-(4-pent-2-ynyloxybenzenesulfonyl)-2,3,4,5-tetrahydro-1H-[1,4]benzodiazepine-3-carboxylate

REFERENCE EXAMPLE 281

Methyl 4-(4-But-2-ynyloxybenzenesulfony)-1-(2-methylthiobenzoyl)-2,3,4,5-tetrahydro-1H-[1,4]benzodiazepine-3-carboxylate

REFERENCE EXAMPLE 282

Methyl 4-(4-But-2-ynyloxybenzenesulfony)-1-(3-methyl-2-thienylcarbonyl)-2,3,4,5-tetrahydro-1H-[1,4]benzodiazepine-3-carboxylate

REFERENCE EXAMPLE 283

Methyl 4-(4-[4-Hydroxybut -2-ynyloxy]benzenesulfonyl)-1-(4 methyl-2-thienylcarbonyl)-2,3,4,5-tetrahydro-1H-[1,4]benzodiazepine-3-carboxylate

REFERENCE EXAMPLE 284

Methyl 1-(3-Chloro-2-thienylcarbonyl)-4-(4-[4-dimethylaininobut 2-ynyloxy]benzenesulfonyl)-2,3,4,5-tetrahydro-1H-[1,4]benzodiazepine-3-carboxylate

REFERENCE EXAMPLE 285

Methyl 1-(2-Furanylcarbonyl)-4-(4-[4-methylamlnobut-2-ynyloxy]benzenesulfonyl)-2,3,4,5-tetrahydro-1H-[1,4]benzodiazepine-3-carboxylate

REFERENCE EXAMPLE 286

Methyl 4-(4-But-2-ynyloxybenzenesulfonyl)-1-(3-methyl-2-furanylcarbonyl)-2,3,4,5-tetrahydro-1H-[1,4]benzodiazepine-3-carboxylate

REFERENCE EXAMPLE 287

Methyl 4-(4-[4-But-2-ynyloxybenzenesulfonyl)-1-(-4-methyl-2-furanylcarbonyl)-2,3,4,5-tetrahydro-1H-[1,4]benzodiazepine-3-carboxylate

REFERENCE EXAMPLE 288

Methyl 1-(5-Chloro-2-furanylcarbonyl)-4(4-[4-ethoxybut-2-ynyloxy]benzenesulfonyl)-2,3,4,5-tetrahydro-1H-[1,4]benzodiazepine-3-carboxylate

REFERENCE EXAMPLE 289

Methyl 1-(5-Chloro-2-thienylcarbonyl)-4-(4-[4-hydroxybut-2-ynyloxy]benzenesulfonyl)-2,3,4,5-tetrahydro-1H-[1,4]benzodiazepine-3-carboxylate

REFERENCE EXAMPLE 290

Methyl 1-Propionyl-4-(4-[4-hydroxybut-2-ynyloxy]benzenesulfonyl)-2,3,4,5-tetrahydro-1H-[1,4]benzodiazepine-3-carboxylate

REFERENCE EXAMPLE 291

Methyl 1-Hexanoyl-4-(4-[4-methoxybut-2-ynyloxy]benzenesulfonyl)-2,3,4,5-tetrahydro-1H-[1,4]benzodiazepine-3-carboxylate

REFERENCE EXAMPLE 292

Methyl 4-(4-But-2-ynyloxybenzenesulfonyl)-1-(propionyl)-2,3,4,5-tetrahydro-1H-[1,4]benzodiazepine-3-carboxylate

REFERENCE EXAMPLE 293

Methyl 4-(4-But-2-ynyloxybenzenesulfonyl)-1-(3-thienylcarbonyl)-2,3,4,5-tetrahydro-1H-[1,4]benzodiazepine-3-carboxylate

REFERENCE EXAMPLE 294

Methyl 4-(4-But-2-ynyloxybenzenesulfonyl)-1-(3-furanycarbonyl)-2,3,4,5-tetrahydro-1H-[1,4]benzodiazepine-3-carboxylate

REFERENCE EXAMPLE 295

Methyl 1-(Ethoxyacetyl)-4-(4-[4-methoxybut-2-ynyloxy]benzenesulfonyl)-2,3,4,5-tetrahydro-1H-[1,4]benzodiazepine-3-carboxylate

REFERENCE EXAMPLE 296

Methyl 1-(Acetylaminoacetyl)-4-(4-but-2-ynyloxybenzenesulfonyl)-2,3,4,5-tetrahydro-1H-[1,4]benzodiazepine-3-carboxylate

REFERENCE EXAMPLE 297

Methyl 1-(N,N-Dimethylaminoacety)-4-(4-[4-methoxybut-2-ynyloxy]benzenesulfonyl)-2,3,4,5-tetrahydro-1H-[1,4]benzodiazepine-3-carboxylate

REFERENCE EXAMPLE 298

Methyl 1-(Cyclopropylcarbonyl)-4-(4-[4-methxybut-2-ynyloxy]benzenesulfonyl)-2,3,4,5-tetrahydro-1H-[1,4]benzodiazepine-3-carboxylate

REFERENCE EXAMPLE 299

Methyl 1-(Cyclobutylcarbonyl)-4-(4-but-2-ynyloxybenzeneulfonyl)-2,3,4,5-tetrahydro-1H-[1,4]benzodiazepine-3-carboxylate

REFERENCE EXAMPLE 300

Methyl 4-(4-But-2-ynyloxybenzenesulfonyl)-1-(triflouroacety)-2,3,4,5-tetrahydro-1H-[1,4]benzodiazepine-3-carboxylate

REFERENCE EXAMPLE 301

Sodium 4-But-2-ynyloxybenzenesulfonate

To a solution of 52.35 g (0.225 mol) of 4-hydroxybenzenesulfonate sodium salt in 1L of isopropanol and 225 mL of a 1.0N solution of sodium hydroxide was added 59.96 g (0.45 mol) of 1-bromo-2-butyne. The resulting mixture was heated to 70° for 15 h and then the isopropanol was removed by evaporation in vacuo. The resulting white precipitate was collected by filtration, washed with isopropanol and ether and dried under vacuum to give 56.0 g (100%) of 4-but-2-ynyloxybenzenesulfonic acid sodium salt as a white solid.

REFERENCE EXAMPLE 302

4-But-2-ynyloxybenzenesulfonyl chloride

To a 0° solution of 43.8 mL (0.087 mol) of oxalyl chloride in 29 mL of dichloromethane was dropwise added 6.77 mL (0.087 mol) of DMF followed by 7.24 g (0.029 mol) of 4-but-2-ynyloxybenzenesulfonic acid sodium salt. The reaction mixture was stirred for 10 minutes at 0° then let warm to room temperature and stirred for 2 days. The reaction was then poured into ice and extracted with 150 mL of hexanes. The organics were washed with water and brine, dried over $Na_2SO_4$, filtered and concentrated in vacuo to provide 6.23 g (88%) of the sulfonyl chloride as a yellow solid; m.p. 63–65° C.; Mass Spec (EI) 243.9 ($M^+$).

REFERENCE EXAMPLE 303

But-2-ynyloxybenzene

To a solution of 6.14 g (0.023 mol) of triphenylphosphine dissolved in 100 mL of benzene and 40 mL of THF was added 1.64 g (0.023 mol) of 2-butyn-1-ol. After five minutes 2.00 g (0.021 mol) of phenol, dissolved in 10 mL of THF, was added to the reaction followed by 3.69 mL (0.023 mol) of diethyl azodicarboxylate. The resulting reaction mixture was stirred for 18 h at room temperature and then concentrated in vacuo. The residue was chromatographed on silica gel eluting with ethyl acetate/hexanes (1:10) to provide 2.18 g (70%) of the desired butynyl ether as a clear liquid;Mass Spec (Electrospray) 146.0 (MH+)

REFERENCE EXAMPLE 304

4-But-2-ynyloxybenzenesulfonyl chloride

To a solution of 0.146 g (1.0 mmol) of but-2-ynyloxybenzene in 0.3 mL of dichloromethane in an acetone/ice bath under $N_2$ was dropwise added a solution of 0.073 mL (1.1 mmol) of chlorosulfonic acid in 0.3 mL of dichloromethane. After the addition was complete, the ice bath was removed and the reaction was stirred at room temperature for 2 h. To the reaction was then dropwise added 0.113 mL (1.3 mmol) of oxalyl chloride, followed by 0.015 mL DMF. The reaction was heated to reflux for 2 h and then diluted with hexane and poured into ice water. The organic layer was washed with brine, dried over sodium sulfate, and concentrated in vacuo to provide 0.130 mg (53%) of the desired product as a light brown solid.

The present invention may be embodied in other specific forms without departing from the spirit or essential attributes thereof and, accordingly, reference should be made to the appended claims, rather than to the foregoing specification, as indicating the scope of the invention.

EXAMPLE 1

1-Acetyl-4-(4-but-2-ynyloxbenzenesulfonyl)-2,3,4, 5-tetrahydro-1H-[1,4]benzodiazepine-3-carboxylic acid, hydroxyamide To a mixture of 6.0 g(13.14 mmol) of methyl 1-acetyl-4-(4-but-2-ynyloxybenzene- sulfonyl)-2,3,4,5-tetrahydo-1H-[1,4]benzodiazepine-3-carboxylate in 66 ml of tetrahydrofuran was added 17.1 (17.1 mmol) of 1N KOH. The mixture was stored at room temperature for 3 hours and concentrated to dryness. Toluene was added several times and the solvent removed under vacuum after each addition. The residue was dried under vacuum at 75° C. for 2 days to give 6.5 g of the potassium salt of 1-acetyl-4-(4-but-2-ynyloxybenzenesulfonyl)-2,3,4,5-tetrahydro-1H-[1,4]benzo-diazepine-3-carboxylic acid; Anal. Cal'd for $C_{22}H_{12}N_6O_6SK$: C, 55.0; H, 4; N, 5.8. Found C, 52.0; H, 4.5; N, 5.6.

The preceding potassium salt was converted to the 3-carboxylic acid, hydroxyamide in the following manner: To a stirred and chilled (0°)solution of 26.1 ml (52.36 mmol) of oxalyl (2.0M solution in $CH_2Cl_2$) in 80 ml of $CH2Cl_2$) was added slowly 4.05 ml (52.36 mmol) of N,N-dimethylformamide. To this viscous mixture was added a solution of the preceding 3-carboxylic acid potassium salt in 30 ml of N,N-dimethylformamide and the mixture was stirred at room temperature for 1.5 hr and chilled (0°) (solution A). A solution of 11.89 ml (0.194 ml) of hydroxylamine (50% in $H_2O$) in 60 ml of tetrahydrofuran was cooled in an ice bath (solution B). To the cold solution B was added slowly the solution A and the mixture allowed to warm to room temperature and was stirred overnight. The mixture was diluted with 200 ml of $CH_2Cl_2$ and washed with 100 ml of $H_2O$. The organic layer was separated and the aqueous layer was extracted with $CH_2Cl_2$. The organic layer and extract were combined, and the solvent removed under vacuum. The residue was diluted with 300 ml of ethyl acetate and the solution washed with 20 ml each of $H_2O$, 2N citric acid, $H_2O$ and with 120 ml of $NaHCO_3$ (2 times) and 120 ml of brine. The solution was dried ($Na_2SO_4$) and the solvent removed under vacuum to give a foam. Crystallization from ethyl acetate gave 2.5 g of white crystals, mp 167–169° C.; Anal Calc'd for $C_2H_{23}N_3O_6S$: C, 57.8; H, 5.1; N, 9.2. Found: C, 57.5; H, 5.2; N, 8.9.

EXAMPLE 2

4-(4-But-2-ynyloxybenzenesulfonyl)-1-(2-thienylcarbonyl)-2,3,4,5-tetrahydro-1H-[1,4]benzodiazepine-3-carboxylic acid, hydroxyamide To a mixture of 0.87 g (1.66 mmol) of methyl 4-(4-but-2-ynyloxybenzenesulfonyl)-2,3,4,5-tetrahydro-1H-[1,4]benzodiazepine-3-carboxylate in 4 ml or tetrahydrofuran was added 2.2ml (2.2 mmol) of 1N KOH. The solution was stirred at room temperature for 2.5 hrs. and then concentrated to dryness. Toluene was added repeatedly and the solvent removed after each addition. The residue was dried at 75° C. for 60 hrs to give 0.99 of a foam; Anal Calc'd for $C_{25}H_{22}N_2O_6S_2K$: C, 54.7; H, 3.9; N, 5.1. Found: C, 47.8; H, 4.4; N, 6.0.

To a chilled (0°) solution of 2.66 ml(5.3 mmol) of oxalyl chloride (2.0M solution in $CH_2Cl_2$) in 8 ml of $CH_2Cl_2$ was added slowly 412 µL of N,N-dimethylformamide. To this solution was added a solution of 0.73 g (1.33 mmol) of the preceding potassium salt in 3 ml of N,N-dimethylformamide (solution A). A solution of 1.22 ml (19.95 mmol) of hydroxylamine (50% in $H_2O$) in 6 ml of tetrahydrofuran was chilled to 0° (solution B). The cooled solution A was added slowly to the cooled solution B and the mixture allowed to warm to room temperature and stir overnight. The mixture was diluted with $CH_2Cl_2$ and $H_2O$ and the organic layer separated. The aqueous layer was extracted with $CH_2Cl_2$ and the organic layer and extract combined and concentrated to dryness. The residue was diluted with ethyl acetate and the solution washed with 2N citric acid, $H_2O$, 1N $NaHCO_3$, brine and dried ($Na_2SO_4$). The solvent was removed to give 0.65 g of solid. The solid was chromatographed on silica gel with hexane-ethyl acetate (1:1) and then 10% $CH_3OH$ in ethyl acetate to give 0.20 g of a white foam; Mass spectrum (ES) 526.4(M+H); Anal Calc'd for $C_{25}H_{23}N_3O_2S_2$: C, 57.1; H, 4.4; N, 8.0. Found: C, 56.9; H, 4.3; N, 7.8.

EXAMPLE 3

1-Benzoyl-4-(4-but-2-ynyloxybenzenesulfonyl)-2,3, 4,5-tetrahydro-1H-[1,4]-benzodiazepine-3-carboxylic acid, hydroxyamide To a mixture of 1.5 g (2.89 mmol) of methyl 1-benzoyl-4-(4-but-2-ynyloxybenzenesulfonyl)-2,3,4,5-tetrahydro-1H-[1,4]benzodiazepine-3-carboxylate in 7 ml of tetrahydrofuran was added 3.8 ml (3.8 mmol) of 1NKOH. The solution was stirred for 2 hours and the mixture concentrated to dryness. Toluene was added repeatedly and the solvent removed after each addition to give a solid. The solid was dried at 75° C. under vacuum to give 1.6 g of the potassium salt of 1-benzoyl-4-(4-but-2-ynylbenzenesulfonyl)-2,3,4,5-tetrahydro-1H-[1,4]benzodiazepine-3-carboxylic acid as a white foam; Mass spectrum (ES) 505.2 (M+H): Anal Calc'd for $C_{27}H_{24}N_2O_6SK$; C, 61.9; H, 4.5; N, 5.4. Found: C, 5.22; H, 4.6; N, 5.9. The preceding potassium salt was converted to the 3-carboxylic acid, hydroxamide in the following manner. To a stirred and chilled (0° ) solution of 4.8 ml (9.6 mmol) of oxalyl chloride (2.0M solution in $CH_2Cl_2$) in 14 ml of $CH_2Cl_2$ was added slowly 370 µL of N,N-dimethylformamide. To this mixture was added a chilled solution of the preceding 3-carboxylic acid potassium salt in 5 ml of N,N dimethylformamide. The mixture was stirred at 0° for 1.5 hours (solution A). A solution of 2.2 ml (35.9 mmol) of hydroxylamine (50% in $H_2O$) in 10 ml of tetrahydrofuran was cooled in an ice bath (0°) (solution B). To the stirred cold solution B was added slowly the cold solution A. The mixture was allowed to warm to room temperature and stir overnight. The mixture was diluted with $CH_2Cl_2$ and $H_2O$ and the organic layer separated. The organic layer was concentrated and the residue diluted with ethyl acetatee and washed with 1M $NaHCO_3$, $H_2O$, brine and dried ($Na_2SO_4$). The solvent was removed to give 2.0 g of a solid. Chromatography on silica gel with 10% $CH_3OH$ in ethyl acetate gave 0.96 g of solid. The solid was dissolved in hexane-ethyl acetate (1:1) and the solution filtered through diatomaceous earth and then through silica gel (500 ml wash). The product was then eluted from the silica gel with 10% $CH_3OH$ in ethyl acetate to give a 0.593 g of white solid; Mass spectrum (ES) 520 (M+H). Anal. Calc'd for $C_{27}H_{25}N_3O_6S$: C, 62.4; H, 4.9; N, 8.1. Found: C, 61.2; H, 4.9; N, 7.9.

Utilizing the method described in Examples 1–3, the following 1-substituted-4-(4-but-2-ynyloxybenzenesulfonyl)-2,3,4,5-tetrahydro-1H-[1,4]benzodiazepine-3-carboxylic acid, hydroxyamides and 1-substituted-4-(4-[4-substituted-but-2-ynyloxy]benzenesulfonyl)-2,3,4,5-tetrahydro-1H-[1,4]benzodiazepine-3-carboxylic acid, hydroxyamides can be prepared.

EXAMPLE 4

1-Butoxyacetyl-4-(4-but-2-ynyloxybenzenesulfonyl)-2,3,4,5-tetrahydro-1H-[1,4]benzodiazepine-3-carboxylic acid, hydroxyamide

EXAMPLE 5

4-(4-But-2-ynyloxybenzenesulfonyl)-1-(4-methylphenylsulfonyl)-2,3,4,5-tetrahydro-1H-[1,4]benzodiazepine-3-carboxylic acid, hydroxyamide

EXAMPLE 6

4-(4-But-2-ynyloxybenzenesulfonyl)-1-methansulfonyl-2,3,4,5-tetrahydro-1H-[1,4]benzodiazepine-3-carboxylic acid, hydroxyamide

EXAMPLE 7

1-Benzoyl-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 8

1-Acetyl-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 9

4-[4-But-2-ynyloxy]benzenesulfonyl)-1-(3-pyridinylearbonyl)-2,3,4,5-tetrahydro-1H-[1,4]benzodiazepine-3-carboxylic acid, hydroxyamide

EXAMPLE 10

4-(4-Pent-2-ynyloxy benzenesulfonyl)-1-(3-pyridinylcarbonyl)-2,3,4,5-tetrahydro-1H-[1,4]benzodiazepine-3-carboxylic acid, hydroxyamide

EXAMPLE 11

4-(4-[4-Methoxybut-2-ynyloxy]benzenesulfonyl)-1-(2-thienylcarbonyl)-2,3,4,5-tetrahydro-1H-[1,4]benzodiazepine-3-carboxylic acid, hydroxyamide

EXAMPLE 12

4-(4-But-2-ynyloxybenzenesulfonyl)-1-(4-pyridinylcarbonyl)-2,3,4,5-tetrahydro-1H-[1,4]benzodiazepine-3-carboxylic acid, hydroxyamide

EXAMPLE 13

1-(4-Biphenylcarbonyl)-4-(4-but-2-ynyloxybenzenesulfonyl)-2,3,4,5-tetrahydro-1H-[1,4]benzodiazepine-3-carboxylic acid, hydroxyamide

EXAMPLE 14

4-(4-[4-Methoxybut-2-ynyloxy]benzenesulfonyl)-1-(propane-1-sulfonyl)-2,3,4,5-tetrahydro-1H-[1,4]benzodiazepine-3-carboxylic acid, hydroxyamide

EXAMPLE 15

1-([1,1'-Bipheny]-2-carbonyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 16

1-(3-Fluorobenzoyl)-4-(4-pent-2-ynyloxybenzenesulfonyl)-2,3,4,5-tetrahydro-1H-[1,4]benzodiazepine-3-carboxylic acid, hydroxyamide

EXAMPLE 17

4-(4-[4-Ethoxybut-2-ynyloxy]benzenesulfonyl)-1-(2 methyl-3-fluorobenzoyl)-2,3,4,5-tetrahydro-1H-[1,4]benzodiazepine-3-carboxylic acid, hydroxyamide

EXAMPLE 18

4-(4-[4-Dimethylaminobut-2-ynyloxy]benzenesulfonyl)-1-(2 methyl-3-fluorobenzoyl)-2,3,4,5-tetrahydro-1H-[1,4]benzodiazepine-3-carboxylic acid, hydroxyamide

EXAMPLE 19

4-(4-But-2-ynyloxybenzenesuflony)-1-(2-triflouromethylbenzoyl)-2,3,4,5-tetrahydro-1H-[1,4]benzodiazepine-3-carboxylic acid, hydroxyamide

EXAMPLE 20

1-(2-Chloro-6-triflourmethylbenzoyl)-4-(4-pent-2-ynyloxybenzenesulfonyl)-2,3,4,5-tetrahydro-1H-[1,4]benzodiazepine-3-carboxylic acid, hydroxyamide

EXAMPLE 21

1-(4-Fluoro-2-trifluoromethylbenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 22

1-(2-Fluoro-6-trifluormethylbenzoyl)-4-(4-pent-2 ynyloxybenzenesulfonyl)-2,3,4,5-tetrahydro-1H-[1,4]benzodiazepine-3-carboxylic acid, hydroxyamide

EXAMPLE 23

4-(4-But-2-ynyloxybenzenesulfonyl)-1-(2 methyl-6-chlorobenzoyl)-2,3,4,5-tetrahydro-1H-[1,4]benzodiazepine-3-carboxylic acid, hydroxyamide

EXAMPLE 24

1-(2,4-Dimethylbenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 25

1-(2,5-Dimethylbenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 26

1-(2-Chloro-4-flurobenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 27

1-(2-Chlorobenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 28

1-(2-Chlorobenzoyl)-4-(-4-pent-2-ynyloxybenzenesuffonyl)-2,3,4,5-tetrahydro-1H-[1,4]benzodiazepine-3-carboxylic acid, hydroxyamide

EXAMPLE 29

1-(2-Fluorobenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 30

1-(2-Chloro-6-fluorobenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 31

1-(2,3-Difluorobenzoyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 32

1-(2,4-Dichlorobenzoyl)-4-(4-[4-metboxybut-2-ynyloxy]benzenesulfonyl)-2,3,4,5-tetrahydro-1H-[1,4]benzodiazepine-3-carboxylic acid, hydroxyamide

EXAMPLE 33

1-(2,4-Dichlorobenzoyl)-4-(4-pent-2-ynyloxybenzenesulfonyl)-2,3,4,5-tetrahydro-1H-[1,4]benzodiazepine-3-carboxylic acid, hydroxyamide

EXAMPLE 34

1-(2,3-Dichlorobenzoyl)-4-(4-[4-metboxybut-2-ynxloxy]benzenesulfonyl)-2,3,4,5-tetrahydro-1H-[1,4]benzodiazepine-3-carboxylic acid, hydroxyamide

EXAMPLE 35

1-(2,5-Dichlorobenzoyl)-4-(4-[4-hydroxybut-2-ynyloxy]benzenesulfonyl)-2,3,4,5-tetrahydro-1H-[1,4]benzodiazepine-3-carboxylic acid, hydroxyamide

EXAMPLE 36

1-(Benzoyl)-4-(4-pent-2-ynyloxybenzenesulfonyl)-2,3,4,5-tetrahydro-1H-[1,4)benzodiazepine-3-carboxylic acid, hydroxyamide

EXAMPLE 37

4-(4-But-2-ynyloxybenzenesulfony)-1-(2-methylthiobenzoyl)-2,3,4,5-tetrahydro-1H-[1,4]benzodiazepine-3-carboxylic acid, hydroxyamide

EXAMPLE 38

4-(4-But-2-ynyloxybenzenesulfony)-1-(3-methyl-2-thienylcarbonyl)-2,3,4,5-tetrahydro-1H-[1,4]benzodiazepine-3-carboxylic acid, hydroxyamide

EXAMPLE 39

4-(4-[4-Hydroxybut-2-ynyloxy]benzenesulfonyl)-1-(4 methyl-2-thienylcarbonyl)-2,3,4,5-tetrahydro-1H-[1,4]benzodiazepine-3-carboxylic acid, hydroxyamide

EXAMPLE 40

1-(3-Chloro-2-thienylcarbonyl)-4-(4-[4-dimethylaminobut 2-ynyloxy]benzenesulfonyl)-2,3,4,5-tetrahydro-1H-[1,4]benzodiazepine-3-carboxylic acid, hydroxyamide

EXAMPLE 41

1-(2-Furanylcarbonyl)-4-(4-[4-methylaminobut-2-ynyloxy]benzenesulfonyl)-2,3,4,5-tetrahydro-1H-[1,4]benzodiazepine-3-carboxylic acid, hydroxyamide

EXAMPLE 42

4-(4-But-2-ynyloxybenzenesulfonyl)-1-(3-methyl-2-furanylcarbonyl)-2,3,4,5-tetrahydro-1H-[1,4]benzodiazepine-3-carboxylic acid, hydroxyamide

EXAMPLE 43

4-(4-[4-But-2-ynyloxybenzenesulfonyl)-1-(-4-methyl-2-furanylcarbonyl)-2,3,4,5-tetrahydro-1H-[1,4]benzodiazepine-3-carboxylic acid, hydroxyamide

EXAMPLE 44

1-(5-Chloro-2-furanylcarbonyl)-4-(4-[4-ethoxybut-2-ynyloxy]benzenesulfonyl)-2,3,4,5-tetrahydro-1H-[1,4]benzodiazepine-3-carboxylic acid, hydroxyamide

EXAMPLE 45

1-(5-Chloro-2-thienylcarbonyl)-4-(4-[4-hydroxybut-2-ynyloxy]benzenesulfonyl)-2,3,4,5-tetrahydro-1H-[1,4]benzodiazepine-3-carboxylic acid, hydroxyamide

EXAMPLE 46

1-Propionyl-4-(4-[4-hydroxybut-2-ynyloxy]benzenesulfonyl)-2,3,4,5-tetrahydro-1H-[1,4]benzodiazepine-3-carboxylic acid, hydroxyamide

EXAMPLE 47

1-Hexanoyl-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 48

4-(4-But-2-ynyloxybenzenesulfonyl)-1-(propionyl)-2,3,4,5-tetrahydro-1H-[1,4]benzodiazepine-3-carboxylic acid, hydroxyamide

EXAMPLE 49

4-(4-But-2-ynyloxybenzenesulfonyl)-1-(3-thienylcarbonyl)-2,3,4,5-tetrahydro-1H-[1,4]benzodiazepine-3-carboxylic acid, hydroxyamide

EXAMPLE 50

4-(4-But-2-ynyloxybenzenesulfonyl)-1-(3-furanycarbonyl)-2,3,4,5-tetrahydro-1H-[1,4]benzodiazepine-3-carboxylic acid, hydroxyamide

EXAMPLE 51

1-(Ethoxyacetyl)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 52

1-(Acetylaminoacetyl)-4-(4-but-2-ynyloxybenzenesulfonyl)-2,3,4,5-tetrahydro-1H-[1,4]benzodiazepine-3-carboxylic acid, hydroxyamide

EXAMPLE 53

1-(N,N-Dimethylaminoacety)-4-(4-[4-methoxybut-2-ynyloxy]benzenesulfonyl)-2,3,4,5-tetrahydro-1H-[1,4]benzodiazepine-3-carboxylic acid, hydroxyamide

EXAMPLE 54

1-(Cyclopropylcarbonyl)-4-(4-[4-methxybut-2-ynyloxy]benzenesulfonyl)-2,3,4,5-tetrahydro-1H-[1,4]benzodiazepine-3-carboxylic acid, hydroxyamide

EXAMPLE 55

1-(Cyclobutylcarbonyl)-4-(4-but-2-ynyloxybenzeneulfonyl)-2,3,4,5-tetrahydro-1H-[1,4]benzodiazepine-3-carboxylic acid, hydroxyamide

EXAMPLE 56

4-(4-But-2-ynyloxybenzenesulfonyl)-1-(triflouroacety)-2,3,4,5-tetrahydro-1H-[1,4]benzodiazepine-3-carboxylic acid, hydroxyamide

EXAMPLE 57

4-(4-But-2-ynyloxybenzenesulfonyl)-1-(2-furanylcarbonyl)-2,3,4,5-tetrahydro-1H-[1,4]benzodiazepine-3-carboxylic acid hydroxyamide To a solution of 3.0 g (6.38 mmol) of methyl 1-(2 furanylcarbonyl)-4-(4-methoxybenzenesulfonyl)-2,3,4,5-tetrahydro-1H-[1,4]benzodiazepine-3-carboxylate in., 15 ml of $CH_2Cl_2$ (cooled to 0° C.) was added dropwise 12.8 ml (2.8 mmol) of $BBr_3$ in $CH_2Cl_2$ (1.0 M in $CH_2Cl_2$). The mixture was stirred at room temperature for 3 days, diluted with $CH_2Cl_2$ and then ice was added. The organic layer was separated, washed with $H_2O$, brine and dried (($Na_2SO_4$). The solvent was removed and the residue chromatographed on silica gel (flash column) with ethyl acetate-hexane, (1:1) as solvent. The fractions containing product were combined, the solvent removed and the residue triturated with ethyl acetate. Chilling and filtering gave 0.72 g of methyl 1-(2-furanylcarbonyl)-4-hydroxybenzenesulfonyl)-2,3,4,5-tetrahydro-1H-[1,4]benzodiazepine-3-carboxylate as a white solid, mp 204–206° C.; Anal Cal'd for $C_{22}H_{20}N_2O_7S$: C, 57.9; H, 4.2; N, 6.1. Found: C, 57.2; H,4.3; N, 6.0. To 1.26 g (4.82 mmol) of triphenylphosphine in 10 ml of toluene and 2.5 ml of tetrahydrofuran was added 360 uL (4.82 mmol) of 2-butyn-1-ol and 1.48 g (3.2 mmol)of methyl 1-(2-furanylcarbonyl)-4-(4-hydroxybenzenesulfonyl)-1H-[1,4]benzo-diazepine-3-carboxylate. Under nitrogen was added 760 µL, (4.8 mmol) of diethyl azodicarboxylate and the mixture stirred for 2 days at room temperature. The solvent was removed under vacuum and the residue chromatographed on silica gel with ethyl acetate-hexane(1:1) as solvent. The fractions containing product were combined and the solvent removed to give a solid. Trituration with ethyl acetate followed by chilling and filtering gave 2.2 g of white solid. The solid was recrystallized from ethyl acetate to give 1.53 g of methyl 1-(2-furanylcarbonyl)-4-(4-but-2-ynyloxybenzenesulfonyl)-2,3,4,5-tetrahydro-1H-[1,4]benzodiazepine-3-carboxylate as a solid, mp 119°–120° C.; Mass Spectrum (ES) 509.5(M+H).

To 1.8 g (3.54 mmol) of the preceding compound in 10 ml of tetrahydrofuran was added 4.6 ml (4.6 mmol) of 1N KOH. The mixture was stirred at room temperature for 2.5 hr and diluted with $H_2O$ and ethyl acetate. The aqueous layer was separated and acidified with 1N HCl. The mixture was extracted with ethyl acetate, the extract washed with brine and dried ($Na_2SO_4$). The solvent was removed to give 1.05 g of 1-(2-furanylcarbony)-4-(4-but-2-ynyloxybenzenesulfonyl)-2,3,4,5-tetradydro-1H-[1,4]benzodiazepine-3-carboxylic acid as a white foam; Mass Spectrum (ES) 495.5(M+H); Anal Calc'd for $C_{25}H_{22}N_2O_7S$: C, 60.7; H, 4.5; N, 5.7. Found: C, 57.6; H, 4.8; N, 6.6.

To a solution of 3.4 ml (6.8 mmol) of oxalyl chloride (2.0M solution in $CH_2Cl_2$) in 8 ml of $CH_2Cl_2$ (0° C.) was added 527 µL of N,N-dimethylformamide. To the solution was added a solution of 0.84 g (1.7 mmol) of the preceding acid in 3 ml of N,N-dimethylformamide. The mixture was stirred at room temperature under nitrogen for 1.5 hr. (Solution A).

In a separate flask, 1.56 ml (25.5 mmol) of hydroxylamine (50% in $H_2O$) was diluted with 6 ml of tetrahydrofuran and the solution chilled to 0° (Solution B). The Solution A was added slowly to the Solution B and the mixture stirred overnight at room temperature. The mixture was diluted with $CH_2Cl_2$ and the solution washed with $H_2O$, 2N citric acid, 1M $NaHCO_3$ and concentrated to dryness. The solid residue was chromatographed on silica gel (flash column) with ethyl acetate-hexane (1:1) as solvent to remove impurities. The product was eluted with 10% methonal in ethyl acetate. The combined product fractions were concentrated and dilluted with ethyl acetate and the solution dried ($Na_2SO_4$). The solvent was removed to give a solid which was dried 20 hr at 80° C. under vacuum to give 0.64 g of the product hydroxamic acid.

EXAMPLE 58

1-Cyclopropylcarbonyl-4-(4-but-ynyloxybenzenesulfonyl)-2,3,4,5-tetrahydro-1H-[1,4]benzodiazepine-3-carboxylic acid, hydorxyamide To a solution of 4.44 g(10 mmol) of methyl 1-cyclopropylcarbonyl-4-(4-methoxybenzenefulfonyl)-2,3,4-tetrahydro-1H-[1,4]benzodiaxepine -3-carboxylate in 25 ml of $CH_2Cl_2$ chilled to 0° C. was added dropwise 22 ml (22 mmol) of $BBr_3$ in $CH_2Cl_2$ (1.0 molar solution). The mixture was stirred overnight, cooled and diluted with ice and $H_2O$. Dichloromethane was added and the organic layer separated and washed with $H_2O$, brine and dried ($Na_2SO_4$). The solvent was removed under vacuum to give a solid which was chromatographed on silica gel with the solvent ethyl acetate-hexane (1:1) to give 1.0 g of methyl 1-cyclopropylcarbonyl-4-(4-hydroxybenzene-sulfonyl)-2,3,4,5-tetrahydro-1H-[1,4]benzodiazepine-3-carboxylate as a foam.

As described for Example 57, 0.45 g (1.09 mmol) of the preceding compound and 123 µL (1.64 mmol) of 2-butyn-1-ol were coupled with 0.430 g (1.64 mmol) of tripbenylphosphine and 2.59 µL (1.64 mol) of diethyl azodicarboxylate in 3.5 ml of toluene and 1 ml of tetrahydrofuran as solvent. The product was purified by chromatography on silica gel with ethyl acetate-hexane (1:15) as solvent to give 0.60 g of methyl 4-(4-but-2-ynyloxybenzenesulfonyl)-1-(cyclopropylcarbonyl)-2,3,4,5-tetrahydro-1H-[1,4]benzodiazepine-3-carboxylate as a solid. A solution of the preceding compound (0.57 g; 1.18 mmol) in a mixture of 1.5 ml (1.53 mol) of 1N KOH and 3 ml of tetrahydrofuran was stirred 3 hours; concentrated and extracted with ethyl acetate. The aqueous residue was acidified with 1N HCl and extracted with ethyl acetate. The extract was washed with brine, dried ($Na_2SO_4$) and the solvent removed to give 0.23 g of 4-(4-but-2-ynyloxybenzenesulfonyl)-1-(cyclopropylcarbonyl)-2,3,4,5-tetrahydro-1H-[1,4]benzodiazepine-3-carboxylic acid as an off-white solid.

As described for Example 57, 0.20 g (0.427 mmol) of the preceding compound was reacted with 855 µL (1.7 mmol) of N,N-dimethylformanide (DMF) in 3 ml of $CH_2Cl_2$ and 1 ml of DMF followed by reaction with 393µL (6.41 mmol ) of hydroxylamine (50% in $H_2O$) in 2 ml of tetrahydrofuran to the product was dried at 80° C. overnight to give 0.188 g of a white foam; Mass Spectrum (ES) 484.5(M+H); Anal Calc'd for $C_{24}H_{25}N_3O_6S$: C, 59.6; H, 5.2; N, 8.7. Found: C, 56.2; H, 5.1; N, 8.6.

EXAMPLE 59

(5-Fluoro-2-nitrophenyl) methanol

To 5-fluoro-2-nitrobenzoic acid (0.5 g, 2.7 mmol) was added a solution of borane-tetrahydrofuran complex (5 mL, 1.0 M, 5 mmol) and the resulting solution was heated to 70° C. for 3 hours. The reaction was then cooled to room temperature and methanol was added. The mixture was concentrated and methanol was added two additional times to provide 0.48 g (100%) of a white solid. mp 82–86° C. Anal Calc'd for $C_7H_6N_3O_3F$: C, 49.13; H, 3.52; N, 8.18. Found: C, 48.76; H, 3.56; N, 7.88.

EXAMPLE 60

2-(Bromomethyl)-4-fluoro-1-nitrobenzene

To a solution of (5-Fluoro-2-nitrophenyl) methanol (0.3 g, 1.75 mmol) in methylene chloride (5 mL0 was added triphenylphosphine (0.52 g, 2.01 mmol) and carbon tetrabromide (0.66 g, 2.01 mmol). After 3 hours, the reaction was concentrated and chromatographed using 3:1 hexane:ethyl acetate as eluant to provide 0.38 g (93%) of the desired product as white crystals. mp 38–41° C. Anal Calc'd for $C_7H_5N_3O_2FBr$: C, 35.93; H, 2.15; N, 5.99. Found: C, 35.97; H, 2.12; N, 5.91.

EXAMPLE 61

Methyl 2-({[4-(2-butynyloxy)phenyl]sulfonyl}amino)-3-hydroxypropanoate

Using the procedure of reference example 170, glycine methyl ester hydrochloride was converted to the corresponding sulfonamide using 4-But-2-ynyloxybenzenesulfonyl chloride to provide methyl 2-({[4-(2-butynyloxy)phenyl]sulfonyl}amino)-3-hydroxypropanoate.

EXAMPLE 62

Methyl 2-{(5-fluoro-2-nitrobenzyl)[(4-methoxyphenyl)sulfonyl]amino}-3-hydroxypropanoate To a solution was of 2-(bromomethyl)-4-fluoro-1-nitrobenzene (1.3 g, 5.56 mmol) at 0° C. was added tetrabutylammonium iodide (2.05 g, 5.56 mmol). The solution was stirred at 0° C. for 1.5 hours. In a separate flask, methyl 2-({[4-(2-butynyloxy)phenyl]sulfonyl}amino)-3-hydroxypropanoate (1.73 g, 5.05 mmol) was dissolved in dimethylformamide and cooled to 0° C. Sodium hydride (0.21 g, 5.56 mmol, 60% dispersion in oil) was added and the reaction was allowed to stir at 0° C. for 0.5 hours at which time the solution of the bromide was added. The reaction was stirred overnight and then quenched with water. The mixture was extracted twice with ethyl acetate, washed with brine, dried over $Na_2SO_4$, concentrated in vacuo and chromatographed using 1.5:1 hexane:ethyl acetate as eluant to provide 1.88 g (77%) of the desired product as a white solid. mp 83–88° C. Anal Calc'd for $C_{21}H_{21}N_2O_8FS$: C, 52.50; H, 4.41; N, 5.83. Found: C, 52.44; H, 4.76; N, 5.56.

EXAMPLE 63

Methyl 2-((2-amino-5-fluorobenzyl){[4-(2-butynyloxy)phenyl]sulfonyl}amino)-3-hydroxypropanoate Methyl 2-{(5-fluoro-2-nitrobenzyl)[(4-methoxyphenyl)sulfonyl]amino}-3-hydroxypropanoate (1.0 g, 2.08 mmol) was dissolved in ethanol (18 mL). To this was added tin chloride dihydrate (2.35 g, 10.4 mmol) and the reaction was heated to 70° C. for 2 hours. The reaction was then cooled to room temperature and ice water followed by $NaHCO_3$ was added to bring the solution to pH 8. Ethyl acetate was added and the suspension was filtered through celite. The organic layer was separated and washed with brine, dried over $Na_2SO_4$ concentrated in vacuo and chromatographed using 1:1 hexane:ethyl acetate as eluant to provide 0.55 g (58%) of the desired product as a yellow oil.

EXAMPLE 64

Methyl 1-acetyl-4-{[4-(2-butynyloxy)phenyl]sulfonyl}-7-fluoro-2,3,4,5-tetrahydro-1H-1,4-benzodiazepine-3-carboxylate Methyl-2-((2-amino-5-fluorobenzyl){[4-(2-butynyloxy)phenyl]-sulfonyl}amino)-3-hydroxypropanoate (0.48 g, 1.07 mmol) was converted to the desired product 0.41 g, (95%) using acetyl chloride as the acylating agent by following the procedure outlined in reference example 181. Anal Calc'd for $C_{23}H_{23}N_2O_6FS$: C, 58.22; H, 4.89; N, 5.90. Found: C, 57.58; H, 4.95; N, 5.60.

EXAMPLE 65

1-Acetyl-4-{[4-(2-butynyloxy)phenyl]sulfonyl}-7-fluoro-2,3,4,5-tetrahydro-1H-1,4-benzodiazepine-3-carboxylic acid Methyl 1-acetyl-4-{[4-(2-butynyloxy)phenyl]sulfonyl}-7-fluoro-2,3,4,5-tetrahydro-1H-1,4-benzodiazepine-3-carboxylate was hydrolized to the carboxylic acid utilizing the procedure from reference example 185 to provide the desired acid as an off white solid. Anal Calc'd for $C_{22}H_{21}N_2O_6FS$: C, 57.38; H, 4.6; N, 6.08. Found: C, 56.93; H, 4.71; N, 5.67.

EXAMPLE 66

1-Acetyl-4-{[4-(2-butynyloxy)phenyl]sulfonyl}-7-fluoro-N-hydroxy-2,3,4,5-tetrahydro-1H-1,4-benzodiazepine-3-carboxamide Using the procedure of example 3,1-acetyl-4-{[4-(2-butynyloxy)phenyl]-sulfonyl}-7-fluoro-2,3,4,5-tetrahydro-1H-1,4-benzodiazepine-3-carboxylic acid was converted to the hydroxamic acid 45 mg (15%). Mass Spectrum (ES) 476.2 (M+H).

What is claimed is:
1. A compound of Formula 1:

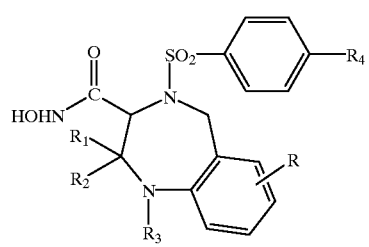

wherein

R is selected from hydrogen, $(C_1-C_3)$ alkyl, —CN, —OR', —SR', —CF$_3$, —OCF$_3$, Cl, F, —N(R')CO$(C_1-C_3)$alkyl, —N(R')(R'), NO$_2$, —CONH$_2$, —SO$_2$NH$_2$, —SO$_2$N(R')(R'), —N(R')COCH$_2$O—$(C_1-C_3)$alkyl, wherein R' is $(C_1-C_3)$ alkyl or hydrogen;

$R_4$ is $(C_2-C_6)$ alkyl-O— containing one triple bond,

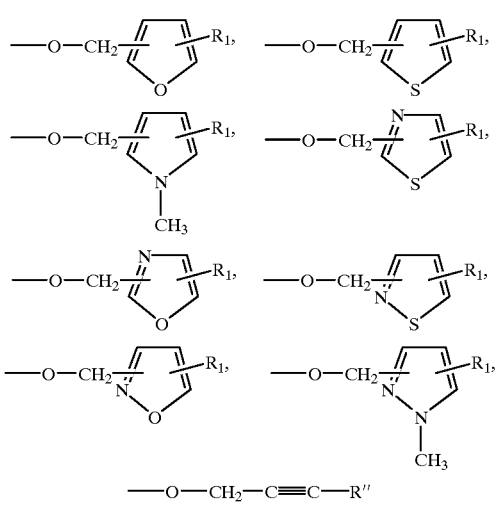

wherein R" is hydrogen, —$CH_2OH$, $(C_1-C_6)$alkyl, $(C_1-C_6)$alkyl-O—$CH_2$—, $(C_1-C_6)$alkyl-S—$CH_2$—, $(C_1-C_6)$alkyl-NH—$CH_2$—, $[(C_1-C_3)$alkyl$]_2$-$NCH_2$—, $(C_3-C_6)$cycloalkyl-O—$CH_2$—, $[(C_1-C_3)$ alkyl$]_2$-N—$(CH_2)_{2-4}NHCH_2$—, $[(C_1-C_3)$ alkyl$]_2$-N—$(CH_2)_{2-4}N(CH_3)CH_2$—,

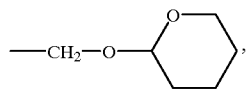

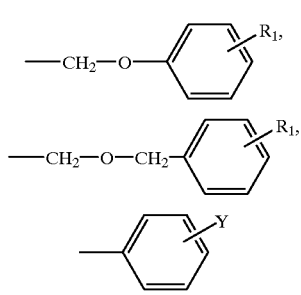

$R_1$ and $R_2$ are each, independently, hydrogen or $C_1-C_3$ alkyl, $R_3$ is $(C_1-C_8)$alkyl, $NH_2CH_2CO$—, $(C_1-C_6)$alkylNHCH$_2$CO—, $HO(CH_2)_mCO$—, HCO—, Aryl$(CH_2)_nCO$—, Heteroaryl$(CH_2)_nCO$—, $(C_1-C_3)$alkyl-O—$(CH_2)_nCO$—, $(C_1-C_3)$alkylCO—, $(C_1-C_3)$alkylCO—NHCH$_2$CO—, $(C_3-C_7)$cycloalkylCO—, $(C_1-C_3)$alkylSO$_2$—, Aryl$(CH_2)_nSO_2$—, Heteroaryl$(CH_2)_nSO_2$—, $(C_1-C_3)$alkyl-O—$(CH_2)_m$—$SO_2$—, $(C_1-C_3)$alkyl-O—$(CH_2)_m$—, $(C_1-C_3)$alkyl-O—$(C_1-C_3)$alkyl-O—$(C_1-C_3)$alkyl—, HO—$(C_1-C_3)$alkyl-O—$(C_1-C_3)$alkyl-, Aryl-O—$CH_2CO$—, Heteroaryl-O—$CH_2CO$—, ArylCH=CHCO—, HeteroarylCH=CHCO—, $(C_1-C_3)$alkylCH=CHCO—,

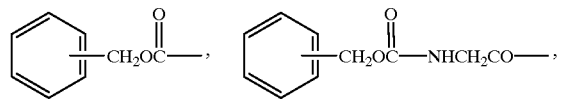

Aryl$(C_1-C_3)$alkyl-, Heteroaryl$(C_1-C_3)$alkyl-, ArylCH=CHCH$_2$—, HeteroarylCH=CHCH$_2$—, $(C_1-C_6)$alkylCH=CHCH$_2$—,

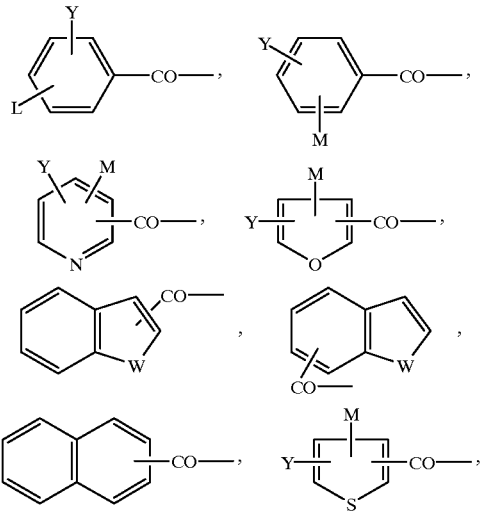

R'OCH$_2$CH(OR')CO—, (R'OCH$_2$)$_2$C(R')CO—,

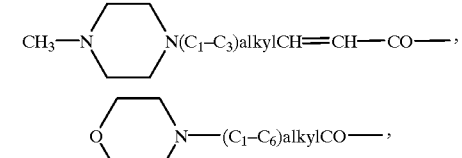

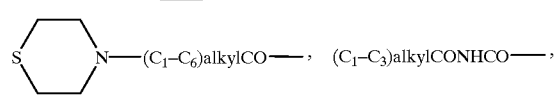

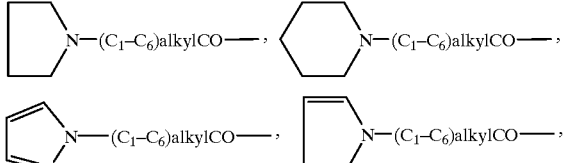

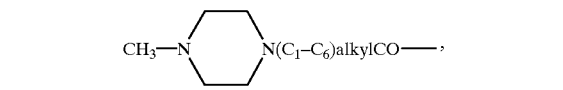

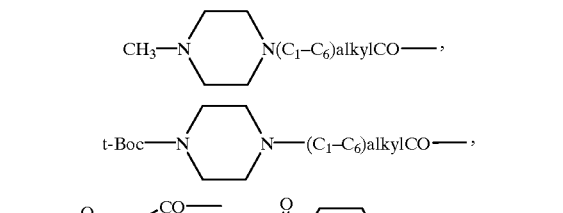

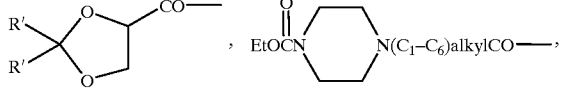

M is

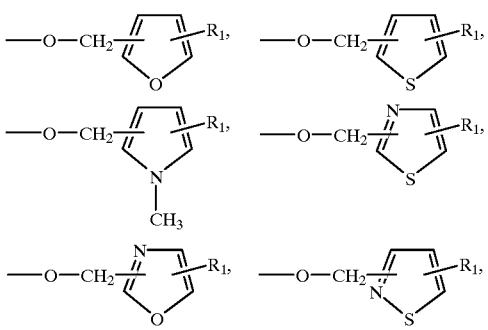

or N(R')(R') where R' is as defined above;

W is O, S, NH or N($C_1$–$C_3$)alkyl;

Y is hydrogen, F, Cl, $CF_3$ or $OCH_3$; and X' is halogen, hydrogen, ($C_1$–$C_3$)alkyl, O—($C_1$–$C_3$)alkyl, or —$CH_2OH$; and pharmaceutically acceptable salts thereof.

2. A compound according to claim 1, wherein:

R is hydrogen, ($C_1$–$C_3$) alkyl, —CN, —OR', —SR', —$CF_3$, —$OCF_3$, Cl, F, —N(R')CO($C_1$–$C_3$)alkyl, —N(R')(R'), $NO_2$, —$CONH_2$, —$SO_2NH_2$, —$SO_2N(R')$ (R'), or —N(R')COCH$_2$O—($C_1$–$C_3$)alkyl, wherein R' is ($C_1$–$C_3$) alkyl or hydrogen;

$R_4$ is ($C_1$–$C_6$) alkyl-O— containing one triple bond,

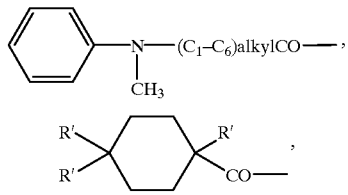

[($C_1$–$C_6$)alkyl]$_2$-N—($C_1$–$C_6$)alkyl CO—, or ($C_1$–$C_6$) alkyl-NH—($C_1$–$C_6$)alkylCO—;

wherein m=1 to 3; n=0 to 3

Aryl is

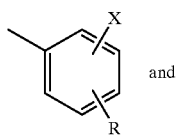

and

Heteroaryl is

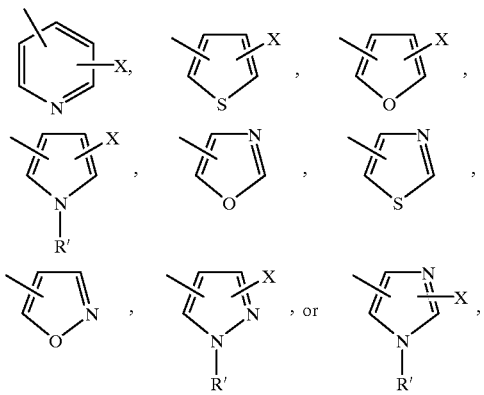

wherein

X is hydrogen, halogen, ($C_1$–$C_3$) alkyl or —$OCH_3$, and R and R' are as defined above;

L is hydrogen, ($C_1$–$C_3$)alkyl, —CN, —OR', —SR', —$CF_3$, —$OCF_3$, Cl, F, —N(R')CO($C_1$–$C_3$)alkyl, N(R')(R'), —$NO_2$, —$CONH_2$, —$SO_2NH_2$, —$SO_2N(R')(R')$, —N(R')COCH$_2$O—($C_1$–$C_3$)alkyl,

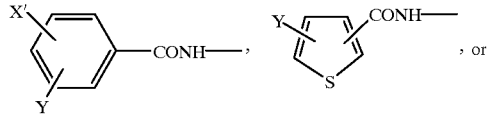

-continued

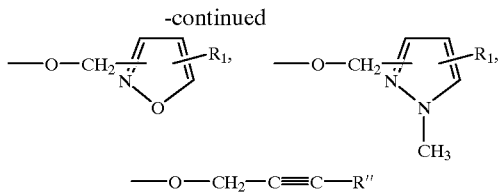

—O—CH₂—C≡C—R″ wherein R″ is hydrogen, —CH₂OH, (C₁–C₆)alkyl, (C₁–C₆)alkyl-O—CH₂—, (C₁–C₆)alkyl-S—CH₂—, (C₁–C₆)alkyl-NH—CH₂—, [(C₁–C₃)alkyl]₂-NCH₂—, (C₃–C₆)cycloalkyl-O—CH₂—, [(C₁–C₃)alkyl]₂-N—(CH₂)₂₋₄NHCH₂—, [(C₁–C₃)alkyl]₂-N—(CH₂)₂₋₄N(CH₃)C₂—,

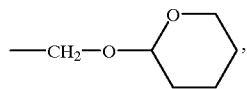

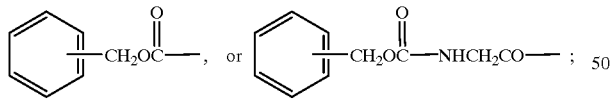

$R_1$ and $R_2$ are each, independently, hydrogen or $CH_3$;

$R_3$ is $(C_1-C_8)$alkyl, $NH_2CH_2CO$—, $(C_1-C_6)$alkylNHCH₂CO—, HO(CH₂)ₘCO—, HCO—, Aryl(CH₂)ₙCO—, Heteroaryl(CH₂)ₙCO—, $(C_1-C_3)$alkyl-O—(CH₂)ₙCO—, $(C_1-C_3)$alkylCO—, $(C_1-C_3)$alkylCO—NHCH₂CO—, $(C_3-C_7)$cycloalkylCO—, Aryl-O—CH₂CO—, HeteroarylOCH₂CO—,

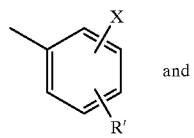

wherein m=1 to 3; n=0 to 3;

Aryl is

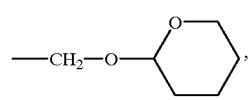

and

Heteroaryl is

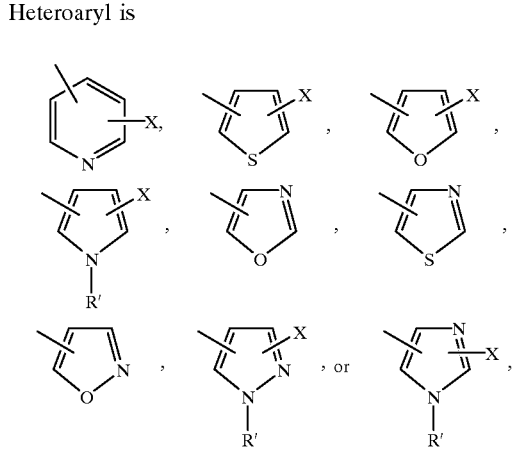

wherein X is hydrogen, halogen, $(C_1-C_3)$ alkyl or —OCH₃ wherein R and R′ are as defined above; and pharmaceutically acceptable salts thereof.

3. A compound according to claim 1, wherein

R is hydrogen, $(C_1-C_3)$ alkyl, —CN, —OR′, —SR′, —CF₃, —OCF₃, Cl, F, —N(R′)CO(C₁–C₃)alkyl, —N(R′)(R′), NO₂, —CONH₂, —SO₂NH₂, —SO₂N(R′)(R′), —N(R′)COCH₂O—(C₁–C₃)alkyl, wherein R′ is $(C_1-C_3)$ alkyl or hydrogen;

$R_4$ is $(C_2-C_6)$ alkyl-O— containing one triple bond,

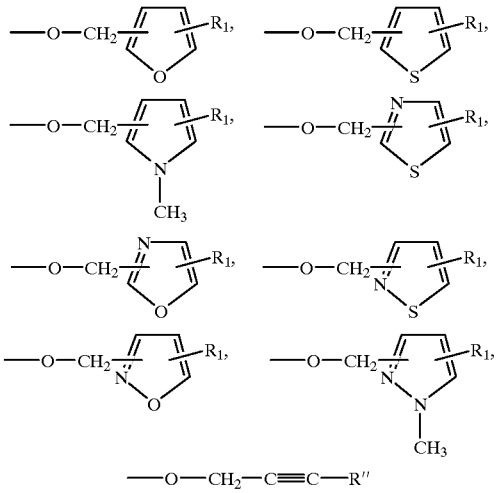

—O—CH₂—C≡C—R″ wherein R″ is hydrogen, —CH₂OH, (C₁–C₆)alkyl, (C₁–C₆)alkyl-O—CH₂—, (C₁–C₆)alkyl-S—CH₂—, (C₁–C₆)alkyl-NH—CH₂—, [(C₁–C₃)alkyl]₂-NCH₂—, (C₃–C₆)cycloalkyl-O—CH₂—, [(C₁–C₃) alkyl]₂-N—(CH₂)₂₋₄NHCH₂—, [(C₁–C₃) alkyl]₂-N—(CH₂)₂₋₄N(CH₃)CH₂—,

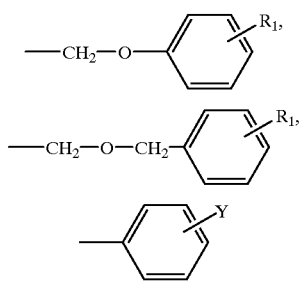

$R_1$ and $R_2$ are each, independently, hydrogen or $CH_3$;

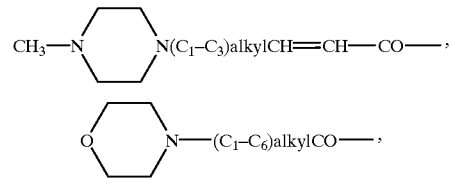

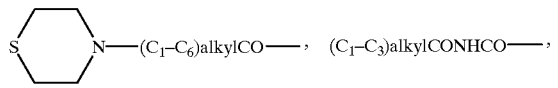

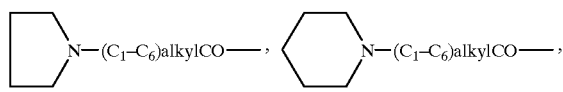

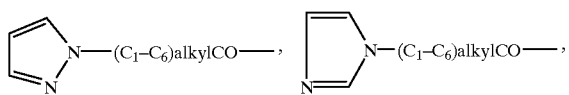

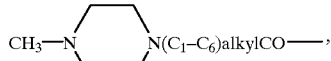

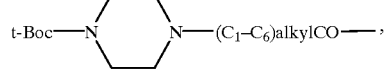

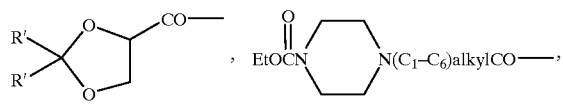

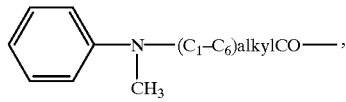

$[(C_1-C_6)alkyl]_2$-N—$(C_1-C_6)$alkyl CO—, or $(C_1-C_6)$alkyl-NH—$(C_1-C_6)$alkylCO—, where R' is as defined above;

and pharmaceutically acceptable salts thereof.

4. A compound according to claim 1, wherein

R is hydrogen, $(C_1-C_3)$ alkyl, —CN, —OR', —SR', —$CF_3$, —$OCF_3$, Cl, F, —N(R')CO$(C_1-C_3)$alkyl, —N(R')(R'), $NO_2$, —$CONH_2$, —$SO_2NH_2$, —$SO_2N(R')$(R'), —N(R')$COCH_2O$—$(C_1-C_3)$alkyl, wherein R' is $(C_1-C_3)$ alkyl or hydrogen;

$R_4$ is $(C_1-C_6)$ alkyl-O— containing one triple bond,

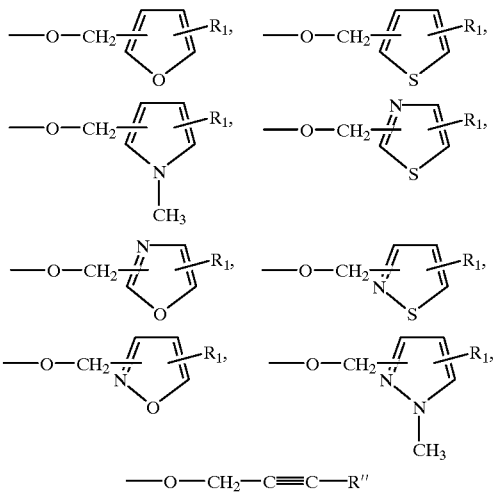

—O—$CH_2$—C≡C—R", wherein R" is hydrogen, —$CH_2OH$, $(C_1-C_6)$alkyl, $(C_1-C_6)$alkyl-O—$C_2$—, $(C_1-C_6)$alkyl-S—$C_2$—, $(C_1-C_6)$alkyl-NH—$C_2$—, $[(C_1-C_3)alkyl]_2$-$NCH_2$—, $(C_3-C_6)$cycloalkyl-O—$C_2$—, $[(C_1-C_3)$ alkyl$]_2$-N—$(CH_2)_{2-4}NHCH_2$—, $[(C_1-C_3)$ alkyl$]_2$-N—$(CH_2)_{2-4}N(CH_3)CH_2$—,

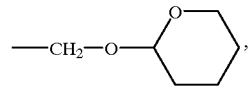

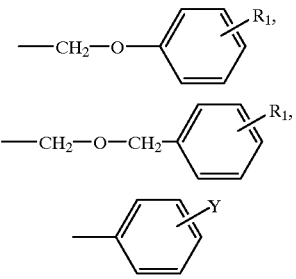

$R_1$ and $R_2$ are each, independently, hydrogen or $CH_3$;

$R_3$ is $(C_1-C_3)$alkyl$SO_2$—, Aryl$(CH_2)_nSO_2$—, Heteroaryl$(CH_2)_nSO_2$—, or $(C_1-C_3)$alkyl-O—$(CH_2)_m$—$SO_2$—, wherein m=1 to 3; n=0 to 3;

Aryl is

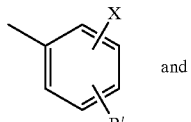

and

Heteroaryl is

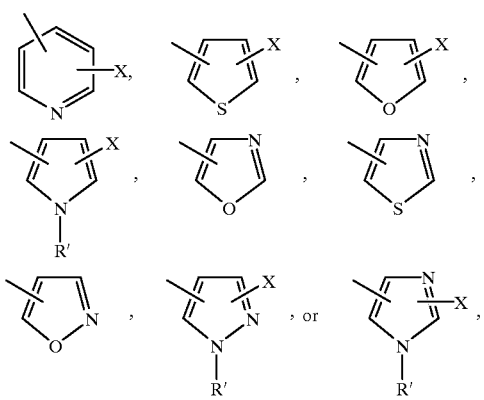

wherein X is hydrogen, halogen, ($C_1$–$C_3$) alkyl or —OCH3 and R and R' are as defined above; and pharmaceutically acceptable salts thereof.

5. A compound according to claim 1, wherein

R is hydrogen, ($C_1$–$C_3$) alkyl, —CN, —OR', —SR', —$CF_3$, —$OCF_3$, Cl, F, —N(R')CO($C_1$–$C_3$)alkyl, —N(R')(R'), $NO_2$, —$CONH_2$, —$SO_2NH_2$, —$SO_2N(R')$(R'), or —N(R')$COCH_2O$—($C_1$–$C_3$)alkyl, wherein R' is ($C_1$–$C_3$) alkyl or hydrogen;

$R_4$ is ($C_1$–$C_6$) alkyl-O— containing one triple bond, —O—$CH_2$—C≡C—R"

wherein

R" is hydrogen, —$CH_2OH$, ($C_1$–$C_6$)alkyl, ($C_1$–$C_6$)alkyl-O—$C_2$—, ($C_1$–$C_6$)alkyl-S—$CH_2$—, ($C_1$–$C_6$)alkyl-NH—$CH_2$—, [($C_1$–$C_3$)alkyl]$_2$-$NCH_2$—, ($C_3$–$C_6$) cycloalkyl-O—$CH_2$—, [($C_1$–$C_3$) alkyl]$_2$-N—($CH_2$)$_{2-4}$$NCH_2$—, [($C_1$–$C_3$) alkyl]$_2$-N—($CH_2$)$_{2-4}$N($CH_3$)$CH_2$—,

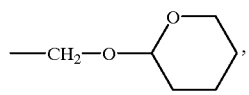

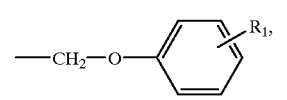

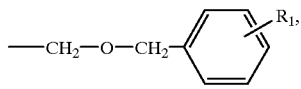

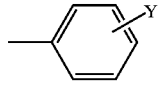

$R_1$ and $R_2$ are each, independently, hydrogen or $CH_3$;

$R_3$ is HCO—, ($C_1$–$C_3$)alkylCO—, Aryl($C_1$–$C_3$) alkylCO—, Heteroaryl($C_1$–$C_3$)alkylCO—, ($C_1$–$C_3$) alkyl-O—($CH_2$)$_n$CO—, HO($CH_2$)$_m$CO—, ($C_3$–$C_7$) cycloalkylCO—, wherein Aryl is

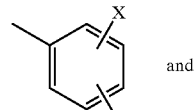 and

Heteroaryl is

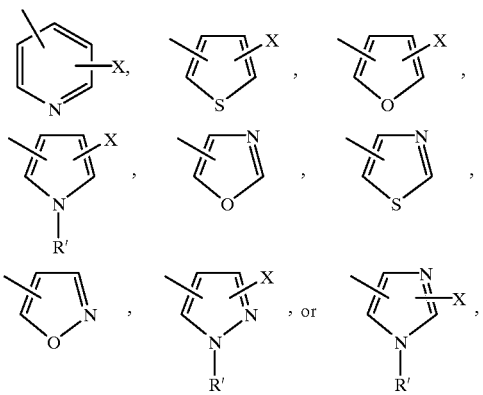

wherein X is hydrogen, halogen, ($C_1$–$C_3$) alkyl or —$OCH_3$ and R and R' are is as defined above;

and pharmaceutically acceptable salts thereof.

6. A compound according to claim 1, wherein

R is hydrogen, ($C_1$–$C_3$) alkyl, —CN, —OR', —SR', —$CF_3$, —$OCF_3$, Cl, F, —N(R')CO($C_1$–$C_3$)alkyl, —N(R')(R'), $NO_2$, —$CONH_2$, —$SO_2NH_2$, —$SO_2N(R')$(R'), or —N(R')$COCH_2O$—($C_1$–$C_3$)alkyl, wherein R' is ($C_1$–$C_3$) alkyl or hydrogen;

$R_4$ is ($C_2$–$C_6$) alkyl-O— containing one triple bond, —O—$CH_2$—C≡C—R"

wherein R" is hydrogen, —$CH_2OH$, ($C_1$–$C_6$)alkyl, ($C_1$–$C_6$)alkyl-O—$C_2$—, ($C_1$–$C_6$)alkyl-S—$C_2$—, ($C_1$–$C_6$)alkyl-NH—$C_2$—, [($C_1$–$C_3$)alkyl]$_2$-$NCH_2$—, ($C_3$–$C_6$)cycloalkyl-O—$C_2$—, [($C_1$–$C_3$) alkyl]$_2$-N—($CH_2$)$_{2-4}$$NHCH_2$—, [($C_1$–$C_3$) alkyl]$_2$-N—($CH_2$)$_{2-4}$N($CH_3$)$CH_2$—,

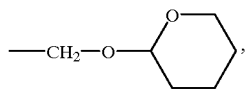

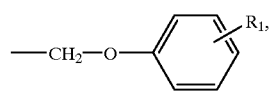

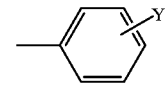

$R_1$ and $R_2$ are each, independently, hydrogen or $CH_3$;
$R_3$ is

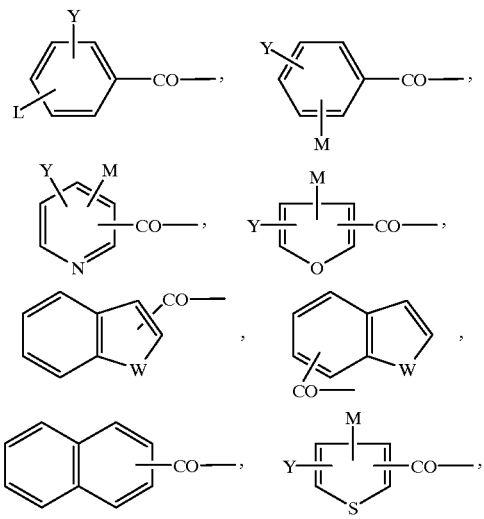

wherein
m=1 to 3; n=0 to 3;
L is hydrogen, $(C_1-C_3)$alkyl, —CN, —OR', —SR', —$CF_3$, —$OCF_3$, Cl, F, —N(R')CO($C_1-C_3$)alkyl, N(R')(R'), —$NO_2$, —$CONH_2$, —$SO_2NH_2$, —$SO_2N(R')(R')$, —N(R')$COCH_2O$—($C_1-C_3$)alkyl,

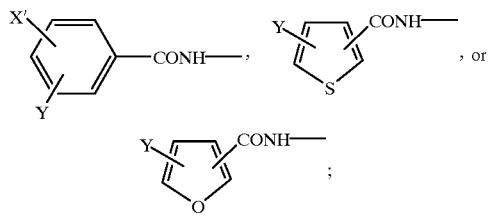

M is

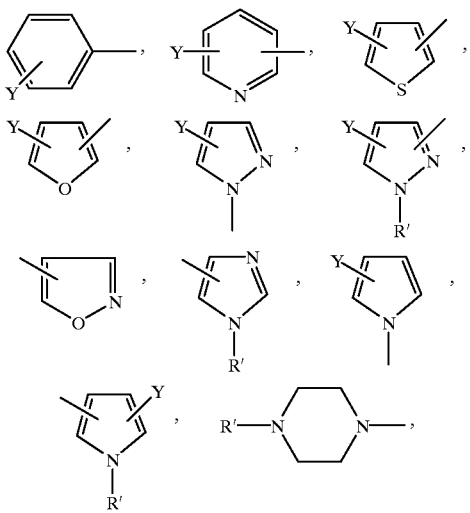

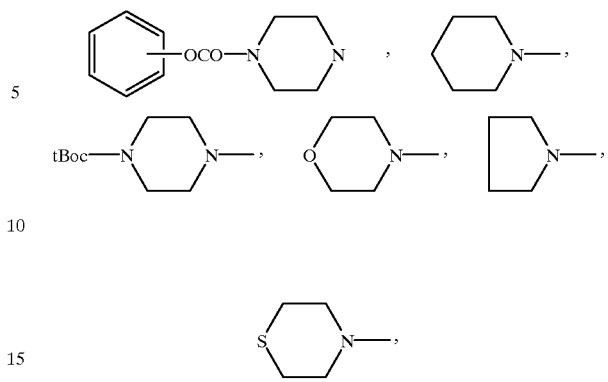

or N(R')(R') where R' is as defined above;
W is O, S, NH or N($C_1-C_3$)alkyl;
Y is hydrogen, F, Cl, $CF_3$ or $OCH_3$; and X' is halogen, hydrogen, ($C_1-C_3$)alkyl, O—($C_1-C_3$)alkyl, or —$CH_2OH$; and pharmaceutically acceptable salts thereof.

7. The compound according to claim 1 which is 1-Acetyl-4-(4-but-2-ynyloxy-benzenesulfonyl)-2,3,4,5-tetrahydro-1H-[1,4]benzodiazepine-3-carboxylic acid, hydroxyamide.

8. The compound according to claim 1 which is 4-(4-But-2-ynyloxy-benzenesulfonyl)-1-(2-thienylcarbonyl)-2,3,4,5-tetrahydro-1H-[1,4]benzodiazepine-3-carboxylic acid, hydroxyamide.

9. The compound according to claim 1 which is 1-Benzoyl-4-(4-but-2-ynyloxybenzenesulfonyl)-2,3,4,5-tetrahydro-1H-[1,4]benzodiazepine-3-carboxylic acid, hydroxyamide.

10. The compound according to claim 1 which is 4-(4-But-2-ynyloxybenzenesulfonyl)-1-(2-furanylcarbonyl)-2,3,4,5-tetrahydro-1H-[1,4]benzodiazepine-3-carboxylic acid, hydroxyamide.

11. The compound according to claim 1 which is 4-(4-But-2-ynyloxybenzenesulfonyl)-1-(methanesulfonyl)-2,3,4,5-tetrahydro-1H-[1,4]benzodiazepine-3-carboxylic acid, hydroxyamide.

12. The compound according to claim 1 which is 4-(4-But-2-ynyloxybenzenesulfonyl)-1-methoxyacetyl-2,3,4,5-tetrahydro-1H-[11,4]benzodiazepine-3-carboxylic acid, hydroxyamide.

13. The compound according to claim 1 which is 4-(4-But-2-ynyloxybenzenesulfonyl)-1-(3-pyridinylcarbonyl)-2,3,4,5-tetrahydro-1H-[1,4]benzodiazepine-3-carboxylic acid, hydroxyamide.

14. The compound according to claim 1 which is 4-(4-But-2-ynyloxybenzenesulfonyl)-1-(4-pyridinylcarbonyl)-2,3,4,5-tetrahydro-1H-[1,4]benzodiazepine-3-carboxylic acid, hydroxyamide.

15. The compound according to claim 1 which is 1-Benzoyl-4-(4-[4-methoxybut-2-ynyloxy]benzenesulfonyl)-2,3,4,5-tetrahydro-1H-[1,4]benzodiazepine-3-carboxylic acid, hydroxyamide.

16. The compound according to claim 1 which is 4-(4-[4-Methoxybut-2-ynyloxy]benzenesulfonyl)-1-(3-pyridinylcarbonyl)-2,3,4,5-tetrahydro-1H-[1,4]benzodiazepine-3-carboxylic acid, hydroxyamide.

17. The compound according to claim 1 which is 4-(4-Pent-2-ynyloxy-benzenesulfonyl)-1-(3-pyridinylcarbonyl)-2,3,4,5-tetrahydro-1H-[1,4]benzodiazepine-3-carboxylic acid, hydroxyamide.

18. The compound according to claim 1 which is 4-(4-[4-Hydroxybut-2-ynyloxy]benzenesulfonyl)-1-(4-pyridinylcarbonyl)-2,3,4,5-tetrahydro-1H-[1,4]benzodiazepine-3-carboxylic acid, hydroxyamide.

19. The compound according to claim 1 which is 4-(4-[4-Methoxybut-2-ynyloxy]-benzenesulfonyl)-1-(2-thienylcarbonyl)-2,3,4,5-tetrahydro-1H-[1,4]benzodiazepine-3-carboxylic acid, hydroxyamide.

20. The compound according to claim 1 which is 1-(Benzoyl)-4-(4-pent-2-ynyloxy-benzenesulfonyl)-2,3,4,5-tetrahydro-1H-[1,4]benzodiazepine-3-carboxylic acid, hydroxyamide.

21. The compound according to claim 1 which is 1-Propionyl-4-(4-[4-hydroxybut-2-ynyloxy]benzenesulfonyl)-2,3,4,5-tetrahydro-1H-[1,4]benzodiazepine-3-carboxylic acid, hydroxyamide.

22. The compound according to claim 1 which is 1-(N,N-Dimethylaminoacetyl)-4-(4-[4-methoxybut-2-ynyloxy]benzenesulfonyl)-2,3,4,5-tetrahydro-1H-[1,4]benzodiazepine-3-carboxylic acid, hydroxyamide.

23. The compound according to claim 1 which is 1-(Acetylaminoacetyl)-4-(4-but-2-ynyloxybenzenesulfonyl)-2,3,4,5-tetrahydro-1H-[1,4]benzodiazepine-3-carboxylic acid, hydroxyamide.

24. The compound according to claim 1 which is 1-(Ethoxyacetyl)-4-(4-[4-methoxybut-2-ynyloxy]benzenesulfonyl)-2,3,4,5-tetrahydro-1H-[1,4]benzodiazepine-3-carboxylic acid, hydroxyamide.

25. The compound according to claim 1 which is 4-(4-But-2-ynyloxybenzenesulfonyl)-1-(3-thienylcarbonyl)-2,3,4,5-tetrahydro-1H-[1,4]benzodiazepine-3-carboxylic acid, hydroxyamide.

26. The compound according to claim 1 which is 1-(Ethoxyacetyl)-4-(4-[4-ethoxybut-2-ynyloxy]benzenesulfonyl)-2,3,4,5-tetrahydro-1H-[1,4]benzodiazepine-3-carboxylic acid, hydroxyamide.

27. The compound according to claim 1 which is 1-(Acetylaminoacetyl)-4-(4-[4-methoxybut-2-ynyloxy]benzenesulfonyl)-2,3,4,5-tetrahydro-1H-[1,4]benzodiazepine-3-carboxylic acid, hydroxyamide.

28. The compound according to claim 1 which is 1-(Cyclopropylcarbonyl)-4-(4-[4-methoxybut-2-ynyloxy]benzenesulfonyl)-2,3,4,5-tetrahydro-1H-[1,4]benzodiazepine-3-carboxylic acid, hydroxyamide.

29. The compound according to claim 1 which is 1-(Cyclobutylcarbonyl)-4-(4-but-2-ynyloxybenzeneulfonyl)-2,3,4,5-tetrahydro-1H-[1,4]benzodiazepine-3-carboxylic acid, hydroxyamide.

30. The compound according to claim 1 which is 4-(4-But-2-ynyloxybenzenesulfonyl)-1-(propionyl)-2,3,4,5-tetrahydro-1H-1,4]benzodiazepine-3-carboxylic acid, hydroxyamide.

31. The compound according to claim 1 which is 4-(4-[4-Methoxybut-2-ynyloxy]benzenesulfonyl)-1-(3-methyl-2-thienylcarbonyl)-2,3,4,5-tetrahydro-1H-[1,4]benzodiazepine-3-carboxylic acid, hydroxyamide.

32. The compound according to claim 1 which is 4-(4-But-2-ynyloxybenzenesulfonyl)-1-(3-methoxypropionyl)-2,3,4,5-tetrahydro-1H-[1,4]benzodiazepine-3-carboxylic acid, hydroxyamide.

33. The compound according to claim 1 which is 4-(4-But-2-ynyloxybenzenesulfonyl)-1-(2-chlorobenzoyl)-2,3,4,5-tetrahydro-1H-[1,4]benzodiazepine-3-carboxylic acid, hydroxyamide.

34. The compound according to claim 1 which is 4-(4-But-2-ynyloxybenzenesulfonyl)-1-(2-fluorobenzoyl)-2,3,4,5-tetrahydro-1H-[1,4]benzodiazepine-3-carboxylic acid, hydroxyamide.

35. The compound according to claim 1 which is 4-(4-But-2-ynyloxybenzenesulfonyl)-1-(4-methyl-2-furanylcarbonyl)-2,3,4,5-tetrahydro-1H-[1,4]benzodiazepine-3-carboxylic acid, hydroxyamide.

36. The compound according to claim 1 which is 4-(4-But-2-ynyloxybenzenesulfonyl)-1-(3-furanylcarbonyl)-2,3,4,5-tetrahydro-1H-[1,4]benzodiazepine-3-carboxylic acid, hydroxyamide.

37. The compound according to claim 1 which is 4-(4-But-2-ynyloxybenzenesulfonyl)-1-(phenoxyacetyl)-2,3,4,5-tetrahydro-1H-[1,4]benzodiazepine-3-carboxylic acid, hydroxyamide.

38. The compound according to claim 1 which is 4-(4-But-2-ynyloxybenzenesulfonyl)-1-[2-(1-pyrazolyl)phenylcarbonyl]-7-methyl-2,3,4,5-tetrahydro-1H-[1,4]-benzodiazepene-3-carboxylic acid, hydroxyamide.

39. The compound according to claim 1 which is 4-(4-But-2-ynyloxybenzenesulfonyl)-1-(5-chloro-2-thienylcarbonyl)-2,3,4,5-tetrahydro-1H-[1,4]benzodiazepine-3-carboxylic acid, hydroxyamide.

40. The compound according to claim 1 which is 4-(4-But-2-ynyloxybenzenesulfonyl)-1-(5-chloro-2-furanylcarbonyl)-2,3,4,5-tetrahydro-1H-[1,4]benzodiazepine-3-carboxylic acid, hydroxyamide.

41. The compound according to claim 1 which is 4-(4-[4-Methoxybut-2-ynyloxy]-benzenesulfonyl)-1-propionyl-2,3,4,5-tetrahydro-1H-[1,4]benzodiazepine-3-carboxylic acid, hydroxyamide.

42. The compound according to claim 1 which is 4-(4-[4-Methoxybut-2-ynyloxy]benzenesulfonyl)-1-(3-thienylcarbonyl)-2,3,4,5-tetrahydro-1H-[1,4]benzodiazepine-3-carboxylic acid, hydroxyamide.

43. The compound according to claim 1 which is 1-(Aminoacetyl)-4-(4-but-2-ynyloxybenzenesulfonyl)-2,3,4,5-tetrahydro-1H-[1,4]benzodiazepine-3-carboxylic acid, hydroxyamide.

44. The compound according to claim 1 which is 1-Hexanoyl-4-(4-[4-methoxybut-2-ynyloxy]benzenesulfonyl)-2,3,4,5-tetrahydro-1H-[1,4]benzodiazepine-3-carboxylic acid, hydroxyamide.

45. The compound according to claim 1 which is 4-(4-But-2-ynyloxybenzenesulfonyl)-1-(N,N-Dimethylaminoacetyl)-2,3,4,5-tetrahydro-1H-[1,4]benzodiazepine-3-carboxylic acid, hydroxyamide.

46. The compound according to claim 1 which is 4-(4-But-2-ynyloxybenzenesulfonyl)-1-(cyclopropylcarbonyl)-2,3,4,5-tetrahydro-1H-[1,4]benzodiazepine-3-carboxylic acid, hydroxyamide.

47. The compound according to claim 1 which is 4-(4-But-2-ynyloxybenzenesulfonyl)-1-(cycloyhexylcarbonyl)-2,3,4,5-tetrahydro-1H-[1,4]-benzodiazepine-3-carboxylic acid, hydroxyamide.

48. The compound according to claim 1 which is 1-Methoxyacetyl-4-(4-[4-methoxybut-2-ynyloxy]benzenesulfonyl)-7-methyl-2,3,4,5-tetrahydro-1H-[1,4]-benzodiazepine-3-carboxylic acid, hydroxyamide.

49. The compound according to claim 1 which is 1-Benzoyl-4-(4-but-2-ynyloxybenzenesulfonyl)-7-methyl-2,3,4,5-tetrahydro-1H-[1,4]-benzodiazepine-3-carboxylic acid, hydroxyamide.

50. The compound according to claim 1 which is 1-(Benzoyl)-4-(4-but-2-ynyloxybenzenesulfonyl)-8-chloro-2,3,4,5-tetrahydro-1H-[1,4]benzodiazepine-3-carboxylic acid, hydroxyamide.

51. The compound according to claim 1 which is 1-Acetyl-4-{[4-(2-butynyloxy)phenyl]sulfonyl}-7-fluoro-N-hydroxy-2,3,4,5-tetrahydro-1H-1,4-benzodiazepine-3-carboxamide.

52. A pharmaceutical composition comprising a compound of Formula 1

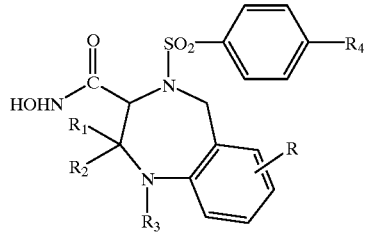

wherein

R is selected from hydrogen, $(C_1-C_3)$ alkyl, —CN, —OR', —SR', —CF$_3$, —OCF$_3$, Cl, F, —N(R')CO$(C_1-C_3)$alkyl, —N(R')(R'), NO$_2$, —CONH$_2$, —SO$_2$NH$_2$, —SO$_2$N(R')(R'), —N(R')COCH$_2$O—$(C_1-C_3)$alkyl, wherein R' is $(C_1-C_3)$ alkyl or hydrogen;

R$_4$ is $(C_2-C_6)$ alkyl-O— containing one triple bond,

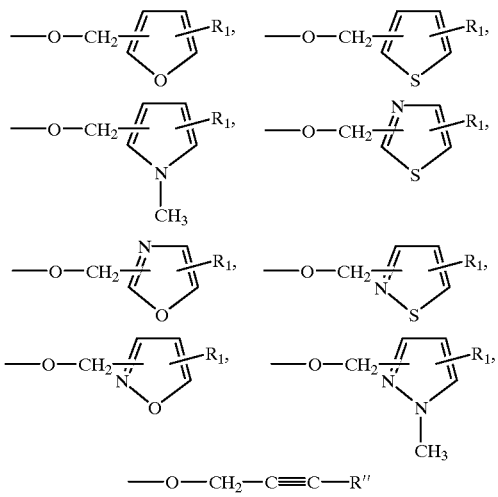

—O—CH$_2$—C≡C—R'' wherein R'' is hydrogen, —CH$_2$OH, $(C_1-C_6)$alkyl, $(C_1-C_6)$alkyl-O—C$_2$—, $(C_1-C_6)$alkyl-S—C$_2$—, $(C_1-C_6)$alkyl-NH—CH$_2$—, [$(C_1-C_3)$alkyl]$_2$-NCH$_2$—, $(C_3-C_6)$cycloalkyl-O—C$_2$—, [$(C_1-C_3)$ alkyl]$_2$-N—(CH$_2$)$_{2-4}$NHCH$_2$—, [$(C_1-C_3)$alkyl]$_2$-N—(CH$_2$)$_{2-4}$N(CH$_3$)CH$_2$—,

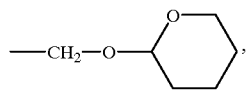

—CH$_2$—O—[phenyl-R$_1$],

—CH$_2$—O—CH$_2$—[phenyl-R$_1$],

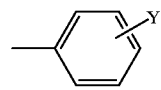

R$_1$ and R$_2$ are each, independently, hydrogen or $(C_1-C_6)$ alkyl,

R$_3$ is $(C_1-C_8)$alkyl, NH$_2$CH$_2$CO—, $(C_1-C_6)$alkylNHCH$_2$CO—, HO(CH$_2$)$_m$CO—, HCO—, Aryl(CH$_2$)$_n$CO—, Heteroaryl(CH$_2$)$_n$CO—, $(C_1-C_3)$alkyl-O—(CH$_2$)$_n$CO—, $(C_1-C_3)$alkylCO—, $(C_1-C_3)$alkylCO—NHCH$_2$CO—, $(C_3-C_7)$cycloalkylCO—, $(C_1-C_3)$alkylSO$_2$—, Aryl(CH$_2$)$_n$SO$_2$—, Heteroaryl(CH$_2$)$_n$SO$_2$—, $(C_1-C_3)$alkyl-O—(CH$_2$)$_m$—SO$_2$—, $(C_1-C_3)$alkyl-O—(CH$_2$)$_m$—, $(C_1-C_3)$alkyl-O—$(C_1-C_3)$alkyl-O—$(C_1-C_3)$alkyl—, HO—$(C_1-C_3)$alkyl-O—$(C_1-C_3)$alkyl-, Aryl-O—CH$_2$CO—, Heteroaryl-O—CH$_2$CO—, ArylCH=CHCO—, HeteroarylCH=CHCO—, $(C_1-C_3)$alkylCH=CHCO—,

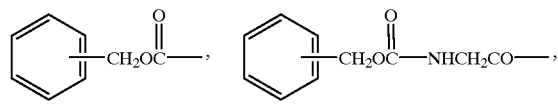

Aryl$(C_1-C_3)$alkyl-, Heteroaryl$(C_1-C_3)$alkyl-, ArylCH=CHC$_2$—, HeteroarylCH=CHCH$_2$—, $(C_1-C_6)$alkylCH=CHCH$_2$—,

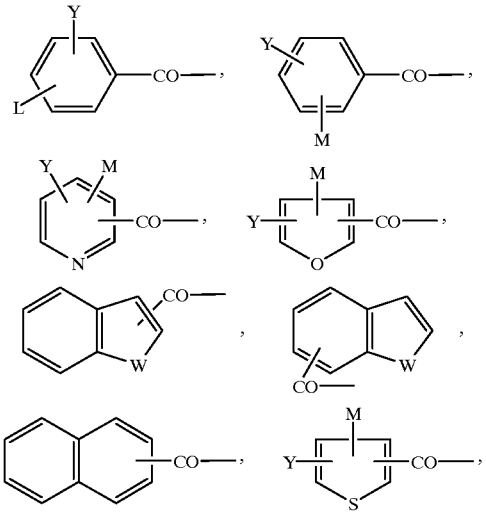

R'OCH$_2$ CH(OR')CO—, (R'OCH$_2$)$_2$C(R')CO—,

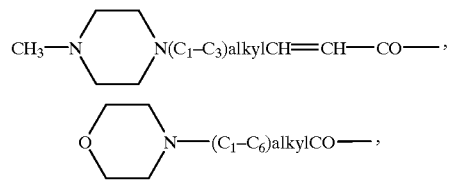

-continued

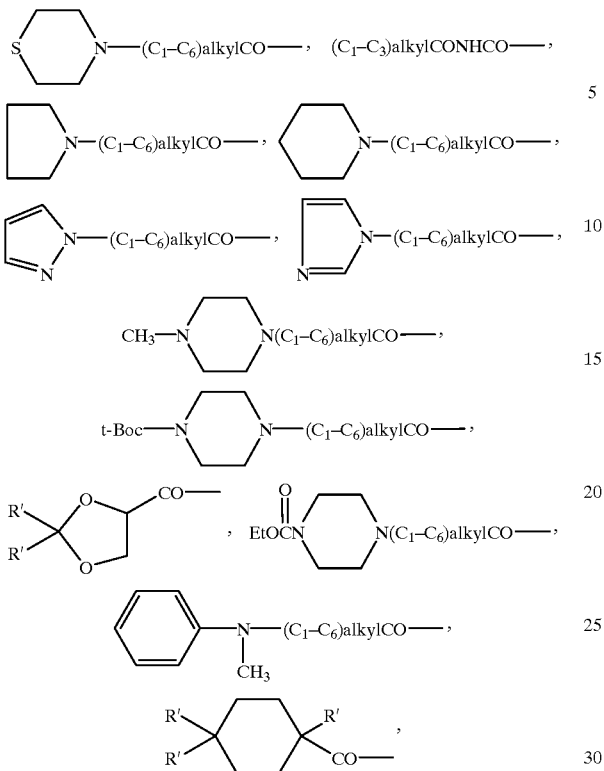

[(C$_1$-C$_6$)alkyl]$_2$-N—(C$_1$-C$_6$)alkyl CO—, or (C$_1$-C$_6$)alkyl-NH—(C$_1$-C$_6$)alkylCO—;
wherein
m=1 to 3; n=0 to 3;
Aryl is

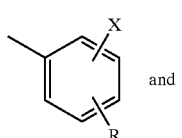

and

Heteroaryl is

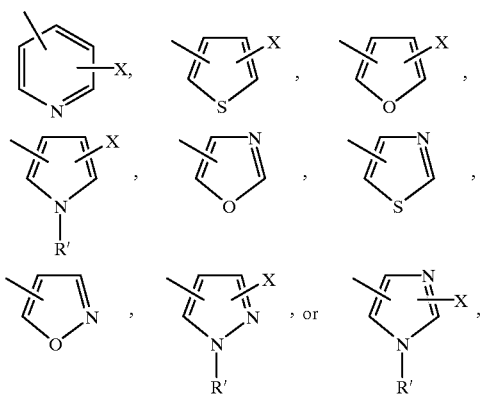

wherein X is hydrogen, halogen, (C$_1$-C$_3$) alkyl or —OCH$_3$, and R and R' are as defined above;

L is hydrogen, (C$_1$-C$_3$)alkyl, —CN, —OR', —SR', —CF$_3$, —OCF$_3$, Cl, F, —N(R')CO(C$_1$-C$_3$)alkyl, N(R')(R'), —NO$_2$, —CONH$_2$, —SO$_2$NH$_2$, —SO$_2$N(R')(R'), —N(R')COCH$_2$O—(C$_1$-C$_3$)alkyl,

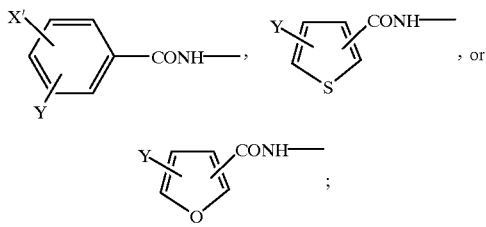

M is

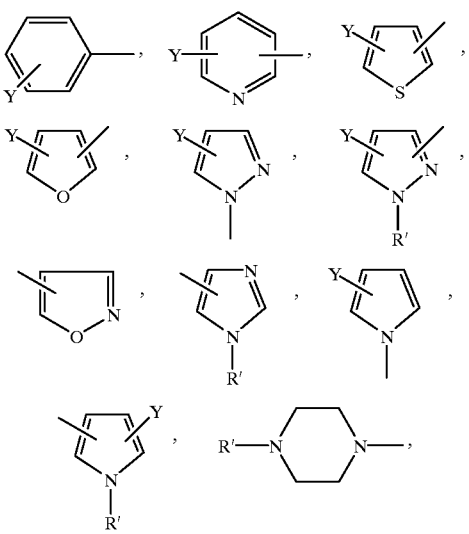

or N(R')(R') where R' is as defined above;

W is O, S, NH or N(C$_1$-C$_3$)alkyl;

Y is hydrogen, F, Cl, CF$_3$ or OCH$_3$; and X' is halogen, hydrogen, (C$_1$-C$_3$)alkyl, O—(C$_1$-C$_3$)alkyl, or —CH$_2$OH; and pharmaceutically acceptable salts thereof.

53. A method of treating a disease condition mediated by matrix metalloproteinase in a mammal in need thereof, which comprises administering to said mammal an effective amount of a compound of Formula 1:

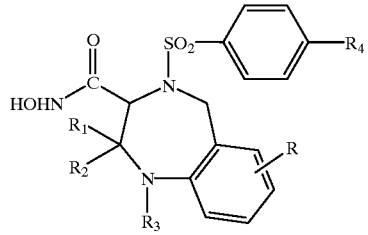

wherein

R is selected from hydrogen, (C$_1$–C$_3$) alkyl, —CN, —OR', —SR', —CF$_3$, —OCF$_3$, Cl, F, —N(R')CO(C$_1$–C$_3$)alkyl, —N(R')(R'), NO$_2$, —CONH$_2$, —SO$_2$NH$_2$, —SO$_2$N(R')(R'), —N(R')COCH$_2$O—(C$_1$–C$_3$)alkyl, wherein R' is (C$_1$–C$_3$) alkyl or hydrogen;

R$_4$ is (C$_2$–C$_6$) alkyl-O— containing one triple bond,

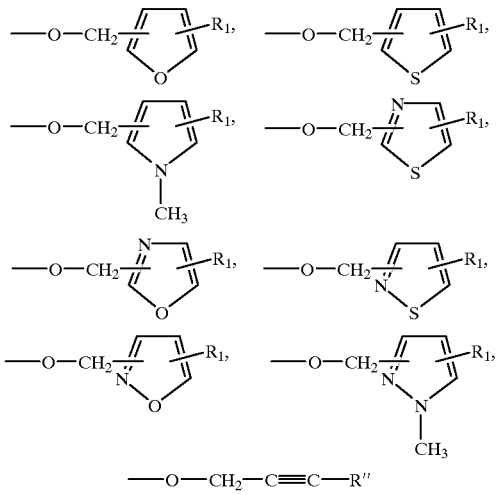

—O—CH$_2$—C≡C—R'' wherein R'' is hydrogen, —CH$_2$OH, (C$_1$–C$_6$)alkyl, (C$_1$–C$_6$)alkyl-O—CH$_2$—, (C$_1$–C$_6$)alkyl-S—CH$_2$—, (C$_1$–C$_6$)alkyl-NH—CH$_2$—, [(C$_1$–C$_3$)alkyl]$_2$-NCH$_2$—, (C$_3$–C$_6$)cycloalkyl-O—CH$_2$—, [(C$_1$–C$_3$) alkyl]$_2$-N—(CH$_2$)$_{2-4}$NHCH$_2$—, [(C$_1$–C$_3$)alkyl]$_2$-N—(CH$_2$)$_{2-4}$N(CH$_3$)CH$_2$—,

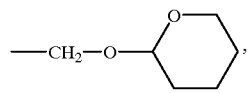

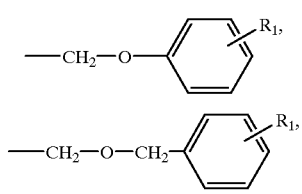

-continued

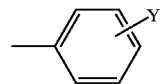

R$_1$ and R$_2$ are each, independently, hydrogen or C$_1$–C$_3$ alkyl,

R$_3$ is (C$_1$–C$_8$)alkyl, NH$_2$CH$_2$CO—, (C$_1$–C$_6$)alkylNHCH$_2$CO—, HO(CH$_2$)$_m$CO—, HCO—, Aryl(CH$_2$)$_n$CO—, Heteroaryl(CH$_2$)$_n$CO—, (C$_1$–C$_3$)alkyl-O—(CH$_2$)$_n$CO—, (C$_1$–C$_3$)alkylCO—, (C$_1$–C$_3$)alkylCO—NHCH$_2$CO—, (C$_3$–C$_7$)cycloalkylCO—, (C$_1$–C$_3$)alkylSO$_2$—, Aryl(CH$_2$)$_n$SO$_2$—, Heteroaryl(CH$_2$)$_n$SO$_2$—, (C$_1$–C$_3$)alkyl-O—(CH$_2$)$_m$—SO$_2$—, (C$_1$–C$_3$)alkyl-O—(CH$_2$)$_m$—, (C$_1$–C$_3$)alkyl-O—(C$_1$–C$_3$)alkyl-O—(C$_1$–C$_3$)alkyl—, HO—(C$_1$–C$_3$)alkyl-O—(C$_1$–C$_3$)alkyl—, Aryl-O—CH$_2$CO—, Heteroaryl-O—CH$_2$CO—, ArylCH=CHCO—, HeteroarylCH=CHCO—, (C$_1$–C$_3$)alkylCH=CHCO—,

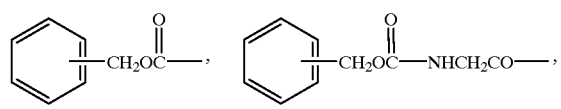

Aryl(C$_1$–C$_3$)alkyl—, Heteroaryl(C$_1$–C$_3$)alkyl-, ArylCH=CHC$_2$—, HeteroarylCH=CHCH$_2$—, (C$_1$–C$_6$)alkylCH=CHCH$_2$—,

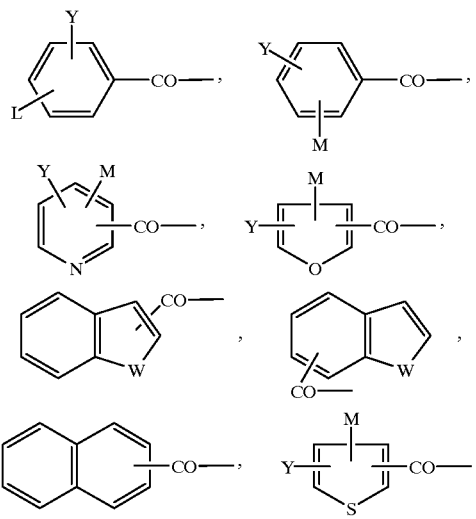

R'OCH$_2$CH(OR')CO—, (R'OCH$_2$)$_2$C(R')CO—,

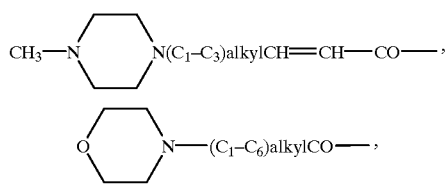

-continued

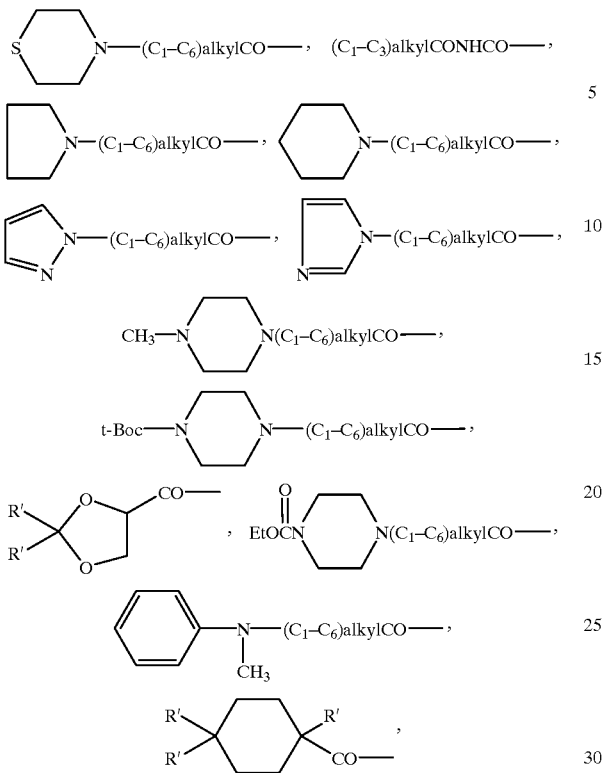

[(C$_1$-C$_6$)alkyl]$_2$-N—(C$_1$-C$_6$)alkyl CO—, or (C$_1$-C$_6$)alkyl-NH—(C$_1$-C$_6$)alkylCO—;
wherein
m=1 to 3; n=0 to 3;
Aryl is

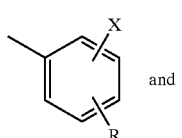

and

Heteroaryl is

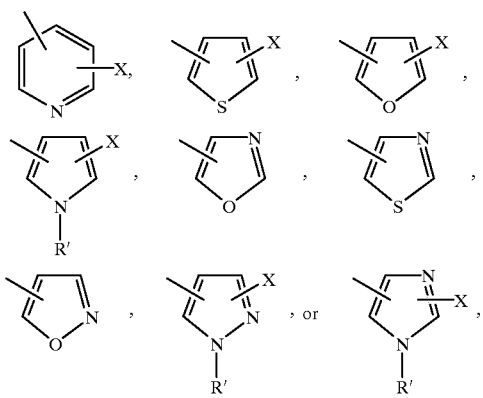

wherein X is hydrogen, halogen, (C$_1$-C$_3$)alkyl or —OCH$_3$, and R and R' are as defined above;
L is hydrogen, (C$_1$-C$_3$)alkyl, —CN, —OR', —SR', —CF$_3$, —OCF$_3$, Cl, F, —N(R')CO(C$_1$-C$_3$)alkyl, N(R')(R'), —NO$_2$, —CONH$_2$, —SO$_2$NH$_2$, —SO$_2$N(R')(R'), —N(R')COCH$_2$O—(C$_1$-C$_3$)alkyl,

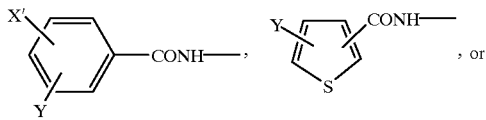

M is

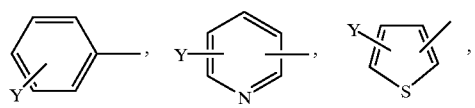
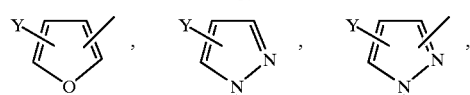
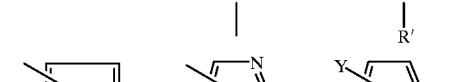
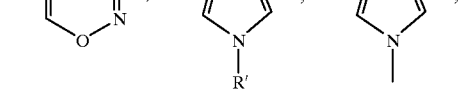
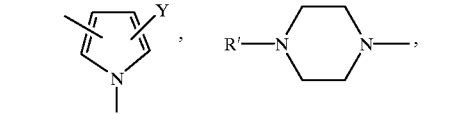
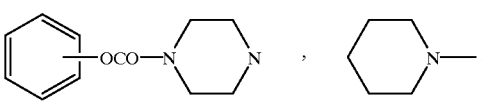
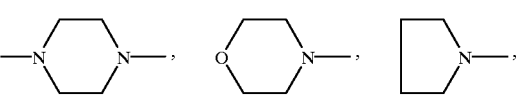

or

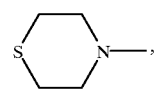

N(R')(R') where R' is as defined above;
W is O, S, NH or N(C$_1$-C$_3$)alkyl;
Y is hydrogen, F, Cl, CF$_3$ or OCH$_3$; and X' is halogen, hydrogen, (C$_1$-C$_3$)alkyl, O—(C$_1$-C$_3$)alkyl, or —CH$_2$OH; or a pharmaceutically acceptable salt thereof, said disease condition being selected from the group consisting of restenosis, MMP-mediated osteopenias, inflammatory diseases of the central nervous system, skin aging, osteoarthritis, rheumatoid arthritis, septic arthritis, corneal ulceration, abnormal wound healing, bone disease, proteinuria, aneurysmal aortic disease, degenerative cartilage loss following traumatic joint injury, demyelinating diseases of the nervous system, cirrhosis of the liver, glomerular disease of the kidney, premature rupture of fetal membranes, inflammatory bowel disease, periodontal disease, age-related macular degeneration, diabetic retinopathy, proliferative vitreoretinopathy, retinopathy of prematurity, ocular inflammation, keratoconus, Sjogren's syndrome, myopia, ocular tumors, ocular angiogenesis/neo-vascularization and corneal graft rejection.

54. A method of treating a patient suffering from a condition selected from the group consisting of osteoarthritis, rheumatoid arthritis, degenerative cartilage loss, and tumor growth which comprises administering to said patient an effective amount of a compound of Formula 1:

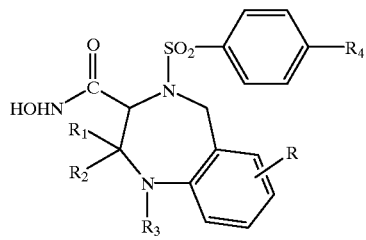

wherein

R is selected from hydrogen, $(C_1-C_3)$alkyl, —CN, —OR', —SR', —CF$_3$, —OCF$_3$, Cl, F, —N(R')CO($C_1-C_3$) alkyl, —N(R')(R'), NO$_2$, —CONH$_2$, —SO$_2$NH$_2$, —SO$_2$N(R')(R'), —N(R')COCH$_2$O—($C_1-C_3$)alkyl, wherein R' is $(C_1-C_3)$ alkyl or hydrogen;

R$_4$ is $(C_2-C_6)$ alkyl-O— containing one triple bond,

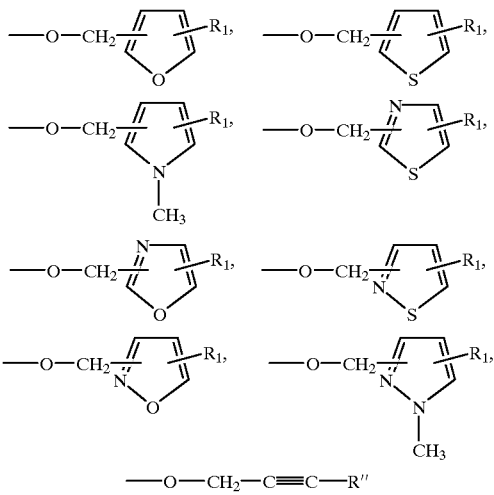

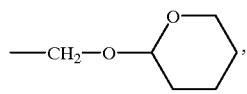

wherein R" is hydrogen, —CH$_2$OH, $(C_1-C_6)$alkyl, $(C_1-C_6)$alkyl-O—CH$_2$—, $(C_1-C_6)$alkyl-S—CH$_2$—, $(C_1-C_6)$alkyl-NH—CH$_2$—, [$(C_1-C_3)$alkyl]$_2$-NCH$_2$—, $(C_3-C_6)$cycloalkyl-O—CH$_2$—, [$(C_1-C_3)$alkyl]$_2$-N—(CH$_2$)$_{2-4}$NHCH$_2$—, [$(C_1-C_3)$ alkyl]$_2$-N—(CH$_2$)$_{2-4}$N(CH$_3$)CH$_2$—,

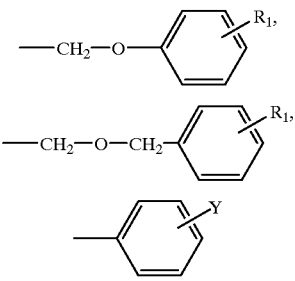

R$_1$ and R$_2$ are each, independently, hydrogen or $C_1-C_6$alkyl,

R$_3$ is $(C_1-C_8)$alkyl, NH$_2$CH$_2$CO—, $(C_1-C_6)$ alkylNHCH$_2$CO—, HO(CH$_2$)$_m$CO—, HCO—, Aryl (CH$_2$)$_n$CO—, Heteroaryl(CH$_2$)$_n$CO—, $(C_1-C_3)$alkyl-O—(CH$_2$)$_n$CO—, $(C_1-C_3)$alkylCO—, $(C_1-C_3)$ alkylCO—NHCH$_2$CO—, $(C_3-C_7)$cycloalkylCO—, $(C_1-C_3)$alkylSO$_2$—, Aryl(CH$_2$)$_n$SO$_2$—, Heteroaryl (CH$_2$)$_n$SO$_2$—, $(C_1-C_3)$alkyl-O—(CH$_2$)$_m$—SO$_2$—, $(C_1-C_3)$alkyl-O—(CH$_2$)$_m$—, $(C_1-C_3)$alkyl-O—$(C_1-C_3)$alkyl-O—$(C_1-C_3)$alkyl—, HO—$(C_1-C_3)$ alkyl-O—$(C_1-C_3)$alkyl-, Aryl-O—CH$_2$CO—, Heteroaryl-O—CH$_2$CO—, ArylCH=CHCO—, HeteroarylCH=CHCO—, $(C_1-C_3)$ alkylCH=CHCO—,

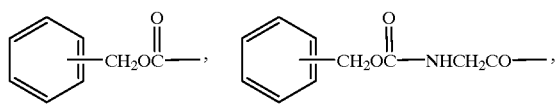

Aryl$(C_1-C_3)$alkyl-, Heteroaryl$(C_1-C_3)$alkyl-, ArylCH=CHCH$_2$—, HeteroarylCH=CHCH$_2$—, $(C_1-C_6)$alkylCH=CHCH$_2$—,

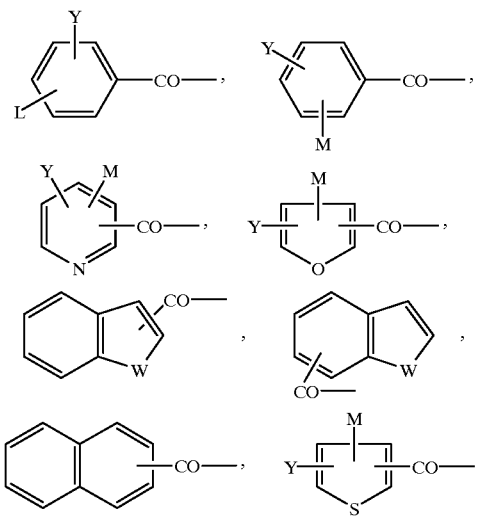

R'OCH$_2$CH(OR')CO—, (R'OCH$_2$)$_2$C(R')CO—,

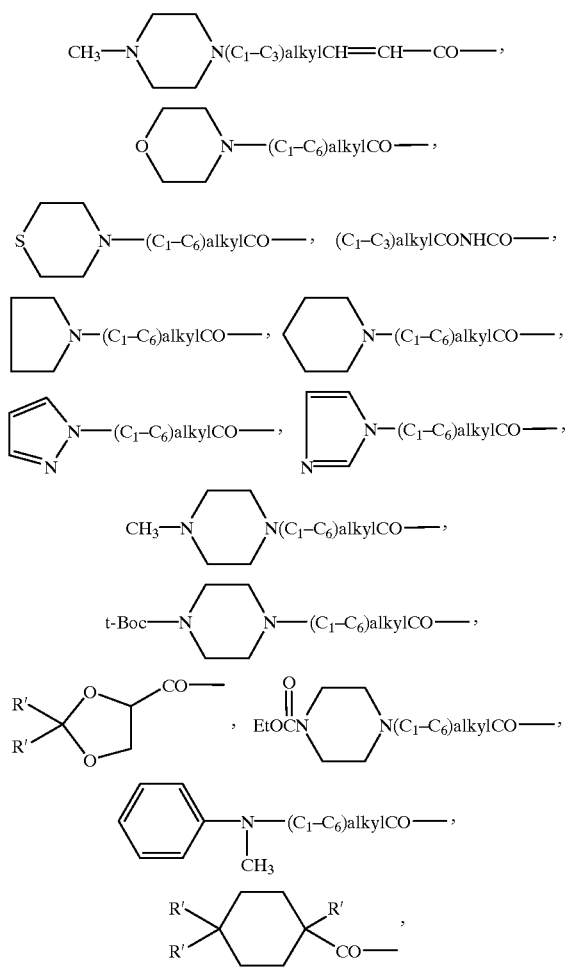

[(C$_1$–C$_6$)alkyl]$_2$-N—(C$_1$–C$_6$)alkyl CO—, or (C$_1$–C$_6$)alkyl-NH—(C$_1$–C$_6$)alkylCO—;
wherein
m=1 to 3; n=0 to 3;
Aryl is

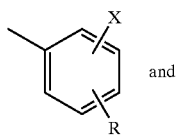 and

Heteroaryl is

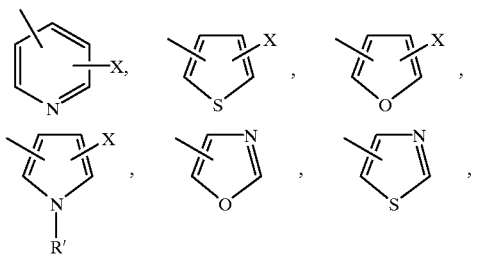

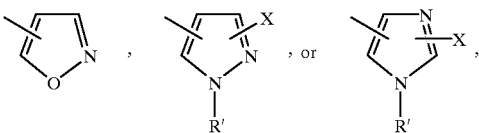

wherein X is hydrogen, halogen, (C$_1$–C$_3$) alkyl or —OCH$_3$, and R and R' are as defined above;

L is hydrogen, (C$_1$–C$_3$)alkyl, —CN, —OR', —SR', —CF$_3$, —OCF$_3$, Cl, F, —N(R')CO(C$_1$–C$_3$)alkyl, N(R')(R'), —NO$_2$, —CONH$_2$, —SO$_2$NH$_2$, —SO$_2$N(R')(R'), —N(R')COCH$_2$O—(C$_1$–C$_3$)alkyl,

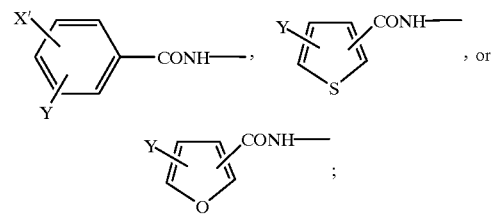

M is

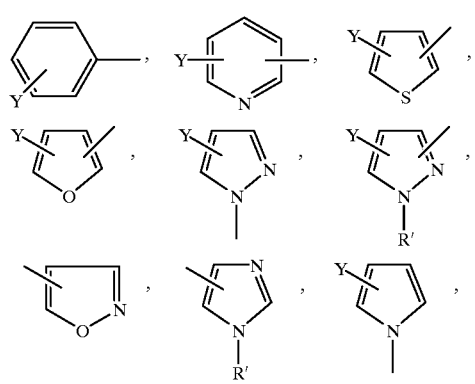

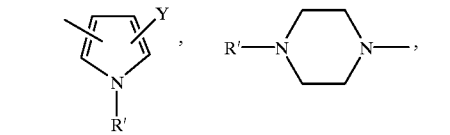

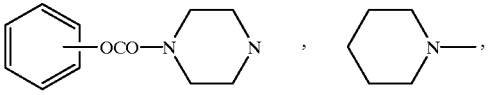

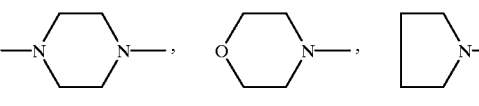

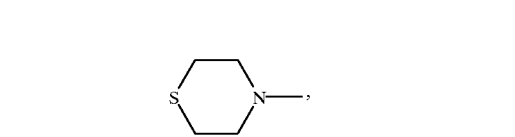

or N(R')(R') where R' is as defined above;
W is O, S, NH or N(C$_1$–C$_3$)alkyl;
Y is hydrogen, F, Cl, CF$_3$ or OCH$_3$; and X' is halogen, hydrogen, (C$_1$–C$_3$)alkyl, O—(C$_1$–C$_3$)alkyl, or —CH$_2$OH; and pharmaceutically acceptable salts thereof.

* * * * *